(12) United States Patent
Johnson et al.

(10) Patent No.: US 11,603,387 B2
(45) Date of Patent: Mar. 14, 2023

(54) SOCS MIMETICS FOR THE TREATMENT OF DISEASES

(71) Applicant: UNIVERSITY OF FLORIDA RESEARCH FOUNDATION, INC., Gainesville, FL (US)

(72) Inventors: Howard M. Johnson, Gainesville, FL (US); Joseph Larkin, Gainesville, FL (US); Chulbul M. Ahmed, Gainesville, FL (US); Lindsey Jager, Madison, WI (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 15/113,725

(22) PCT Filed: Jan. 23, 2015

(86) PCT No.: PCT/US2015/012760
§ 371 (c)(1),
(2) Date: Jul. 22, 2016

(87) PCT Pub. No.: WO2015/112904
PCT Pub. Date: Jul. 30, 2015

(65) Prior Publication Data
US 2017/0008929 A1    Jan. 12, 2017

Related U.S. Application Data

(60) Provisional application No. 61/931,363, filed on Jan. 24, 2014.

(51) Int. Cl.
| | |
|---|---|
| C07K 7/00 | (2006.01) |
| C07K 14/00 | (2006.01) |
| A61K 38/17 | (2006.01) |
| C07K 7/08 | (2006.01) |
| A61K 45/06 | (2006.01) |
| A61K 9/127 | (2006.01) |
| A61K 31/138 | (2006.01) |
| A61K 31/7048 | (2006.01) |
| A61K 31/337 | (2006.01) |
| A61K 31/513 | (2006.01) |
| A61K 31/475 | (2006.01) |
| A61K 31/506 | (2006.01) |
| A61K 31/4745 | (2006.01) |
| A61K 31/704 | (2006.01) |
| C07K 14/47 | (2006.01) |

(Continued)

(52) U.S. Cl.
CPC .............. *C07K 7/08* (2013.01); *A61K 9/127* (2013.01); *A61K 31/138* (2013.01); *A61K 31/337* (2013.01); *A61K 31/475* (2013.01); *A61K 31/4745* (2013.01); *A61K 31/506* (2013.01); *A61K 31/513* (2013.01); *A61K 31/675* (2013.01); *A61K 31/704* (2013.01); *A61K 31/7048* (2013.01); *A61K 38/10* (2013.01); *A61K 38/17* (2013.01); *A61K 45/06* (2013.01); *C07K 14/4718* (2013.01); *C12Q 1/6883* (2013.01); *A61K 9/0014* (2013.01); *C12Q 2600/158* (2013.01)

(58) Field of Classification Search
None
See application file for complete search history.

(56) References Cited

U.S. PATENT DOCUMENTS

| | | |
|---|---|---|
| 4,179,337 A | 12/1979 | Davis et al. |
| 4,625,014 A | 11/1986 | Senter et al. |

(Continued)

FOREIGN PATENT DOCUMENTS

| | | | |
|---|---|---|---|
| WO | WO 2010/151495 | 12/2010 | |
| WO | WO-2010151495 A2 * | 12/2010 | ............. A61K 9/127 |

OTHER PUBLICATIONS

"Protein Mimetic" available online at https://en.wikipedia.org/wiki/Protein_mimetic, 1 page (2015).*

(Continued)

*Primary Examiner* — Thea D' Ambrosio
(74) *Attorney, Agent, or Firm* — Saliwanchik, Lloyd & Eisenschenk

(57) ABSTRACT

The subject invention concerns peptide mimetics of SOCS proteins and methods of use. In one embodiment, a peptide mimetic of the invention binds to a SOCS1 and a SOCS3 target protein. In a specific embodiment, a peptide mimetic of the invention comprises the amino acid sequence of SEQ ID NO:1 and/or SEQ ID NO:2 and/or SEQ ID NO:51, or a functional fragment or variant thereof. In a further embodiment, a peptide of the invention can comprise multiple copies of the mimetic sequence. In one embodiment, a peptide of the invention comprises two or more copies of SEQ ID NO:1 and/or SEQ ID NO:2 and/or SEQ ID NO:51. In a specific embodiment, a peptide mimetic of the invention comprises the amino acid sequence of SEQ ID NO:3 and/or SEQ ID NO:4 to and/or SEQ ID NO:52, or a functional fragment or variant thereof. The subject invention also pertains to methods of treating and/or preventing autoimmune conditions and/or disorders. In one embodiment, one or more peptide mimetics of the invention are used to treat an autoimmune condition or disorder in a person or animal. In a specific embodiment, a mimetic of the invention is used to treat SLE in a person or animal. The subject invention also concerns methods for diagnosing and/or monitoring progression of SLE in a person or animal.

35 Claims, 19 Drawing Sheets
Specification includes a Sequence Listing.

(51) Int. Cl.
  *A61K 31/675* (2006.01)
  *C12Q 1/6883* (2018.01)
  *A61K 38/10* (2006.01)
  *A61K 9/00* (2006.01)

(56) References Cited

U.S. PATENT DOCUMENTS

| | | |
|---|---|---|
| 5,034,322 A | 7/1991 | Rogers et al. |
| 5,106,739 A | 4/1992 | Comai et al. |
| 5,252,348 A | 10/1993 | Schreier et al. |
| 5,625,136 A | 4/1997 | Koziel et al. |
| 5,763,585 A | 6/1998 | Nag |
| 2002/0035243 A1 | 3/2002 | Imfeld et al. |
| 2002/0120100 A1 | 8/2002 | Bonny |
| 2003/0032594 A1 | 2/2003 | Bonny |
| 2009/0209458 A1 | 8/2009 | Hawiger et al. |

OTHER PUBLICATIONS

Bowie et al. (Science, 1990, 247:1306-1310) (Year: 1990).*
Burgess et al. (J. Cell Biol. 111:2129-2138, 1990) (Year: 1990).*
Lazar et al. (Mol. Cell. Biol., 8:1247-1252, 1988) (Year: 1988).*
Bork (Genome Research, 2000,10:398-400) (Year: 2000).*
UniProt Database, Accession No. O15524, 10 pages (accessed on Nov. 8, 2017) (Year: 2017).*
Chen et al., Adv. Drug Deliv. Rev. 65:1357-1369 (2013) (Year: 2013).*
Sebbage et al., Bioscience Horizons 2:64-72 (2009) (Year: 2009).*
U.S. Appl. No. 17/032,961, filed Sep. 2020, Johnson et al.*
Yamaguchi et al., J. Biomed. Biotechnol. 2011:6 pages (2011) (Year: 2011).*
Akahoshi, M. et al. "Th1/Th2 balance of peripheral T helper cells in systemic lupus erythematosus" *Arthritis Rheum.*, 1999, 42:1644-1648.
Alexander, W.S. "Suppressors of cytokine signalling (SOCS) in the immune system." *Nat. Rev. Immunol.*, 2002, 2:410-416.
Alexander, W.S. et al. "SOCS1 is a critical inhibitor of interferon gamma signaling and prevents the potentially fatal neonatal actions of this cytokine" *Cell*, 1999, 98:597-608.
Balomenos, D. et al. "Interferon-gamma is required for lupus-like disease and lymphoaccumulation in MRL-lpr mice" *J. Clin. Invest.*, 1998, 101:364-371.
Bedoya, S.K. et al. "Isolation and Th17 Differentiation of Naïve CD4 T Lymphocytes." *J. Vis. Exp.*, 2013, 79:e50765, doi:10.3791/50765, 12 pages.
Bhattacharyya, S. et al. "Glucocorticoids target suppressor of cytokine signaling 1 (SOCS1) and type 1 interferons to regulate Toll-like receptor-induced STAT1 activation" *Proc. Natl. Acad. Sci. U.S.A.*, 2011, 108:9554-9559.
Bombardier, C. et al. "Derivation of the Sledai. A disease activity index for lupus patients. the committee on prognosis studies in SLE" *Arthritis Rheum.*, 1992, 35(6):630-40.
Bouzahzah, F. et al. "CD4+ T cells from lupus-prone mice avoid antigen-specific tolerance induction in vivo" *J. Immunol.*, 2003, 170:741-748.
Caretto, D. et al. "Cutting edge: the Th1 response inhibits the generation of peripheral regulatory T cells" *J. Immunol.*, 2010, 184:30-34.
Chan, H.C. et al. "Suppressor of cytokine signaling 1 gene expression and polymorphisms in systemic lupus erythematosus" *Lupus*, 2010, 19:696-702.
Cheng, G. et al. "T-cell tolerance and the multi-functional role of IL-2R signaling in T-regulatory cells" *Immunol. Rev.*, 2011, 241:63-76.
Collins, E.L. et al. "Inhibition of SOCS1-/- lethal autoinflammatory disease correlated to enhanced peripheral Foxp3+ regulatory T cell homeostasis" *J. Immunol.*, 2011, 187:2666-2676.

Cozzo, C. et al. "Cutting edge: self-peptides drive the peripheral expansion of CD4+CD25+ regulatory T cells" *J. Immunol.*, 2003, 171:5678-5682.
De Boer, H.A. et al. "The tac promoter: a functional hybrid derived from the trp and lac promoters" *Proc. Natl. Acad. Sci. U.S.A.*, 1983, 80(1):21-25.
Desai-Mehta, A. et al. "Hyperexpression of CD40 ligand by B and T cells in human lupus and its role in pathogenic autoantibody production" *J. Clin. Invest.*, 1996, 97:2063-2073.
Diehl, S. et al. "Inhibition of Th1 differentiation by IL-6 is mediated by SOCS1" *Immunity*, 2000, 13:805-815.
Egwuagu, C.E. and Larkin, J. III. "Therapeutic targeting of STAT pathways in CNS autoimmune diseases" *JAK-STAT*, 2013, 2:1, e24134, 8 pages.
Felgner, P.L. et al. "Lipofection: a highly efficient, lipid-mediated DNA-transfection procedure" *Proc Natl Acad Sci U.S.A.*, 1987, 84(21):7413-7417.
Feng, T. et al. "Interleukin-12 converts Foxp3+ regulatory T cells to interferon-gamma-producing Foxp3+ T cells that inhibit colitis" *Gastroenterology*, 2011, 140:2031-2043.
Fujimoto, M. et al. "Inadequate induction of suppressor of cytokine signaling-1 causes systemic autoimmune diseases" *Int. Immunol.*, 2004, 16:303-314.
Gett, A.V. and Hodgkin, P.D. "Cell division regulates the T cell cytokine repertoire, revealing a mechanism underlying immune class regulation" *Proc. Natl. Acad. Sci. U.S.A.*, 1998, 95:9488-9493.
Greenlund, A.C. et al. "Stat recruitment by tyrosine-phosphorylated cytokine receptors: an ordered reversible affinity-driven process" *Immunity*, 1995, 2:677-687.
Gurevitz, S.L. et al. "Systemic lupus erythematosus: a review of the disease and treatment options" *Consult. Pharm.*, 2013, 28:110-121.
Haas, C. et al. "IFN-gamma receptor deletion prevents autoantibody production and glomerulonephritis in lupus-prone (NZB × NZW)F1 mice" *J. Immunol.*, 1998, 160:3713-3718.
Hanada, T. et al. "Suppressor of cytokine signaling-1 is essential for suppressing dendritic cell activation and systemic autoimmunity" *Immunity*, 2003, 19:437-450.
Hirahara, K. et al. "Mechanisms underlying helper T-cell plasticity: implications for immune-mediated disease" *J. Allergy Clin. Immunol.*, 2013, 131:1276-1287.
Iannone, F. and Lapadula, G. "The inhibitor of costimulation of T cells: Abatacept" *J. Rheumatol.*, 2012, 39 Suppl. 89:100-102.
Jabs, D.A. et al. "Anti-CD4 monoclonal antibody therapy suppresses autoimmune disease in MRL/Mp-lpr/lpr mice" *Cell. Immunol.*, 1992, 141:496-507.
Jager, L.D. et al. "The kinase inhibitory region of SOCS-1 is sufficient to inhibit T-helper 17 and other immune functions in experimental allergic encephalomyelitis" *J. Neuroimmunol.*, 2011, 232:108-118.
Jorgensen, T.N. et al. "Type I interferon signaling is involved in the spontaneous development of lupus-like disease in B6.Nba2 and (B6.Nba2 × NZW)F(1) mice" *Genes Immun.*, 2007, 8:653-662.
Karonitsch, T. et al. "Activation of the interferon-gamma signaling pathway in systemic lupus erythematosus peripheral blood mononuclear cells" *Arthritis Rheum.*, 2009, 60:1463-1471.
Knosp, C.A. and Johnston, J.A. "Regulation of CD4+ T-cell polarization by suppressor of cytokine signaling proteins" *Immunology*, 2012, 135:101-111.
Kohler, G. and Milstein, C. "Continuous cultures of fused cells secreting antibody of predefined specificity" *Nature*, 1975, 256(5517):495-497.
Kotenko, S.V. and Pestka, S. "Jak-Stat signal transduction pathway through the eyes of cytokine class II receptor complexes" *Oncogene*, 2000, 19:2557-2565.
Larkin, J. III et al. "Regulation of interferon gamma signaling by suppressors of cytokine signaling and regulatory T cells" *Frontiers in Immunology*, 2013, vol. 4, article 469, 8 pages.
Larkin, J., III et al. "Activation of CD4+ CD25+ regulatory T cell suppressor function by analogs of the selecting peptide" *Eur. J. Immunol.*, 2007, 37:139-146.
Lau, K. et al. "Inhibition of type 1 diabetes correlated to a Lactobacillus johnsonii N6.2-mediated Th17 bias" *J. Immunol.*, 2011, 186:3538-3546.

(56) References Cited

OTHER PUBLICATIONS

Ledford, H. "Melanoma drug wins US approval" *Nature*, 2011, 471:561.

Li, Y. et al. "Monocyte surface expression of Fcgamma receptor RI (CD64), a biomarker reflecting type-I interferon levels in systemic lupus erythematosus" *Arthritis Res. Ther.*, 2010, 12:R90.

Mangan, P.R. et al. "Transforming growth factor-beta induces development of the T(H)17 lineage" *Nature*, 2006, 441:231-234.

Mohan, C. et al. "Genetic dissection of Sle pathogenesis: Sle3 on murine chromosome 7 impacts T cell activation, differentiation, and cell death" *J. Immunol.*, 1999, 162:6492-6502.

Mondino, A. and Jenkins, M.K. "Surface proteins involved in T cell costimulation" *J. Leukoc. Biol.*, 1994, 55:805-815.

Morel, L. et al. "Genetic reconstitution of systemic lupus erythematosus immunopathology with polycongenic murine strains" *Proc. Natl. Acad. Sci. U.S.A.*, 2000, 97:6670-6675.

Nacionales, D.C. et al. "Deficiency of the type I interferon receptor protects mice from experimental lupus" *Arthritis Rheum.*, 2007, 56:3770-3783.

Nakashima, H. et al. "The combination of polymorphisms within interferon-gamma receptor 1 and receptor 2 associated with the risk of systemic lupus erythematosus" *FEBS Lett.*, 1999, 453:187-190.

Pardanani, A. et al. "Safety and efficacy of TG101348, a selective JAK2 inhibitor, in myelofibrosis" *J. Clin. Oncol.*, 2011, 29:789-796.

Parry, R.V. et al. "Ligation of the T cell co-stimulatory receptor CD28 activates the serine-threonine protein kinase protein kinase B" *Eur. J. Immunol.*, 1997, 27:2495-2501.

Picca, C.C. et a. "Role of TCR specificity in CD4+ CD25+ regulatory T-cell selection" *Immunol. Rev.*, 2006, 212:74-85.

Pickering, M.C. and Walport, M.J. "Links between complement abnormalities and systemic lupus erythematosus" *Rheumatology (Oxford)*, 2000, 39:133-141.

Pierau, M. et al. "Protein kinase B/Akt signals impair Th17 differentiation and support natural regulatory T cell function and induced regulatory T cell formation" *J. Immunol.*, 2009, 183:6124-6134.

Piganis, R.A. et al. "Suppressor of cytokine signaling (SOCS) 1 inhibits type I interferon (IFN) signaling via the interferon alpha receptor (IFNAR1)-associated tyrosine kinase Tyk2" *J. Biol. Chem.*, 2011, 286:33811-33818.

Platanias, L.C. and Fish, E.N. "Signaling pathways activated by interferons" *Exp. Hematol.*, 1999, 27:1583-1592.

Ramgolam, V.S. and Markovic-Plese, S. "Regulation of Suppressors of cytokine signaling as a therapeutic approach in autoimmune diseases, with an emphasis on multiple sclerosis" *J. Signal Transduction*, 2011, vol. 2011, Article ID 635721, 7 pages.

Ronnblom, L.E. et al. "Autoimmunity after alpha-interferon therapy for malignant carcinoid tumors" *Ann. Intern. Med.*, 1991, 115:178-183.

Santiago-Raber, M.L. et al. "Type-I interferon receptor deficiency reduces lupus-like disease in NZB mice" *J. Exp. Med.*, 2003, 197:777-788.

Santoro, T.J. et al. "The contribution of L3T4+ T cells to lymphoproliferation and autoantibody production in MRL-lpr/lpr mice" *J. Exp. Med.*, 1988, 167:1713-1718.

Schroder, K. et al. "Interferon-gamma: an overview of signals, mechanisms and functions" *J. Leukoc. Biol.*, 2004, 75:163-189.

Sharabi, A. et al. "A tolerogenic peptide that induces suppressor of cytokine signaling (SOCS)-1 restores the aberrant control of IFN-gamma signaling in lupus-affected (NZB × NZW)F1 mice" *Clin. Immunol.*, 2009, 133:61-68.

Stekman, I.L. et al. Enhanced CD3-mediated T lymphocyte proliferation in patients with systemic lupus erythematosus *Arthritis Rheum.*, 1991, 34:459-467.

Suen, J.L. et al. "Altered homeostasis of CD4(+) FoxP3(+) regulatory T-cell subpopulations in systemic lupus erythematosus" *Immunology*, 2009, 127:196-205.

Szabo, S.J. et al. "Distinct effects of T-bet in TH1 lineage commitment and IFN-gamma production in CD4 and CD8 T cells" *Science*, 2002, 295:338-342.

Szente, B.E. et al. "The C-terminus of IFN gamma is sufficient for intracellular function" *Biochem. Biophys. Res. Commun.*, 1994, 203:1645-1654.

Takahashi, R. et al. "SOCS1 is essential for regulatory T cell functions by preventing loss of Foxp3 expression as well as IFN-{gamma} and IL-17A production" *J. Exp. Med.*, 2011, 208:2055-2067.

Takahashi, S. et al. "Imbalance towards Th1 predominance is associated with acceleration of lupus-like autoimmune syndrome in MRL mice" *J. Clin. Invest.*, 1996, 97:1597-1604.

Tam, J.P. "Synthetic Peptide Vaccine Design: Synthesis and Properties of a High-Density Multiple Antigenic Peptide System" *Biochemistry*, 1988, 85:5409-5413.

Tamiya, T. et al. "Suppressors of cytokine signaling (SOCS) proteins and JAK/STAT pathways" *Arterioscler. Thromb. Vasc. Biol.*, 2011, 31:980-985.

Tan, E.M. et al. "The 1982 revised criteria for the classification of systemic lupus erythematosus" *Arthritis Rheum.*, 1982, 25:1271-1277.

Testi, R. et al. "The CD69 receptor: a multipurpose cell-surface trigger for hematopoietic cells" *Immunol. Today*, 1994, 15:479-483.

Thiam, K. et al. "IFN-gamma-derived lipopeptides: influence of lipid modification on the conformation and the ability to induce MHC class II expression on murine and human cells" *J. Med. Chem.*, 1999, 42:3732-3736; abstract.

Tivol, E.A. et al. "Costimulation and autoimmunity" *Curr. Opin. Immunol.*, 1996, 8:822-830.

Tsao, J.T. et al. "The analysis of CIS, SOCS1, SOSC2 and SOCS3 transcript levels in peripheral blood mononuclear cells of systemic lupus erythematosus and rheumatoid arthritis patients" *Clin. Exp. Med.*, 2008, 8:179-185.

Tsokos, G.C. "Systemic lupus erythematosus" *N. Engl. J. Med.*, 2011, 365:2110-2121.

Valencia, X. et al. "Deficient CD4+CD25 high T regulatory cell function in patients with active systemic lupus erythematosus" *J. Immunol.*, 2007, 178:2579-2588.

Vratsanos, G.S. et al. "CD4(+) T cells from lupus-prone mice are hyperresponsive to T cell receptor engagement with low and high affinity peptide antigens: a model to explain spontaneous T cell activation in lupus" *J. Exp. Med.*, 2001, 193:329-337.

Wang, S. et al. "Jak/STAT signaling is involved in the inflammatory infiltration of the kidneys in MRL/lpr mice" *Lupus*, 2010, 19:1171-1180.

Wofsy, D. et al. "Treatment of murine lupus with monoclonal anti-T cell antibody" *J. Immunol.*, 1985, 134:852-857.

Xu, D. et al. "Systemic induction of a potato pin2 promoter by wounding, methyl jasmonate, and abscisic acid in transgenic rice plants" *Plant Molecular Biology*, 1993, 22:573-588.

Yan, B. et al. "Dysfunctional CD4+,CD25+ regulatory T cells in untreated active systemic lupus erythematosus secondary to interferon-alpha-producing antigen-presenting cells" *Arthritis Rheum.*, 2008, 58:801-812.

Yoshimura, A. et al. "SOCS, Inflammation, and Autoimmunity" *Front. Immunol.*, 2012, vol. 3, Article 20, 9 pages.

Zhang, J.G. et al. "The SOCS box of suppressor of cytokine signaling-1 is important for inhibition of cytokine action in vivo" *Proc. Natl. Acad. Sci. U.S.A.*, 2001, 98:13261-13265.

Zielinski, C.E. et al. "Naive CD4+ T cells from lupus-prone Fas-intact MRL mice display TCR-mediated hyperproliferation due to intrinsic threshold defects in activation" *J. Immunol.*, 2005, 174:5100-5109.

Waiboci, L.W. et al. "Both the suppressor of cytokine signaling 1 kinase inhibitory region and SOCS-1 mimetic bind to JAK2 autophosphorylation site: implications for the development of a SOCS-1 antagonist" *J. Immunol.*, Apr. 15, 2007, pp. 5058-5068.

Flowers, L.O. et al. "A SOCS-1 peptide mimetic inhibits both constitutive and IL-6 induced activation of STAT3 in prostate cancer cells" *Oncogene*, Mar. 17, 2005, vol. 24, No. 12, pp. 2114-2120.

(56) References Cited

OTHER PUBLICATIONS

Sharma, J. et al. "Suppressor of cytokine signaling-1 mimetic peptides attenuate lymphocyte activation in the MRL/lpr mouse autoimmune model" *Scientific Reports*, 2021, pp. 1-13, vol. 11, No. 6354.

* cited by examiner

```
                        SEQUENCE LISTING

<160> NUMBER OF SEQ ID NOS: 54

<210> SEQ ID NO 1
<211> LENGTH: 16
<212> TYPE: PRT
<213> ORGANISM: Artificial sequence
<220> FEATURE:
<223> OTHER INFORMATION: SOCS1-KIR peptide

<400> SEQUENCE: 1

Asp Thr His Phe Arg Thr Phe Arg Ser His Ser Asp Tyr Arg Arg Ile
1               5                   10                  15

<210> SEQ ID NO 2
<211> LENGTH: 16
<212> TYPE: PRT
<213> ORGANISM: Artificial sequence
<220> FEATURE:
<223> OTHER INFORMATION: SOCS1-KIR2A peptide

<400> SEQUENCE: 2

Asp Thr His Ala Arg Thr Ala Arg Ser His Ser Asp Tyr Arg Arg Ile
1               5                   10                  15

<210> SEQ ID NO 3
<211> LENGTH: 38
<212> TYPE: PRT
<213> ORGANISM: Artificial sequence
<220> FEATURE:
<223> OTHER INFORMATION: SOCS1-KIR dimer peptide

<400> SEQUENCE: 3

Asp Thr His Phe Arg Thr Phe Arg Ser His Ser Asp Tyr Arg Arg Ile
1               5                   10                  15

Gly Gly Gly Gly Gly Gly Asp Thr His Phe Arg Thr Phe Arg Ser His
                20                  25                  30

Ser Asp Tyr Arg Arg Ile
            35

<210> SEQ ID NO 4
<211> LENGTH: 38
<212> TYPE: PRT
<213> ORGANISM: Artificial sequence
<220> FEATURE:
<223> OTHER INFORMATION: SOCS1-KIR2A dimer peptide

<400> SEQUENCE: 4
```

Asp Thr His Ala Arg Thr Ala Arg Ser His Ser Asp Tyr Arg Arg Ile
1               5                   10                  15

Gly Gly Gly Gly Gly Asp Thr His Ala Arg Thr Ala Arg Ser His
            20                  25                  30

Ser Asp Tyr Arg Arg Ile
        35

<210> SEQ ID NO 5
<211> LENGTH: 20
<212> TYPE: PRT
<213> ORGANISM: Artificial sequence
<220> FEATURE:
<223> OTHER INFORMATION: amplification primer specific for SOCS1
      (forward)

<400> SEQUENCE: 5

Gly Ala Cys Ala Cys Thr Cys Ala Cys Thr Thr Cys Cys Gly Cys Ala
1               5                   10                  15

Cys Cys Thr Thr
        20

<210> SEQ ID NO 6
<211> LENGTH: 21
<212> TYPE: PRT
<213> ORGANISM: Artificial sequence
<220> FEATURE:
<223> OTHER INFORMATION: amplification primer specific for SOCS1
      (reverse)

<400> SEQUENCE: 6

Gly Ala Ala Gly Cys Ala Gly Thr Thr Cys Cys Gly Thr Thr Gly Gly
1               5                   10                  15

Cys Gly Ala Cys Thr
        20

<210> SEQ ID NO 7
<211> LENGTH: 20
<212> TYPE: PRT
<213> ORGANISM: Artificial sequence
<220> FEATURE:
<223> OTHER INFORMATION: amplification primer specific for beta-actin
      (forward)

<400> SEQUENCE: 7

Cys Cys Ala Cys Ala Gly Cys Ala Cys Thr Gly Thr Ala Gly Gly Gly
1               5                   10                  15

Thr Thr Thr Ala
        20

<210> SEQ ID NO 8
<211> LENGTH: 23
<212> TYPE: PRT
<213> ORGANISM: Artificial sequence
<220> FEATURE:
<223> OTHER INFORMATION: amplification primer specific for beta-actin
      (reverse)

<400> SEQUENCE: 8

Ala Thr Thr Gly Thr Cys Thr Thr Thr Cys Thr Cys Thr Gly Cys
1               5                   10                  15

Cys Gly Thr Thr Cys Thr Cys
        20

```
<210> SEQ ID NO 9
<211> LENGTH: 20
<212> TYPE: DNA
<213> ORGANISM: Mus musculus

<400> SEQUENCE: 9
ccttccttct tgggtatgga                                           20

<210> SEQ ID NO 10
<211> LENGTH: 20
<212> TYPE: DNA
<213> ORGANISM: Mus musculus

<400> SEQUENCE: 10
ggaggagcaa tgatcttgat                                           20

<210> SEQ ID NO 11
<211> LENGTH: 23
<212> TYPE: DNA
<213> ORGANISM: Mus musculus

<400> SEQUENCE: 11
aactatttta actcaagtgg cat                                       23

<210> SEQ ID NO 12
<211> LENGTH: 18
<212> TYPE: DNA
<213> ORGANISM: Mus musculus

<400> SEQUENCE: 12
aggtgtgatt caatgacg                                             18

<210> SEQ ID NO 13
<211> LENGTH: 18
<212> TYPE: DNA
<213> ORGANISM: Mus musculus

<400> SEQUENCE: 13
gggagaactt tgagtcca                                             18

<210> SEQ ID NO 14
<211> LENGTH: 17
<212> TYPE: DNA
<213> ORGANISM: Mus musculus

<400> SEQUENCE: 14
gaaggtcggg gtagaaa                                              17

<210> SEQ ID NO 15
<211> LENGTH: 17
<212> TYPE: DNA
<213> ORGANISM: Mus musculus

<400> SEQUENCE: 15
actctccacc gcaatga                                              17

<210> SEQ ID NO 16
<211> LENGTH: 17
<212> TYPE: DNA
<213> ORGANISM: Mus musculus

<400> SEQUENCE: 16
ctcttcagga ccaggat                                              17
```

```
<210> SEQ ID NO 17
<211> LENGTH: 22
<212> TYPE: DNA
<213> ORGANISM: Mus musculus

<400> SEQUENCE: 17
acagccactg cattcccagt tt                                              22

<210> SEQ ID NO 18
<211> LENGTH: 22
<212> TYPE: DNA
<213> ORGANISM: Mus musculus

<400> SEQUENCE: 18
tctcggaagg acttgcagac at                                              22

<210> SEQ ID NO 19
<211> LENGTH: 20
<212> TYPE: DNA
<213> ORGANISM: Mus musculus

<400> SEQUENCE: 19
gacactcact tccgcacctt                                                 20

<210> SEQ ID NO 20
<211> LENGTH: 20
<212> TYPE: DNA
<213> ORGANISM: Mus musculus

<400> SEQUENCE: 20
gaagcagttc cgttggcact                                                 20

<210> SEQ ID NO 21
<211> LENGTH: 19
<212> TYPE: DNA
<213> ORGANISM: Homo sapiens

<400> SEQUENCE: 21
tgcaccacca actgcttag                                                  19

<210> SEQ ID NO 22
<211> LENGTH: 18
<212> TYPE: DNA
<213> ORGANISM: Homo sapiens

<400> SEQUENCE: 22
gaggcaggga tgatgttc                                                   18

<210> SEQ ID NO 23
<211> LENGTH: 19
<212> TYPE: DNA
<213> ORGANISM: Homo sapiens

<400> SEQUENCE: 23
gggagcggat gggtgtagg                                                  19

<210> SEQ ID NO 24
<211> LENGTH: 21
<212> TYPE: DNA
<213> ORGANISM: Homo sapiens

<400> SEQUENCE: 24
agaggtagga ggtgcgagtt c                                               21
```

```
<210> SEQ ID NO 25
<211> LENGTH: 20
<212> TYPE: DNA
<213> ORGANISM: Homo sapiens

<400> SEQUENCE: 25
tgaccagagc atccaaaaga                                              20

<210> SEQ ID NO 26
<211> LENGTH: 20
<212> TYPE: DNA
<213> ORGANISM: Homo sapiens

<400> SEQUENCE: 26
ctcttcgacc tcgaaacagc                                              20

<210> SEQ ID NO 27
<211> LENGTH: 25
<212> TYPE: PRT
<213> ORGANISM: Artificial sequence
<220> FEATURE:
<223> OTHER INFORMATION: SOCS1-KIR peptide

<400> SEQUENCE: 27

Arg Arg Arg Arg Arg Arg Arg Arg Arg Asp Thr His Phe Arg Thr Phe
1               5                   10                  15

Arg Ser His Ser Asp Tyr Arg Arg Ile
            20                  25

<210> SEQ ID NO 28
<211> LENGTH: 25
<212> TYPE: PRT
<213> ORGANISM: Artificial sequence
<220> FEATURE:
<223> OTHER INFORMATION: SOCS1-KIR2A peptide

<400> SEQUENCE: 28

Arg Arg Arg Arg Arg Arg Arg Arg Arg Asp Thr His Ala Arg Thr Ala
1               5                   10                  15

Arg Ser His Ser Asp Tyr Arg Arg Ile
            20                  25

<210> SEQ ID NO 29
<211> LENGTH: 47
<212> TYPE: PRT
<213> ORGANISM: Artificial sequence
<220> FEATURE:
<223> OTHER INFORMATION: SOCS1-KIR dimer peptide

<400> SEQUENCE: 29

Arg Arg Arg Arg Arg Arg Arg Arg Arg Asp Thr His Phe Arg Thr Phe
1               5                   10                  15

Arg Ser His Ser Asp Tyr Arg Arg Ile Gly Gly Gly Gly Gly Asp
            20                  25                  30

Thr His Phe Arg Thr Phe Arg Ser His Ser Asp Tyr Arg Arg Ile
        35                  40                  45

<210> SEQ ID NO 30
<211> LENGTH: 47
<212> TYPE: PRT
<213> ORGANISM: Artificial sequence
<220> FEATURE:
<223> OTHER INFORMATION: SOCS1-KIR dimer peptide
```

```
<400> SEQUENCE: 30

Arg Arg Arg Arg Arg Arg Arg Arg Asp Thr His Ala Arg Thr Ala
1               5                   10                  15

Arg Ser His Ser Asp Tyr Arg Arg Ile Gly Gly Gly Gly Gly Asp
            20                  25                  30

Thr His Ala Arg Thr Ala Arg Ser His Ser Asp Tyr Arg Arg Ile
        35                  40                  45

<210> SEQ ID NO 31
<211> LENGTH: 15
<212> TYPE: PRT
<213> ORGANISM: Artificial sequence
<220> FEATURE:
<223> OTHER INFORMATION: cell-penetrating peptide PTD

<400> SEQUENCE: 31

Arg Gln Ile Lys Trp Phe Gln Asn Arg Arg Met Lys Trp Lys Lys
1               5                   10                  15

<210> SEQ ID NO 32
<211> LENGTH: 11
<212> TYPE: PRT
<213> ORGANISM: Artificial sequence
<220> FEATURE:
<223> OTHER INFORMATION: cell-penetrating peptide TAT

<400> SEQUENCE: 32

Tyr Gly Arg Lys Lys Arg Arg Gln Arg Arg Arg
1               5                   10

<210> SEQ ID NO 33
<211> LENGTH: 18
<212> TYPE: PRT
<213> ORGANISM: Artificial sequence
<220> FEATURE:
<223> OTHER INFORMATION: cell-penetrating peptide SynB1

<400> SEQUENCE: 33

Arg Gly Gly Arg Leu Ser Tyr Ser Arg Arg Arg Phe Ser Thr Ser
1               5                   10                  15

Gly Arg

<210> SEQ ID NO 34
<211> LENGTH: 10
<212> TYPE: PRT
<213> ORGANISM: Artificial sequence
<220> FEATURE:
<223> OTHER INFORMATION: cell-penetrating peptide SynB3

<400> SEQUENCE: 34

Arg Arg Leu Ser Tyr Ser Arg Arg Arg Phe
1               5                   10

<210> SEQ ID NO 35
<211> LENGTH: 12
<212> TYPE: PRT
<213> ORGANISM: Artificial sequence
<220> FEATURE:
<223> OTHER INFORMATION: cell-penetrating peptide PTD-4

<400> SEQUENCE: 35

Pro Ile Arg Arg Arg Lys Lys Leu Arg Arg Leu Lys
1               5                   10
```

```
<210> SEQ ID NO 36
<211> LENGTH: 12
<212> TYPE: PRT
<213> ORGANISM: Artificial sequence
<220> FEATURE:
<223> OTHER INFORMATION: cell-penetrating peptide PTD-5

<400> SEQUENCE: 36

Arg Arg Gln Arg Arg Thr Ser Lys Leu Met Lys Arg
1               5                   10

<210> SEQ ID NO 37
<211> LENGTH: 15
<212> TYPE: PRT
<213> ORGANISM: Artificial sequence
<220> FEATURE:
<223> OTHER INFORMATION: cell-penetrating peptide FHV Coat-(35-49)

<400> SEQUENCE: 37

Arg Arg Arg Arg Asn Arg Thr Arg Arg Asn Arg Arg Arg Val Arg
1               5                   10                  15

<210> SEQ ID NO 38
<211> LENGTH: 19
<212> TYPE: PRT
<213> ORGANISM: Artificial sequence
<220> FEATURE:
<223> OTHER INFORMATION: cell-penetrating peptide BMV Gag-(7-25)

<400> SEQUENCE: 38

Lys Met Thr Arg Ala Gln Arg Arg Ala Ala Ala Arg Arg Asn Arg Trp
1               5                   10                  15

Thr Ala Arg

<210> SEQ ID NO 39
<211> LENGTH: 13
<212> TYPE: PRT
<213> ORGANISM: Artificial sequence
<220> FEATURE:
<223> OTHER INFORMATION: cell-penetrating peptide HTLV-II Rex-(4-16)

<400> SEQUENCE: 39

Thr Arg Arg Gln Arg Thr Arg Arg Ala Arg Arg Asn Arg
1               5                   10

<210> SEQ ID NO 40
<211> LENGTH: 13
<212> TYPE: PRT
<213> ORGANISM: Artificial sequence
<220> FEATURE:
<223> OTHER INFORMATION: cell-penetrating peptide D-Tat

<400> SEQUENCE: 40

Gly Arg Lys Lys Arg Arg Gln Arg Arg Arg Pro Pro Gln
1               5                   10

<210> SEQ ID NO 41
<211> LENGTH: 13
<212> TYPE: PRT
<213> ORGANISM: Artificial sequence
<220> FEATURE:
<223> OTHER INFORMATION: cell-penetrating peptide R9-Tat

<400> SEQUENCE: 41

Gly Arg Arg Arg Arg Arg Arg Arg Arg Arg Pro Pro Gln
1               5                   10
```

```
<210> SEQ ID NO 42
<211> LENGTH: 27
<212> TYPE: PRT
<213> ORGANISM: Artificial sequence
<220> FEATURE:
<223> OTHER INFORMATION: cell-penetrating peptide Transportan

<400> SEQUENCE: 42

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 43
<211> LENGTH: 17
<212> TYPE: PRT
<213> ORGANISM: Artificial sequence
<220> FEATURE:
<223> OTHER INFORMATION: cell-penetrating peptide MAP

<400> SEQUENCE: 43

Lys Leu Ala Leu Lys Leu Ala Leu Lys Leu Ala Leu Ala Leu Lys Leu
1               5                   10                  15

Ala

<210> SEQ ID NO 44
<211> LENGTH: 27
<212> TYPE: PRT
<213> ORGANISM: Artificial sequence
<220> FEATURE:
<223> OTHER INFORMATION: cell-penetrating peptide SBP

<400> SEQUENCE: 44

Met Gly Leu Gly Leu His Leu Leu Val Leu Ala Ala Ala Leu Gln Gly
1               5                   10                  15

Ala Trp Ser Gln Pro Lys Lys Lys Arg Lys Val
            20                  25

<210> SEQ ID NO 45
<211> LENGTH: 27
<212> TYPE: PRT
<213> ORGANISM: Artificial sequence
<220> FEATURE:
<223> OTHER INFORMATION: cell-penetrating peptide FBP

<400> SEQUENCE: 45

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 46
<211> LENGTH: 27
<212> TYPE: PRT
<213> ORGANISM: Artificial sequence
<220> FEATURE:
<223> OTHER INFORMATION: cell-penetrating peptide MPG

<400> SEQUENCE: 46

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25
```

<210> SEQ ID NO 47
<211> LENGTH: 27
<212> TYPE: PRT
<213> ORGANISM: Artificial sequence
<220> FEATURE:
<223> OTHER INFORMATION: cell-penetrating peptide MPG(delta-NLS)

<400> SEQUENCE: 47

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 48
<211> LENGTH: 21
<212> TYPE: PRT
<213> ORGANISM: Artificial sequence
<220> FEATURE:
<223> OTHER INFORMATION: cell-penetrating peptide Pep-1

<400> SEQUENCE: 48

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 49
<211> LENGTH: 21
<212> TYPE: PRT
<213> ORGANISM: Artificial sequence
<220> FEATURE:
<223> OTHER INFORMATION: cell-penetrating peptide Pep-2

<400> SEQUENCE: 49

Lys Glu Thr Trp Phe Glu Thr Trp Phe Thr Glu Trp Ser Gln Pro Lys
1               5                   10                  15

Lys Lys Arg Lys Val
            20

<210> SEQ ID NO 50
<211> LENGTH: 12
<212> TYPE: PRT
<213> ORGANISM: Artificial sequence
<220> FEATURE:
<223> OTHER INFORMATION: Tkip peptide

<400> SEQUENCE: 50

Trp Leu Val Phe Phe Val Ile Phe Tyr Phe Phe Arg
1               5                   10

<210> SEQ ID NO 51
<211> LENGTH: 16
<212> TYPE: PRT
<213> ORGANISM: Artificial sequence
<220> FEATURE:
<223> OTHER INFORMATION: SOCS3-KIR peptide

<400> SEQUENCE: 51

Leu Arg Leu Lys Thr Phe Ser Ser Lys Ser Glu Tyr Gln Leu Val Val
1               5                   10                  15

<210> SEQ ID NO 52
<211> LENGTH: 38
<212> TYPE: PRT

```
<213> ORGANISM: Artificial sequence
<220> FEATURE:
<223> OTHER INFORMATION: SOCS3-KIR dimer peptide

<400> SEQUENCE: 52

Leu Arg Leu Lys Thr Phe Ser Ser Lys Ser Glu Tyr Gln Leu Val Val
1               5                   10                  15

Gly Gly Gly Gly Gly Gly Leu Arg Leu Lys Thr Phe Ser Ser Lys Ser
            20                  25                  30

Glu Tyr Gln Leu Val Val
        35

<210> SEQ ID NO 53
<211> LENGTH: 25
<212> TYPE: PRT
<213> ORGANISM: Artificial sequence
<220> FEATURE:
<223> OTHER INFORMATION: SOCS3-KIR peptide

<400> SEQUENCE: 53

Arg Arg Arg Arg Arg Arg Arg Arg Arg Leu Arg Leu Lys Thr Phe Ser
1               5                   10                  15

Ser Lys Ser Glu Tyr Gln Leu Val Val
            20                  25

<210> SEQ ID NO 54
<211> LENGTH: 47
<212> TYPE: PRT
<213> ORGANISM: Artificial sequence
<220> FEATURE:
<223> OTHER INFORMATION: SOCS3-KIR dimer peptide

<400> SEQUENCE: 54

Arg Arg Arg Arg Arg Arg Arg Arg Arg Leu Arg Leu Lys Thr Phe Ser
1               5                   10                  15

Ser Lys Ser Glu Tyr Gln Leu Val Val Gly Gly Gly Gly Gly Leu
            20                  25                  30

Arg Leu Lys Thr Phe Ser Ser Lys Ser Glu Tyr Gln Leu Val Val
        35                  40                  45
```

SOCS MIMETICS FOR THE TREATMENT OF DISEASES

CROSS-REFERENCE TO RELATED APPLICATIONS

The present application is the National Stage of International Application No. PCT/US2015/012760, filed Jan. 23, 2015, which claims the benefit of U.S. Provisional Application No. 61/931,363, filed Jan. 24, 2014, which is hereby incorporated by reference herein in its entirety, including any figures, tables, nucleic acid sequences, amino acid sequences, or drawings.

GOVERNMENT SUPPORT

This invention was made with government support under grant numbers R01 AI056152 and R01 NS051245 awarded by the National Institutes of Health. The government has certain rights in the invention.

BACKGROUND OF THE INVENTION

Systemic lupus erythematosus (SLE) is a multi-organ autoimmune disease with varied clinical manifestations, ranging from cutaneous pathologies to life threatening renal disease (reviewed in Tsokos 2011). Although auto-antibodies are critical to the pathogenesis of SLE, abnormal $CD4^+$ T cell responses make a key contribution, as $CD4^+$ T cell depletion in lupus-prone mouse models results in reduced anti-dsDNA IgG autoantibody production and prolonged survival (Wofsy et al. 1985; Santoro et al. 1988). Notably, although it is well accepted that dysregulated T lymphocyte effector functions are key to lupus onset and progression, how lupus-promoting T lymphocytes evade peripheral tolerance mechanisms is less well understood.

As a mechanism to maintain tolerance to ubiquitous self-antigens, naïve T lymphocytes typically require both TCR stimulation and co-stimulatory signals in order to obtain an activation threshold sufficient for clonal expansion and elaboration of effector functions (reviewed in Iannone and Lapadula 2012). Activation of the CD28 pathway is a critical naïve T lymphocyte co-stimulatory pathway, as it is typically responsible for the surface expression of the high affinity IL2R alpha chain (CD25) and the production of IL2, which are requisites for clonal expansion (Mondino and Jenkins 1994). Interactions between the TCR and antigen-MHC complexes, in the absence of co-stimulation, typically result in functional inactivation of naïve T lymphocyte clones and inhibition of a sustained immune response (reviewed in Tivol et al. 1996). Significantly, $CD4^+$ T lymphocytes obtained from SLE patients and murine disease models intrinsically possess a lower threshold of activation (Stekman et al. 1991; Desai-Mehta et al. 1996; Mohan et al. 1999; Vratsanos et al. 2001; Bouzahzah et al. 2003). Although it is known that lupus-promoting $CD4^+$ T lymphocytes possess a lower activation threshold, mechanistic insight into this pathogenic process is limited. Moreover, the therapeutic efficacy of treatment strategies, which target $CD4^+$ cell activation defects, remains inconclusive (Iannone and Lapadula 2012). A lower threshold of $CD4^+$ T lymphocyte activation is compounded by the observation that $CD4^+$ T cells in lupus have a preferential bias toward excessive type I and type II (IFNγ) interferon signaling (Takahashi et al. 1996; Balomenos et al. 1998). Notably suppressor of cytokine signaling-1 (SOCS1) critically regulates IFNγ (the sole type II interferon) (reviewed in Knosp and Johnston 2012) and type I interferon signaling (Piganis et al. 2011). SOCS1 is a member of a cytokine inducible family of intracellular proteins that is essential for the regulation of cytokine signaling and T lymphocyte effector functions (reviewed in Knosp and Johnston 2012). Although SOCS1 is critical in the regulation of IFNγ and type I interferon signaling, a defined role of SOCS1 in the prevention of human lupus pathology is less clear.

The binding of interferon molecules to ligand specific receptors results in a cascade of events in which Janus kinases (JAKs) are activated through phosphorylation, followed by activation and phosphorylation of signal transducing and activators of transcription (STAT) molecules (Platanias and Fish 1999; Kotenko and Pestka 2000). The STAT molecules then translocate to the nucleus where they mediate the transcription of interferon specific genes, which notably include SOCS1. SOCS1, which is also referred to as STAT induced STAT inhibitor-1, then inhibits the ability of the JAK molecules to mediate STAT activation thereby creating a classic feedback inhibition loop (reviewed in (Knosp and Johnston 2012)). Mice lacking the SOCS1 gene ($SOCS1^{-/-}$) develop a severe inflammatory disease, characterized by fatty degeneration of the liver, leukocyte infiltration into vital organs, and death within three weeks of birth (Alexander et al. 1999). This Src-homology type 2 (SH2) domain containing protein also possesses two functional domains: (i) the kinase inhibitory region (KIR), which inhibits JAK2 tyrosine kinase phosphorylation; and (ii) the SOCS box, which targets JAK associated cytokine receptors for lysosomal or proteosomal degradation (reviewed in Knosp and Johnston 2012). The KIR region of SOCS1 possesses significant immuno-regulatory properties, as transgenic mice that possess this functional domain, but lack the SOCS box, do not develop $SOCS1^{-/-}$ associated perinatal lethality (Zhang et al. 2001). Additionally, it has recently been shown that a SOCS1 mimetic peptide, corresponding to the KIR region of SOCS1 (SOCS1-KIR), has potent regulatory capacity both in vitro and in vivo (Jager et al. 2011; Collins et al. 2011). Although SOCS1 is essential for the regulation of immune events that are associated with lupus onset and progression, strategies to target the SOCS1 regulatory pathway as a lupus therapeutic are limited.

It has recently been shown that, upon disease onset, splenocytes from $(NZB \times NZW)F_1$ mice, a classic model of SLE, display enhanced STAT1 activation and reduced SOCS1 expression (Sharabi et al. 2009). Moreover, treatment of this mouse model with the tolerogenic peptide, hCDR1, increased SOCS1 expression and ameliorated lupus disease (Sharabi et al. 2009). Notably, $SOCS1^{+/-}$ mice, which possess one functional allele of SOCS1, develop disease symptoms similar to human lupus, including anti-dsDNA auto-antibody production and glomerulonephritis at greater than 6 months of age (Fujimoto et al. 2004). Though murine studies clearly show an association between reduced SOCS1 expression and increased disease pathology, the exact mechanisms by which SOCS1 deficiency leads to murine lupus development have not been elucidated.

BRIEF SUMMARY OF THE INVENTION

The subject invention concerns peptide mimetics of SOCS proteins and methods of use. In one embodiment, a peptide mimetic of the invention binds to a SOCS1 and a SOCS3 target protein. In a specific embodiment, a peptide mimetic of the invention comprises the amino acid sequence of SEQ ID NO:1 and/or SEQ ID NO:2 and/or SEQ ID NO:51, or a functional fragment or variant thereof. In a further embodiment, a peptide of the invention can comprise multiple copies of the mimetic sequence. In one embodiment, a peptide of the invention comprises two or more copies of SEQ ID NO:1 and/or SEQ ID NO:2 and/or SEQ ID NO:51. In a specific embodiment, a peptide mimetic of the invention comprises the amino acid sequence of SEQ ID NO:3 and/or SEQ ID NO:4 and/or SEQ ID NO:52, or a functional fragment or variant thereof.

The subject invention also pertains to methods of treating and/or preventing autoimmune conditions and/or disorders. In one embodiment, one or more peptide mimetics of the invention are used to treat an autoimmune condition or disorder in a person or animal. In a specific embodiment, a mimetic of the invention is used to treat SLE or multiple sclerosis (MS) in a person or animal. In another embodiment, a peptide mimetic of the invention is used to treat an autoimmune skin disorder, such as psoriasis. In a specific embodiment, a peptide mimetic of the invention comprises the amino acid sequence of SEQ ID NO:1 and/or SEQ ID NO:2 and/or SEQ ID NO:51, or a functional fragment or variant thereof. In a further embodiment, a peptide of the invention can comprise multiple copies of the mimetic sequence. In one embodiment, a peptide of the invention comprises two or more copies of SEQ ID NO:1 and/or SEQ ID NO:2 and/or SEQ ID NO:51. In a specific embodiment, a peptide mimetic of the invention comprises the amino acid sequence of SEQ ID NO:3 and/or SEQ ID NO:4 and/or SEQ ID NO:52, or a functional fragment or variant thereof.

We show herein that lupus free, SOCS1$^{+/-}$ mice possess an increased proportion of peripheral CD4$^+$ T cells bearing an activated cell phenotype. Through in vitro analysis, we show that CD28 signaling and subsequent Akt phosphorylation are dispensable for SOCS1$^{+/-}$ CD4$^+$ T lymphocyte activation. Therefore, these SOCS1 deficient cells possess a lower activation threshold. We also demonstrate that naïve SOCS1$^{+/-}$ cells, which are biased toward a Th1 phenotype, can readily undergo regulatory T cell differentiation, but are biased against Th17 differentiation. Additionally, we show that a mimetic peptide of the SOCS1 kinase inhibitory region, SOCS-KIR, has the capacity to inhibit excessive CD4$^+$ T cell activation, proliferation, and IFNγ signaling. Finally, we demonstrate that peripheral blood mononuclear cells (PBMCs) from SLE patients have reduced SOCS1 expression, which is correlated with SLE disease activity-associated markers, type I IFN signature and serum complement component 3 (C3) levels.

BRIEF DESCRIPTION OF THE DRAWINGS

The patent or application file contains at least one drawing executed in color. Copies of this patent or patent application publication with color drawing(s) will be provided by the Patent and Trademark Office upon request and payment of the necessary fee.

(FIG. 1A) SOCS1$^{+/+}$ or SOCS1$^{+/-}$ CD4$^+$CD8$^-$ thymocyte frequency was assessed by flow cytometry (left). Flow diagrams are representative of 9 independent experiments, which are presented graphically in the middle. Absolute CD4$^+$CD8$^-$ cell counts were calculated from each experiment and are presented on the right. (FIG. 1B) LNs and spleen from SOCS1$^{+/+}$ or SOCS1$^{+/-}$ mice were pooled and CD4$^+$ frequency was assessed by flow cytometry (left). Flow diagrams are representative of 8 independent experiments, which are presented graphically in the middle. Absolute CD4$^+$ cell counts were calculated from each experiment and are presented on the right. (FIG. 1C) SOCS1$^{+/+}$ or SOCS1$^{+/-}$ CD4$^+$CD25$^+$ and CD4$^+$CD69$^+$ T cell frequencies within pooled LNs and spleen were assessed by flow cytometry (left). Flow diagrams are representative of 9 independent experiments, which are presented graphically in the middle. Absolute CD4$^+$CD25$^+$ and CD4$^+$CD69$^+$ cell counts were calculated from each experiment and are presented on the right. Results are shown as mean±s.e.m. Statistical comparisons were performed using the Mann-Whitney U test (*P<0.05).

(FIG. 2A) The frequencies of CD25 and CD69 expressing cells were assessed by flow cytometry. Flow cytometry histograms are representative of 4 independent experiments. (FIG. 2B) Proliferation was assessed by CFSE labeling (top), cell counts (middle), and $^3$[H] thymidine incorporation (bottom). Flow cytometry graphs to assess CFSE labeling are representative of 4 independent experiments. (FIG. 2C) pAkt and Akt proteins were assessed by western blotting (top). pAkt relative intensities are displayed graphically (bottom). Blots and graphs are representative of 4 independent experiments. (FIG. 2D) IFNγ secretion was measured by ELISA (n=3). Results are shown as mean±s.e.m. Statistical comparisons were performed using the Mann-Whitney U test (*P<0.05, ***P<0.0005). αCD3=anti-CD3, αCD28=anti-CD28, WT=SOCS1$^{+/+}$, HT=SOCS1$^{+/-}$.

(FIG. 3A) Naïve SOCS1$^{+/+}$ or SOCS1$^{+/-}$ CD4$^+$CD25$^-$ T cells were placed under control (αCD3, αCD28) or Treg inducing conditions for 3 d and Foxp3 expression was measured by intracellular staining and flow cytometry. Histograms on the left are representative of 4 independent experiments, which are displayed graphically on the right. (FIG. 3B) Naïve SOCS1$^{+/+}$ or SOCS1$^{+/-}$ CD4$^+$CD25$^-$ T cells were placed under control or Th17 inducing conditions for 5 d. IL-17A expression was measured by intracellular staining and flow cytometry. Histograms on the left are representative of 10 independent experiments, which are shown graphically on the right. (FIG. 3C) IL-17a and RORγt mRNA expression were measured by qPCR (left and right, respectively) and IL-17A secretion was assessed by ELISA (middle). Graphs of IL-17A qPCR and ELISA are representative of 10 independent experiments and graph of RORγt qPCR is representative of 5 independent experiments. (FIGS. 3D and 3E) Naïve SOCS1$^{+/+}$or SOCS1$^{+/-}$ CD4$^+$CD25$^-$ T cells were CFSE labeled and were placed under the indicated conditions for 3d in FIG. 3D and 5 d in FIG. 3E. Cell proliferation and Foxp3 expression (FIG. 3D) or IL-17A expression (FIG. 3E) were measured by flow cytometry. Flow diagrams in (FIG. 3D) and (FIG. 3E) are representative of 5 experiments. Results are shown as mean±s.e.m. Statistical comparisons were performed using the Mann-Whitney U test (***P<0.0005). iTh17=Th17 inducing conditions. IL-17a and RORγt expression is relative to β-actin.

(FIGS. 4A and 4B) SOCS1$^{+/+}$ or SOCS1$^{+/-}$ CD4$^+$CD25$^-$ T cells were placed under Th17 inducing conditions or left unstimulated for 5 d. (FIG. 4A) IFNγ and Tbet expression were assessed by qPCR (n=4). (FIG. 4B) IFNγ$^+$ cells were assessed by intracellular staining and flow cytometry. Flow diagrams are representative of 4 independent experiments. (FIG. 4C) IFNγ$^+$ and/or IL-17A+ cells were assessed as in (FIG. 4B). Flow diagrams are representative of 4 independent experiments. (FIG. 4D) Frequencies of IL-17A producing cells were identified by intracellular staining and flow cytometry following Th17 induction of SOCS1$^{+/+}$, SOCS1$^{+/-}$, or SOCS1$^{+/-}$IFN$\gamma^{-/-}$ CD4$^+$CD25$^-$ T cells. Results are representative of 4 independent experiments. Results are shown as mean±s.e.m. Statistical comparisons were performed using the Mann-Whitney U test (*P<0.05). iTh17=Th17 inducing conditions. IFN$\gamma$ and T-bet expression is relative to $\beta$-actin.

(FIGS. 5A and 5B) SOCS1$^{+/+}$ or SOCS1$^{+/-}$ CD4$^+$CD25$^-$ T cells were stimulated with $\alpha$CD3 antibodies alone or with $\alpha$CD3+SOCS1-KIR peptide (20 $\mu$M) for 72 h. (FIG. 5A) CD25 expressing cells were assessed by flow cytometry. Results are representative of 4 independent experiments. (FIG. 5B) Proliferation was assessed by CFSE labeling and flow cytometry, cell counts, and $^3$[H] thymidine incorporation. n=4. (FIGS. 5C and 5D) SOCS1$^{+/+}$ or SOCS1$^{+/-}$ CD4$^+$CD25$^-$ T cells were placed under Th17 inducing conditions in the absence or presence of SOCS1-KIR peptide (20 $\mu$M) (FIG. 5C) IFN$\gamma$ expression, relative to $\beta$-actin., was assessed by qPCR (left) and ELISA (right) (n=4). (FIG. 5D) pSTAT1 and STAT1 protein expressions were assessed by western blotting. Results are representative of 4 independent experiments. Statistical comparisons were performed using Mann-Whitney U test. (*P<0.05). iTh17=Th17 inducing conditions, WT=SOCS1$^{+/+}$, and HT=SOCS1$^{+/-}$.

(FIG. 6A) PMBCs were isolated from whole blood taken from SLE patients or healthy controls and SOCS1 was measured via qPCR, relative to GAPDH. (FIG. 6B) For each patient, SOCS1 expression was correlated with IFN$\gamma$ expression (left) and monocyte CD64 MFI (right). (FIG. 6C) SOCS1 expression in patients was also correlated with C3 levels (left) and C4 levels (right). Results shown as mean±s.e.m. Statistical comparisons between healthy controls and SLE patients were performed using the Mann-Whitney U test (**P<0.005). Spearman's correlation was chosen for statistical analyses in (FIG. 6B) and (FIG. 6C). MFI=Mean Fluorescent intensity.

(FIG. 7A) Concentrations of total IgG antibodies and IgG autoantibodies specific for ssDNA and dsDNA antigens in SOCS1$^{+/+}$ or SOCS$^{+/-}$ mice, <6 months of age, were measured by ELISA. (FIG. 7B) Proteinuria was assessed in SOCS1$^{+/+}$ and SOCS1$^{+/-}$ mice, <6 months of age. (FIG. 7C) Schematic timeline for autoantibody production by SOCS1$^{+/-}$ mice and display of age range of SOCS1$^{+/+}$ and SOCS1$^{+/-}$ mice chosen for experiments. Results are shown as mean±s.e.m. Statistical comparisons were performed using the Mann-Whitney U test.

(FIG. 9A) PBMCs, taken from healthy controls, were treated with (FIG. 9A) chloroquine diphosphate salt at the indicated molar concentrations for 12 and 24 h or (FIG. 9B) dexamethasone at the indicated molar concentrations for 3, 6, 12, or 24 h. Post treatment, SOCS1 expression, relative to GAPDH, was assessed via qPCR. Results shown as mean±s.e.m. The Kruskal-Wallis test followed by the Dunn's Multiple Comparison Test was chosen to assess statistical significance. (*P<0.05).

(FIG. 10A) SOCS1 expression was compared between age-matched HCs and SLE patients. (FIG. 10B) SOCS1 expression in SLE patients was correlated with the SLE disease activity index (SLEDAI). Spearman's correlation was chosen for statistical analyses.

(FIG. 12A) Schematic showing time frame in which lupus pathology occurs in SOCS1+/- mice. (FIG. 12B) Model showing regulation of the Th1/IFN gamma pathway by SOCS1 (depicted from Egwuagu and Larkin, 2013). (FIG. 12C) Graph showing relative expression of SOCS1 in spleen taken from SOCS1+/+ (wild-type) and SOCS1+/- mice.

(FIGS. 13A and 13B) SOCS1$^{+/+}$ or SOCS1$^{+/-}$, CD4$^+$CD25$^-$ T cells were stimulated with $\alpha$CD3 antibodies alone or with $\alpha$CD3+SOCS1-KIR peptide for 72 h. (FIG. 13A) Proliferation was assessed by CFSE labeling and flow cytometry. (FIG. 13B) CD25 expressing cells were assessed by flow cytometry. (FIG. 13C) SOCS1$^{+/+}$ or SOCS1$^{+/-}$, CD4$^+$CD25$^-$ T cells were treated under the indicated conditions in the absence or presence of SOCS1-KIR peptide followed by analysis of pSTAT1 and STAT1 protein expressions by western blotting. Results are representative of ≥3 independent experiments. Statistical comparisons were performed using Mann-Whitney U test. (*P<0.05). Th17=Th17 inducing conditions, WT=SOCS1$^{+/+}$ and HT=SOCS1$^{+/-}$.

(FIG. 15A) Kaplan Meier curve showing survival of SOCS1$^{-/-}$ (black square; n=7) or CD4$^+$/SOCS1-KIR treatment (purple triangles, n=12). Numbers of mice in each group are indicated in parentheses. Mice were euthanized when moribund with survival comparisons by Mantel-Cox. Statistical significance denoted by asterisks. (FIG. 15B) Photographs of H &

E stains depicting heart and liver tissues of 2 week old SOCS1$^{-/-}$, SOCS1$^{-/-}$ mice receiving dual treatments, or littermate control mice. Photographs shown of H & E stained liver and heart of untreated SOCS1$^{-/-}$ (N=8) and WT (N=7) mice are representative of 100% of samples analyzed. Photographs shown of H & E stained liver and heart of SOCS1$^{-/-}$ mice receiving combined treatments are representative of 2 out of 5 mice in regard to heart samples and 1 out of 5 mice in regards to liver tissue. (FIG. 15C) Graph showing average daily weights of SOCS1$^{-/-}$ mice untreated (n=16), CD4$^+$/SOCS1-KIR treatment (n=12), or WT littermate controls (n=9) over a two week period. (FIG. 15D) Photographs of 2 week old SOCS1$^{-/-}$ mice, SOCS1$^{-/-}$ mice receiving dual treatment, and WT littermate controls. (FIG. 15E) Graphs showing IFNg levels within the sera of 2 week old WT (n=7) or SOCS1$^{-/-}$ mice with (n=8) and without (n=10) CD4$^+$/SOCS1-KIR treatment, measured by ELISA. (FIG. 15F) Graphs showing absolute numbers of CD4$^+$ Foxp3$^+$ lymphocytes present in two week old SOCS1$^{-/-}$ and WT littermate control mice with or without CD4$^+$/SOCS1-KIR treatment and WT 6-8 week old adult mice. Each dot is representative of an individual mouse with averages denoted by lines. Statistics were performed using unpaired, two-tailed t test comparing treated SOCS1$^{-/-}$ to untreated SOCS1$^{-/-}$ 2 wk. Statistical significance is denoted by asterisks. *, p≤0.05; , p 0≤0.005; *, p≤0.0005.

(FIG. 16A) Graphs showing average SOCS1 and SOCS3 mRNA expression (mean±SE) via real time RT-PCR, relative to GAPDH in SLE patients (N=33) versus controls (N=11) (FIG. 16B). Simple linear regression correlating SOCS1 vs SOCS3 gene expression at the 95% confidence level within SLE patients. Correlation was considered significant at 0.05 level (2 tailed). (FIG. 16C) Graph showing average SOCS1 and SOCS3 protein levels (arbitrary Units mean±SE) within SLE patients (N=32) compared to controls (N=6). (FIG. 16D) Individual basal protein level comparisons between SOCS1 and SOCS3 within SLE patients. The mean values of healthy controls (n=6) are represented as solid red circles with the values of individual SLE patients being represented as respective black dotted lines. (FIG. 16E) Western blot analysis of SOCS1, SOCS3, pAKT, pERK1/2 and pSTAT1 in human SLE patients (N=32) and healthy controls (N=6) relative to loading control GAPDH. *represents significant Pearson correlation; ˆ represents a t-test with significant mean difference. Correlation was considered significant at 0.05 level (2 tailed).

(FIG. 17A) Graphical representation (arbitrary Units mean±SE) of pAKT and AKT; pERK1/2 and ERK1/2; pSTAT1 and STAT1 protein levels of SLE patients (N=32) as compared to controls (N=6). (FIG. 17B) Individual basal level comparison of SOCS1 to phosphorylated proteins (pAKT; pERK1/2; pSTAT1) from individual SLE patients (N=32) that are represented as solid black circles. (FIG. 17C) Represents the individual basal level comparison of SOCS3 to phosphorylated proteins (pAKT; pERK1/2; pSTAT1) of individual SLE patients (N=32). The mean values of healthy controls (n=6) are represented as solid red circles and the means for SLE patients are represented as black dotted line respectively. *represents significant Pearson correlation; ˆ represents a t-test with significant mean difference. Correlation was considered significant at 0.05 level (2 tailed).

(FIG. 18A) Graph showing pSTAT1/SOCS1 ratios (from FIG. 17B) bearing a distinctly positive of negative of slope, where each number denotes an individual patient. (dotted line denotes location where slope=1). (FIG. 18B) Graphical representation comparing MHC class 1 message levels (HLA-HQ-DQR and HQ-DAR) in patients bearing high versus low pSTAT1/SOCS1 ratio, showing an inverted SOCS1/pSTAT1 ratio in protein levels correlated to significantly enhanced MHC class I message levels amongst SLE patients.

(FIG. 19A) IFNγ and IL-27 mRNA expression was measured (mean±SE) via real time RT-PCR, relative to GAPDH in SLE patients (N=33) and controls (N=11). (FIG. 19B) Simple linear regressions correlating IFNγ mRNA expression with SOCS1 and SOCS3 mRNA and protein expression in SLE patients at 95% confidence level. to (FIG. 19C) Simple linear regressions correlating IL-27 mRNA expression with SOCS1 and SOCS3 mRNA and protein expression in SLE patients with 95% confidence level. to (FIG. 19D) Simple linear regressions correlating CD64 (MFI) with SOCS1 and SOCS3 gene and protein expression were achieved for SLE patients to with 95% confidence level. *represents significant Pearson correlation; ˆ represents a t-test with significant mean difference. Correlation was considered significant at 0.05 level (2 tailed).

BRIEF DESCRIPTION OF THE SEQUENCES

Figure 1:
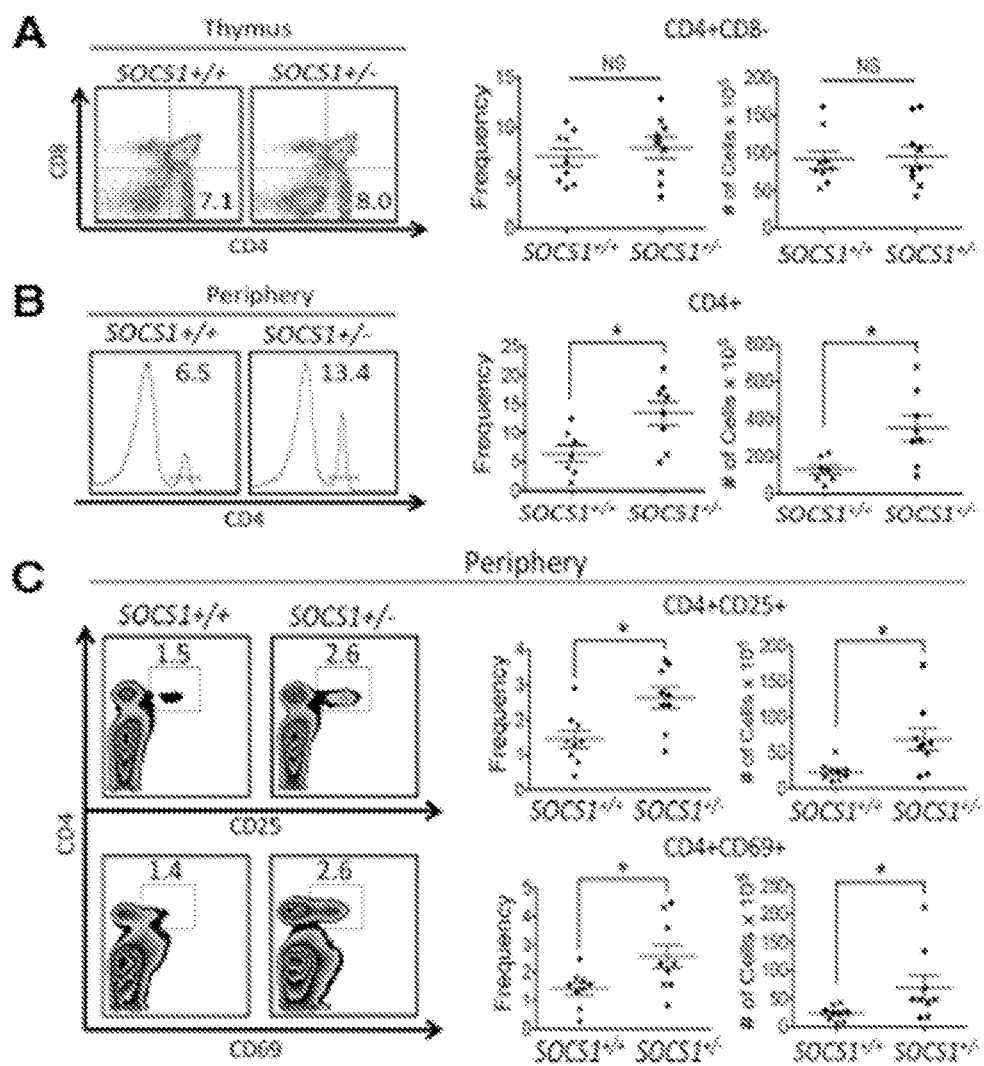
FIGS. 1A-1C. SOCS1$^{+/-}$ mice exhibit CD4$^+$ T cell accumulation and enhanced CD4$^+$ T cell activation in the periphery.

SEQ ID NO:1 ($^{53}$DTHFRTFRSHSDYRRI) is one embodiment of a SOCS1-KIR peptide of the present invention.

SEQ ID NO:2 ($^{53}$DTHARTARSHSDYRRI) is one embodiment of a SOCS1-KIR2A peptide of the present invention.

SEQ ID NO:3 ($^{53}$DTHFRTFRSHSDYR-RIGGGGGGDTHFRTFRSHSDYRRI) is one embodiment of a SOCS1-KIR dimer peptide of the present invention.

SEQ ID NO:4 (DTHARTARSHSDYR-RIGGGGGGDTHARTARSHSDYRRI) is one embodiment of a SOCS1-KIR2A dimer peptide of the present invention.

SEQ ID NOs:5-26 are amplification primers.

SEQ ID NO:27 (RRRRRRRRRDTHFRTFRSHSDYRRI) is one embodiment of a SOCS1-KIR peptide of the present invention.

SEQ ID NO:28 (RRRRRRRRRDTHARTAR-SHSDYRRI) is one embodiment of a SOCS1-KIR2A peptide of the present invention.

SEQ ID NO:29: (RRRRRRRRRDTHFRTFRSHSDYR-RIGGGGGGDTHFRTFRSHSDYRRI) is one embodiment of a SOCS1-KIR dimer peptide of the present invention.

SEQ ID NO:30: (RRRRRRRRRDTHARTARSHSDYR-RIGGGGGGDTHARTARSHSDYRRI) is one embodiment of a SOCS1-KIR2A dimer peptide of the present invention.

SEQ ID NOs:31-49 are examples of cell penetrating peptides that can be used with the present invention.

SEQ ID NO:50 (WLVFFVIFYFFR) is one embodiment of a Tkip peptide of the present invention.

SEQ ID NO:51 (LRLKTFSSKSEYQLVV) is one embodiment of a SOCS3-KIR peptide of the present invention.

SEQ ID NO:52 (LRLKTFSSKSEYQLVVGGGGG-GLRLKTFSSKSEYQLVV) is one embodiment of a SOCS3-KIR dimer peptide of the present invention.

SEQ ID NO:53 (RRRRRRRRRLRLKTFSSK-SEYQLVV) is one embodiment of a SOCS3-KIR peptide of the present invention.

SEQ ID NO:54: (RRRRRRRRRLRLKTFSSKSEYQLVVGGGGG-GLRLKTFSSKSEYQLVV) is one embodiment of a SOCS3-KIR dimer peptide of the present invention.

DETAILED DESCRIPTION OF THE INVENTION

The subject invention concerns peptide mimetics of SOCS proteins and methods of use. In one embodiment, a peptide mimetic of the invention binds to a SOCS1 and a SOCS3 tyrosine kinase target protein. In one embodiment, a peptide mimetic of the invention binds to a JAK2 and TYK2 tyrosine kinase. In a specific embodiment, a peptide mimetic of the invention comprises the amino acid sequence of SEQ ID NO:1 or SEQ ID NO:2 or SEQ ID NO:51, or a functional fragment or variant thereof. In a further embodiment, a peptide of the invention can comprise multiple copies of the mimetic sequence. In one embodiment, a peptide of the invention comprises two or more copies of SEQ ID NO:1 or SEQ ID NO:2 or SEQ ID NO:51. In a specific embodiment, a peptide mimetic of the invention comprises the amino acid sequence of SEQ ID NO:3 or SEQ ID NO:4 or SEQ ID NO:52, or a functional fragment or variant thereof.

The subject invention also pertains to methods of treating and/or preventing autoimmune conditions and/or disorders. In one embodiment, one or more peptide mimetics or polynucleotides of the invention, or a composition comprising one or more of the peptide mimetics or polynucleotides, are used to treat an autoimmune condition or disorder in a person or animal by administering an effective amount of a mimetic peptide or composition of the invention to the person or animal. In a specific embodiment, a mimetic of the invention is used to treat MS or SLE in a person or animal. In another embodiment, a mimetic of the invention is used to treat an autoimmune skin disorder, such as psoriasis. In a specific embodiment, a peptide mimetic used with a method of the invention comprises the amino acid sequence of SEQ ID NO:1 or SEQ ID NO:2 or SEQ ID NO:51, or a functional fragment or variant thereof. In a further embodiment, a peptide used with a method of the invention can comprise multiple copies of the mimetic sequence. Peptides with multiple copies of a mimetic sequence can optionally comprise one or more linker amino acids between the mimetic sequences. In one embodiment, the linker amino acid is glycine. In one embodiment, a peptide used with a method of the invention comprises two or more copies of SEQ ID NO:1 or SEQ ID NO:2 or SEQ ID NO:51. In a specific embodiment, a peptide mimetic used with a method of the invention comprises the amino acid sequence of SEQ ID NO:3 or SEQ ID NO:4 or SEQ ID NO:52, or a functional fragment or variant thereof.

The subject invention also pertains to methods of treating and/or preventing disorders and/or conditions associated with activated tyrosine kinases in a person or animal by administering an effective amount of one or more mimetic peptide, polynucleotide, or composition of the invention to the person or animal. In one embodiment, the tyrosine kinase is a JAK kinase. In a specific embodiment, the JAK kinase is JAK2 kinase. In a specific embodiment, a peptide mimetic used with a method of the invention comprises the amino acid sequence of SEQ ID NO:1 or SEQ ID NO:2 or SEQ ID NO:51, or a functional fragment or variant thereof. In a further embodiment, a peptide used with a method of the invention can comprise multiple copies of the mimetic sequence. In one embodiment, a peptide used with a method of the invention comprises two or more copies of SEQ ID NO:1 or SEQ ID NO:2 or SEQ ID NO:51. In a specific embodiment, a peptide mimetic used with a method of the invention comprises the amino acid sequence of SEQ ID NO:3 or SEQ ID NO:4 or SEQ ID NO:52, or a functional fragment or variant thereof.

The subject invention also pertains to methods of treating and/or preventing neurological disorders and/or conditions that have an inflammatory component associated with them by administering an effective amount of one or more mimetic peptide, polynucleotide, or composition of the invention. In one embodiment, a peptide mimetic of the invention is used to treat Parkinson's disease or ALS. In a specific embodiment, a peptide mimetic used with a method of the invention comprises the amino acid sequence of SEQ ID NO:1 or SEQ ID NO:2 or SEQ ID NO:51, or a functional fragment or variant thereof. In a further embodiment, a peptide used with a method of the invention can comprise multiple copies of the mimetic sequence. In one embodiment, a peptide used with a method of the invention comprises two or more copies of SEQ ID NO:1 or SEQ ID NO:2 or SEQ ID NO:51. In a specific embodiment, a peptide mimetic used with a method of the invention comprises the amino acid sequence of SEQ ID NO:3 or SEQ ID NO:4 or SEQ ID NO:52, or a functional fragment or variant thereof.

In one embodiment, a peptide of the invention comprises a lipophilic sequence or moiety that facilitates penetration through a cell membrane for entry into a cell. In one embodiment, a peptide of the invention comprises one or more arginine and/or lysine amino acids at one or both termini of the peptide. In a specific embodiment, a peptide of the invention comprises one or more arginine amino acids at the N-terminus of the peptide. For example, a peptide can comprise 1, 2, 3, 4, 5, 6, 7, 8, 9, 10, or more arginine and/or lysine amino acids at one or both termini. In an exemplified embodiment, a peptide of the invention has the amino acid sequence shown in SEQ ID NO:27, SEQ ID NO:28, SEQ ID NO:29, SEQ ID NO:30, SEQ ID NO:52, or SEQ ID NO:54. In another embodiment, a peptide of the invention comprises a fatty acid moiety, e.g., a carboxylic acid with a long aliphatic tail, attached to the peptide. Examples of fatty acids contemplated within the scope of the invention include, but are not limited to, caprylic acid, capric acid, lauric acid, myristic acid, palmitic acid, stearic acid, arachidic acid, behenic acid, lignoceric acid, and cerotic acid. In a specific embodiment, a peptide of the invention comprises a palmitate or palmitic acid (hexadecanoic acid) attached to the peptide, typically at the N- and/or C-terminus of the peptide. In a further embodiment, a peptide of the invention comprises a nuclear localization sequence (NLS).

As those skilled in the art can readily appreciate, there can be a number of variant sequences of a protein found in nature, in addition to those variants that can be artificially created by the skilled artisan in the lab. The peptides of the subject invention encompasses those specifically exemplified herein, as well as any natural variants thereof, as well as any variants which can be created artificially, so long as those variants retain the desired biological activity.

The peptides contemplated in the subject invention include the specific peptides exemplified herein as well as equivalent peptides which may be, for example, somewhat longer or shorter than the peptides exemplified herein. For example, using the teachings provided herein, a person skilled in the art could readily make peptides having from 1 to about 5, 10, 15, 20, 25, 30, 35, 40, 50, 60, 70 or more amino acids added to, or removed from, either end of the disclosed peptides using standard techniques known in the art. In one embodiment, amino acids are removed from the N-terminus of a peptide of the invention. In a specific embodiment, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70 or more amino acids can, independently, be removed from either or both ends of a peptide of the invention. Preferably, any added amino acids would be the same as the corresponding amino acids of a mature full-length SOCS protein. The skilled artisan, having the benefit of the teachings disclosed in the subject application, could easily determine whether a variant peptide retained the biological activity of the specific peptides exemplified herein. Such a longer or shorter peptide would be within the scope of the subject invention as long as said peptide does not encompass the entire full-length SOCS protein and said longer or shorter peptide retains substantially the same relevant biological activity as the peptides exemplified herein. For example, a longer or shorter variant of the SOCS1-KIR (SEQ ID NO:1) or SOCS1-KIR2A (SEQ ID NO:2) or SOCS3-KIR (SEQ ID NO:51) peptide would fall within the scope of the subject invention if the variant peptide had the ability to mimic SOCS function, e.g., bind to the activation loop of a tyrosine kinase.

Also within the scope of the subject invention are peptides which have the same amino acid sequences of a peptide exemplified herein except for amino acid substitutions, additions, or deletions within the sequence of the peptide, as long as these variant peptides retain substantially the same relevant biological activity as the peptides specifically exemplified herein. For example, conservative amino acid substitutions within a peptide which do not affect the ability of the peptide to, for example, to mimic SOCS1 function would be within the scope of the subject invention. Thus, the peptides disclosed herein should be understood to include variants and fragments, as discussed above, of the specifically exemplified sequences.

The subject invention further includes polynucleotides comprising nucleotide sequences which encode the peptides disclosed herein. In one embodiment, a polynucleotide comprises a nucleotide sequence which encodes a peptide comprising one or more of the amino acid sequences of SEQ ID NO:1, 2, 3, 4, 27, 28, 29, 30, 51, 52, 53, or 54. These nucleotide sequences can be readily constructed by those skilled in the art having the knowledge of the protein and peptide amino acid sequences which are presented herein. As would be appreciated by one skilled in the art, the degeneracy of the genetic code enables the artisan to construct a variety of nucleotide sequences that encode a particular peptide or protein. The choice of a particular nucleotide sequence could depend, for example, upon the codon usage of a particular expression system.

The subject invention contemplates the use of the peptides described herein in pharmaceutical compositions for administration to an animal or human for the treatment of clinically important disease conditions that are amenable to treatment with a full-length SOCS protein. For example, using the teachings described herein, the skilled artisan can use the subject invention to modulate the immune response of an animal or human. The peptides of the subject invention can be prepared in pharmaceutically acceptable carriers or diluents for administration to humans or animals in a physiologically tolerable form. Materials and methods for preparing such compositions are known in the art.

The peptides of the subject invention can be administered using a variety of techniques that are known in the art. In one embodiment, one or more peptides of the invention are administered as a topical preparation to the skin or an external membrane of a person or animal. The peptides can be encapsulated in liposomes that are targeted to specific cells or tissues and the liposome-encapsulated peptides delivered to the cells or tissue either in vitro, in vivo, or ex vivo. Procedures for preparing liposomes and encapsulating compounds within the liposome are well known in the art. See, for example, U.S. Pat. No. 5,252,348, which issued to Schreier et al. Peptides can also be conjugated or attached to other molecules, such as an antibody, that targeted a specific cell or tissue. Peptides can also be administered using a drug delivery system similar to that described in U.S. Pat. No. 4,625,014, which issued to Senter et al.

A further aspect of the claimed invention is the use of the claimed peptides to produce antibodies, both polyclonal and monoclonal. These antibodies can be produced using standard procedures well known to those skilled in the art. These antibodies may be used as diagnostic and therapeutic reagents. For example, antibodies that bind to the SOCS1-KIR (SEQ ID NO:1) peptide can be used as an antagonist to block the function of SOCS protein. Antibodies that are reactive with the peptides of the subject invention can also be used to purify SOCS protein from a crude mixture.

An antibody that is contemplated by the present invention can be in any of a variety of forms, including a whole immunoglobulin, an antibody fragment such as Fv, Fab, and similar fragments, as well as a single chain antibody that includes the variable domain complementarity determining regions (CDR), and similar forms, all of which fall under the broad term "antibody," as used herein.

The term "antibody fragment" refers to a portion of a full-length antibody, generally the antigen binding or variable region. Examples of antibody fragments include Fab, Fab', F(ab')$_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment of an antibody yields an F(ab')$_2$ fragment that has two antigen binding fragments, which are capable of cross-linking antigen, and a residual other fragment (which is termed pFc'). Additional fragments can include diabodies, linear antibodies, single-chain antibody molecules, and multispecific antibodies formed from antibody fragments. As used herein, "antigen binding fragment" with respect to antibodies, refers to, for example, Fv, F(ab) and F(ab')$_2$ fragments.

Antibody fragments can retain an ability to selectively bind with the antigen or analyte are contemplated within the scope of the invention and include:

(1) Fab is the fragment of an antibody that contains a monovalent antigen-binding fragment of an antibody molecule. A Fab fragment can be produced by digestion of whole antibody with the enzyme papain to yield an intact light chain and a portion of one heavy chain.

(2) Fab' is the fragment of an antibody molecule can be obtained by treating whole antibody with pepsin, followed by reduction, to yield an intact light chain and a portion of the heavy chain. Two Fab' fragments are obtained per antibody molecule. Fab' fragments differ from Fab fragments by the addition of a few residues at the carboxyl terminus of the heavy chain CH1 domain including one or more cysteines from the antibody hinge region.

(3) (Fab')$_2$ is the fragment of an antibody that can be obtained by treating whole antibody with the enzyme pepsin without subsequent reduction. F(ab')$_2$ is a dimer of two Fab' fragments held together by two disulfide bonds.

(4) Fv is the minimum antibody fragment that contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

(5) Single chain antibody ("SCA"), defined as a genetically engineered molecule containing the variable region of the light chain ($V_L$), the variable region of the heavy chain ($V_H$), linked by a suitable polypeptide linker as a genetically fused single chain molecule. Such single chain antibodies are also referred to as "single-chain Fv" or "sFv" antibody fragments. Generally, the Fv polypeptide further comprises a polypeptide linker between the $V_H$ and $V_L$ domains that enables the sFv to form the desired structure for antigen binding. For a review of sFv fragments, see Pluckthun in The Pharmacology of Monoclonal Antibodies, vol. 113, Rosenburg and Moore eds. Springer-Verlag, N.Y., pp. 269 315 (1994).

Antibodies within the scope of the invention can be of any isotype, including IgG, IgA, IgE, IgD, and IgM. IgG isotype antibodies can be further subdivided into IgG1, IgG2, IgG3, and IgG4 subtypes. IgA antibodies can be further subdivided into IgA1 and IgA2 subtypes.

Antibodies of the subject invention can be genus or species specific to a target. Antibodies of the invention can be prepared using standard techniques known in the art. Antibodies useful in the invention can be polyclonal or monoclonal antibodies. Monoclonal antibodies can be prepared using standard methods known in the art (Kohler et al., 1975). Antibodies of the invention can be mammalian antibodies, including mouse, rat, goat, rabbit, pig, dog, cat, monkey, chimpanzee, ape, or human.

The subject invention also concerns compositions comprising one or more peptides or polynucleotides of the invention. In one embodiment, a composition further comprises a suitable carrier, diluent, or buffer. Compositions contemplated within the scope of the invention can comprise one or more peptides or polynucleotides of the invention and, optionally, one or more other compounds for treating autoimmune conditions or other conditions associated with activated tyrosine kinases. For example, a peptide of the invention can be provided in a composition with one or more of cyclophosphamide, methotrexate, mycophenolate, azathioprine, leflunomide, and prednisone. In one embodiment, the composition comprises a peptide or polynucleotide of the invention in a pharmaceutically or physiologically acceptable carrier, buffer, or diluent.

In one embodiment, peptides, polynucleotides, antibodies, and other agents of the invention are modified so as to enhance uptake into a cell. In one embodiment, a lipophilic group is attached to a peptide, polynucleotide, or other agent of the invention. In one embodiment, a palmitic acid is attached to a peptide of the invention. In a specific embodiment, a palmitoyl-lysine group is attached to the peptide, for example at the N-terminus of the peptide. Other methods for enhancing uptake of a peptide, polynucleotide, and antibody into a cell are known in the art and are contemplated within the scope of the invention.

Peptides, polynucleotides, antibodies, compositions, and other agents of the invention can also be delivered into cells by encapsulation of the peptide, polynucleotide, antibody, and other agents of the invention within a liposome. Methods for encapsulation of peptides, polynucleotides, antibodies, and other agents of the invention within liposomes are well known in the art.

Peptides having substitution of amino acids other than those specifically exemplified in the subject peptides are also contemplated within the scope of the present invention. For example, non-natural amino acids can be substituted for the amino acids of a peptide of the invention, so long as the peptide having substituted amino acids retains substantially the same activity as the peptide in which amino acids have not been substituted. Examples of non-natural amino acids include, but are not limited to, ornithine, citrulline, hydroxyproline, homoserine, phenylglycine, taurine, iodotyrosine, 2,4-diaminobutyric acid, α-amino isobutyric acid, 4-aminobutyric acid, 2-amino butyric acid, γ-amino butyric acid, ε-amino hexanoic acid, 6-amino hexanoic acid, 2-amino isobutyric acid, 3-amino propionic acid, norleucine, norvaline, sarcosine, homocitrulline, cysteic acid, τ-butylglycine, τ-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Non-natural amino acids also include amino acids having derivatized side groups. Furthermore, any of the amino acids in the protein can be of the D (dextrorotary) form or L (levorotary) form.

Amino acids can be generally categorized in the following classes: non-polar, uncharged polar, basic, and acidic. Conservative substitutions whereby a peptide having an amino acid of one class is replaced with another amino acid of the same class fall within the scope of the subject invention so long as the peptide having the substitution still retains substantially the same biological activity as a peptide that does not have the substitution. Table 1 below provides a listing of examples of amino acids belonging to each class.

TABLE 1

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |

TABLE 1-continued

| Class of Amino Acid | Examples of Amino Acids |
|---|---|
| Acidic | Asp, Glu |
| Basic | Lys, Arg, His |

Single letter amino acid abbreviations are defined in Table 2.

TABLE 2

| Letter Symbol | Amino Acid |
|---|---|
| A | Alanine |
| B | Asparagine or aspartic acid |
| C | Cysteine |
| D | Aspartic Acid |
| E | Glutamic Acid |
| F | Phenylalanine |
| G | Glycine |
| H | Histidine |
| I | Isoleucine |
| K | Lysine |
| L | Leucine |
| M | Methionine |
| N | Asparagine |
| P | Proline |
| Q | Glutamine |
| R | Arginine |
| S | Serine |
| T | Threonine |
| V | Valine |
| W | Tryptophan |
| Y | Tyrosine |
| Z | Glutamine or glutamic acid |

The peptides of the present invention can be formulated into pharmaceutically-acceptable salt forms. Pharmaceutically-acceptable salt forms include the acid addition salts and include hydrochloric, hydrobromic, nitric, phosphoric, carbonic, sulphuric, and organic acids like acetic, propionic, benzoic, succinic, fumaric, mandelic, oxalic, citric, tartaric, maleic, and the like. Pharmaceutically-acceptable base addition salts include sodium, potassium, calcium, ammonium, and magnesium salts. Pharmaceutically-acceptable salts of the peptides of the invention can be prepared using conventional techniques.

The subject invention also concerns polynucleotide expression constructs that comprise a polynucleotide of the present invention comprising a nucleotide sequence encoding a peptide of the present invention. In one embodiment, the polynucleotide encodes a peptide comprising the amino acid sequence shown in SEQ ID NO:1, SEQ ID NO:2, SEQ ID NO:3, SEQ ID NO:4, SEQ ID NO:27, SEQ ID NO:28, SEQ ID NO:29, SEQ ID NO:30, SEQ ID NO:51, SEQ ID NO:52, SEQ ID NO:53, or SEQ ID NO:54, or a fragment or variant thereof that exhibits substantially the same activity as the full-length non-variant peptide.

As used herein, the term "expression construct" refers to a combination of nucleic acid sequences that provides for transcription of an operably linked nucleic acid sequence. As used herein, the term "operably linked" refers to a juxtaposition of the components described wherein the components are in a relationship that permits them to function in their intended manner. In general, operably linked components are in contiguous relation.

Expression constructs of the invention will also generally include regulatory elements that are functional in the intended host cell in which the expression construct is to be expressed. Thus, a person of ordinary skill in the art can select regulatory elements for use in, for example, bacterial host cells, yeast host cells, plant host cells, insect host cells, mammalian host cells, and human host cells. Regulatory elements include promoters, transcription termination sequences, translation termination sequences, enhancers, and polyadenylation elements.

An expression construct of the invention can comprise a promoter sequence operably linked to a polynucleotide sequence encoding a peptide of the invention. Promoters can be incorporated into a polynucleotide using standard techniques known in the art. Multiple copies of promoters or multiple promoters can be used in an expression construct of the invention. In a preferred embodiment, a promoter can be positioned about the same distance from the transcription start site as it is from the transcription start site in its natural genetic environment. Some variation in this distance is permitted without substantial decrease in promoter activity. A transcription start site is typically included in the expression construct.

For expression in animal cells, an expression construct of the invention can comprise suitable promoters that can drive transcription of the polynucleotide sequence. If the cells are mammalian cells, then promoters such as, for example, actin promoter, metallothionein promoter, NF-kappaB promoter, EGR promoter, SRE promoter, IL-2 promoter, NFAT promoter, osteocalcin promoter, SV40 early promoter and SV40 late promoter, Lck promoter, BMP5 promoter, TRP-1 promoter, murine mammary tumor virus long terminal repeat promoter, STAT promoter, or an immunoglobulin promoter can be used in the expression construct. The baculovirus polyhedrin promoter can be used with an expression construct of the invention for expression in insect cells. Promoters suitable for use with an expression construct of the invention in yeast cells include, but are not limited to, 3-phosphoglycerate kinase promoter, glyceraldehyde-3-phosphate dehydrogenase promoter, metallothionein promoter, alcohol dehydrogenase-2 promoter, and hexokinase promoter.

For expression in prokaryotic systems, an expression construct of the invention can comprise promoters such as, for example, alkaline phosphatase promoter, tryptophan (trp) promoter, lambda $P_L$ promoter, β-lactamase promoter, lactose promoter, phoA promoter, T3 promoter, T7 promoter, or tac promoter (de Boer et al., 1983).

If the expression construct is to be provided in a plant cell, plant viral promoters, such as, for example, the cauliflower mosaic virus (CaMV) 35S (including the enhanced CaMV 35S promoter (see, for example U.S. Pat. No. 5,106,739)) or 19S promoter can be used. Plant promoters such as prolifera promoter, Ap3 promoter, heat shock promoters, T-DNA 1'- or 2'-promoter of A. tumefaciens, polygalacturonase promoter, chalcone synthase A (CHS-A) promoter from petunia, tobacco PR-1a promoter, ubiquitin promoter, actin promoter, alcA gene promoter, pin2 promoter (Xu et al., 1993), maize Wip1 promoter, maize trpA gene promoter (U.S. Pat. No. 5,625,136), maize CDPK gene promoter, and RUBISCO SSU promoter (U.S. Pat. No. 5,034,322) can also be used. Seed-specific promoters such as the promoter from a β-phaseolin gene (of kidney bean) or a glycinin gene (of soybean), and others, can also be used. Constitutive promoters (such as the CaMV, ubiquitin, actin, or NOS promoter), tissue-specific promoters (such as the E8 promoter from tomato), developmentally-regulated promoters, and inducible promoters (such as those promoters than can be induced by heat, light, hormones, or chemicals) are contemplated for use with the polynucleotides of the invention.

Expression constructs of the invention may optionally contain a transcription termination sequence, a translation termination sequence, signal peptide sequence, and/or enhancer elements. Transcription termination regions can typically be obtained from the 3' untranslated region of a eukaryotic or viral gene sequence. Transcription termination sequences can be positioned downstream of a coding sequence to provide for efficient termination. Signal peptides are a group of short amino terminal sequences that encode information responsible for the relocation of an operably linked peptide to a wide range of post-translational cellular destinations, ranging from a specific organelle compartment to sites of protein action and the extracellular environment. Targeting a peptide to an intended cellular and/or extracellular destination through the use of operably linked signal peptide sequence is contemplated for use with the peptides of the invention. Chemical enhancers are cis-acting elements that increase gene transcription and can also be included in the expression construct. Chemical enhancer elements are known in the art, and include, but are not limited to, the CaMV 35S enhancer element, cytomegalovirus (CMV) early promoter enhancer element, and the SV40 enhancer element. DNA sequences which direct polyadenylation of the mRNA encoded by the structural gene can also be included in the expression construct.

Unique restriction enzyme sites can be included at the 5' and 3' ends of the expression construct to allow for insertion into a polynucleotide vector. As used herein, the term "vector" refers to any genetic element, including for example, plasmids, cosmids, chromosomes, phage, virus, and the like, which is capable of replication when associated with proper control elements and which can transfer polynucleotide sequences between cells. Vectors contain a nucleotide sequence that permits the vector to replicate in a selected host cell. A number of vectors are available for expression and/or cloning, and include, but are not limited to, pBR322, pUC series, M13 series, and pBLUESCRIPT vectors (Stratagene, La Jolla, Calif.).

Polynucleotides, vectors, and expression constructs of the subject invention can be introduced into a cell by methods known in the art. Such methods include transfection, microinjection, electroporation, lipofection, cell fusion, calcium phosphate precipitation, and by biolistic methods. In one embodiment, a polynucleotide or expression construct of the invention can be introduced in vivo via a viral vector such as adeno-associated virus (AAV), herpes simplex virus (HSV), papillomavirus, adenovirus, and Epstein-Barr virus (EBV). Attenuated or defective forms of viral vectors that can be used with the subject invention are known in the art. Typically, defective virus is not capable of infection after the virus is introduced into a cell. Polynucleotides, vectors, and expression constructs of the invention can also be introduced in vivo via lipofection (DNA transfection via liposomes prepared from synthetic cationic lipids) (Felgner et al., 1987). Synthetic cationic lipids (LIPOFECTIN, Invitrogen Corp., La Jolla, Calif.) can be used to prepare liposomes to encapsulate a polynucleotide, vector, or expression construct of the invention. A polynucleotide, vector, or expression construct of the invention can also be introduced in vivo as naked DNA using methods known in the art, such as transfection, microinjection, electroporation, calcium phosphate precipitation, and by biolistic methods.

Polynucleotides and peptides of the subject invention can also be defined in terms of more particular identity and/or similarity ranges with those exemplified herein. The sequence identity will typically be greater than 60%, preferably greater than 75%, more preferably greater than 80%, even more preferably greater than 90%, and can be greater than 95%. The identity and/or similarity of a sequence can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein. Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used. See NCBI/NIH website.

The subject invention also contemplates those polynucleotide molecules (encoding peptides of the invention) having sequences which are sufficiently homologous with the polynucleotide sequences encoding a peptide of the invention so as to permit hybridization with that sequence under standard stringent conditions and standard methods (Maniatis, T. et al., 1982). As used herein, "stringent" conditions for hybridization refers to conditions wherein hybridization is typically carried out overnight at 20-25 C below the melting temperature (Tm) of the DNA hybrid in 6×SSPE, 5×Denhardt's solution, 0.1% SDS, 0.1 mg/ml denatured DNA. The melting temperature is described by the following formula (Beltz, G. A. et al., 1983):

$$Tm=81.5C+16.6 \text{ Log } [Na+]+0.41(\% \ G+C)-0.61(\% \text{ formamide})-600/\text{length of duplex in base pairs}.$$

Washes are typically carried out as follows:

(1) Twice at room temperature for 15 minutes in 1×SSPE, 0.1% SDS (low stringency wash).

(2) Once at Tm−20 C for 15 minutes in 0.2×SSPE, 0.1% SDS (moderate stringency wash).

As used herein, the terms "nucleic acid" and "polynucleotide sequence" refer to a deoxyribonucleotide or ribonucleotide polymer in either single- or double-stranded form, and unless otherwise limited, would encompass known analogs of natural nucleotides that can function in a similar manner as naturally-occurring nucleotides. The polynucleotide sequences include both the DNA strand sequence that is transcribed into RNA and the RNA sequence that is translated into protein. The polynucleotide sequences include both full-length sequences as well as shorter sequences derived from the full-length sequences. It is understood that a particular polynucleotide sequence includes the degenerate codons of the native sequence or sequences which may be introduced to provide codon preference in a specific host cell. The polynucleotide sequences falling within the scope of the subject invention further include sequences which specifically hybridize with the sequences coding for a peptide of the invention. The polynucleotide includes both the sense and antisense strands as either individual strands or in the duplex.

The subject invention also concerns methods for inhibiting tyrosine kinases, such as JAK2 and TYK2, in a cell. In one embodiment, a cell is contacted with an effective amount of one or more peptide, polynucleotide, or a composition of the invention. In one embodiment, the peptide has the amino acid sequence of SEQ ID NO:1, SEQ ID NO:2, SEQ ID NO:3, SEQ ID NO:4, SEQ ID NO:27, SEQ ID NO:28, SEQ ID NO:29, SEQ ID NO:30, SEQ ID NO:51, SEQ ID NO:52, SEQ ID NO:53, or SEQ ID NO:54, or a fragment or variant thereof that exhibits tyrosine kinase inhibitory activity. In one embodiment, the composition comprises a peptide of the invention and an anti-inflammatory drug or an immunosuppressant. The cell can be a human or mammalian cell. In one embodiment, the cell can be a keratinocyte, a fibroblast, a macrophage, or a lymphocyte. Peptides, polynucleotides, compositions, and/or other agents of the invention can be delivered to a cell either through direct contact of peptide, etc. with the cell or via a carrier means. Carrier means for delivering compositions to cells are known in the art and include encapsulating the composition in a liposome moiety, and attaching the peptide or polynucleotide to a protein or nucleic acid that is targeted for delivery to the target cell. Published U.S. Patent Application Nos. 20030032594 and 20020120100 disclose amino acid sequences that can be coupled to another peptide, protein, or nucleic acid and that allows the peptide, protein, or nucleic acid to be translocated across biological membranes. Published U.S. Patent Application No. 20020035243 also describes compositions for transporting biological moieties, such as peptides and proteins across cell membranes for intracellular delivery. Peptides can also be delivered using a polynucleotide that encodes a subject peptide. In one embodiment, the polynucleotide is delivered to the cell where it is taken up and the polynucleotide is transcribed into RNA and the RNA is translated into the encoded peptide. Methods of the invention can be conducted in vitro or in vivo.

The subject invention also concerns methods for preventing or treating an autoimmune and/or inflammatory disorder in a patient. In one embodiment, the disorder is SLE. In another embodiment, the disorder is multiple sclerosis (MS) or experimental allergic encephalitis (EAE). In a further embodiment, the disorder is rheumatoid arthritis (RA). In another embodiment, the disorder is psoriasis. In a further embodiment, the disorder is uveitis. In another embodiment, the disorder is diabetes. Any autoimmune and/or inflammatory disorder, including, but not limited to, amyotrophic lateral sclerosis, dermatitis, autoimmune peripheral neuropathy, autoimmune thrombocytopenic purpura, autoimmune lymphoproliferative syndrome (ALPS), Crohn's disease, Goodpasture's syndrome, Graves' disease Guillain-Barrè syndrome (GBS), idiopathic thrombocytopenic purpura, myasthenia gravis, psoriatic arthritis, rheumatoid arthritis, Sjögren's syndrome, ulcerative colitis, and vasculitis, is included within the scope of the present invention. In one embodiment, an effective amount of one or more peptide, polynucleotide, and/or composition of the present invention is administered to a patient having an autoimmune and/or inflammatory disorder and who is in need of treatment thereof. Optionally, the patient is a person or animal at risk of developing an autoimmune and/or inflammatory disorder. In one embodiment of the method, the peptide has the amino acid sequence in SEQ ID NO:1, SEQ ID NO:2, SEQ ID NO:3, SEQ ID NO:4, SEQ ID NO:27, SEQ ID NO:28, SEQ ID NO:29, SEQ ID NO:30, SEQ ID NO:51, SEQ ID NO:52, SEQ ID NO:53, or SEQ ID NO:54, or a fragment or variant thereof that exhibits tyrosine kinase inhibitory activity. Methods of the invention can also further comprise administering one or more compounds or drugs useful for treating an autoimmune and/or inflammatory disorder. Examples of such compounds or drugs include non-steroidal anti-inflammatory drugs (NSAIDs) (such as aspirin, acetaminophen, ibuprofen, nabumetone, and celecoxib), corticosteroids, cyclophosphamide, methotrexate, azathioprine, belimumab, teriflunomide, interferon beta-1a, interferon beta-1b, glatiramer acetate, fingolimod, mitoxantrone, dimethyl fumarate, and/or natalizumab. Such compounds or drugs can be administered prior to, in conjunction with, and/or subsequent to administration of a peptide, polynucleotide, and/or composition of the present invention. The patient can be a human or other mammal, such as a dog, cat, or horse, or other animals having the disorder. Methods of the invention can optionally comprise identifying that a person or animal has or may develop a disorder and is in need of treatment or prevention. Means for administering and formulating peptides and polynucleotides for administration to a patient are known in the art, examples of which are described herein. Peptides, polynucleotides, and/or compositions of the invention can be delivered to a cell either through direct contact of peptide, polynucleotide, or composition with the cell or via a carrier means. In one embodiment, a peptide, polynucleotide, or composition of the invention comprises an attached group that enhances cellular uptake of the peptide. In one embodiment, the peptide, polynucleotide, or composition is attached to an antibody that binds to a targeted cell. In another embodiment, the peptide, polynucleotide, or composition is encapsulated in a liposome. Peptides can also be delivered using a polynucleotide that encodes a subject peptide. Any polynucleotide having a nucleotide sequence that encodes a peptide of the invention is contemplated within the scope of the invention. In one embodiment, the polynucleotide is delivered to the cell where it is taken up and the polynucleotide is transcribed into RNA and the RNA is translated into the encoded peptide.

The subject invention also concerns methods for treating an oncological disorder (e.g., cancer) or an autoimmune disorder in a patient. In one embodiment, an effective amount of one or more peptide, polynucleotide, or composition of the present invention is administered to a patient having an oncological disorder or an autoimmune disorder and who is in need of treatment thereof. The subject invention also concerns methods for inhibiting the growth of a cancer cell by contacting the cell in vitro or in vivo with an effective amount of a peptide, polynucleotide, or composition of the present invention. In one embodiment, the peptide has the amino acid sequence in SEQ ID NO:1, SEQ ID NO:2, SEQ ID NO:3, SEQ ID NO:4, SEQ ID NO:27, SEQ ID NO:28, SEQ ID NO:29, SEQ ID NO:30, SEQ ID NO:51, SEQ ID NO:52, SEQ ID NO:53, or SEQ ID NO:54, or a fragment or variant thereof that exhibits tyrosine kinase inhibitory activity. Methods of the invention can also further comprise administering or contacting a cell with one or more compounds for treating an oncological or autoimmune disorder. Such compounds can be administered prior to, in conjunction with, and/or subsequent to administration of a peptide, polynucleotide, and/or composition of the present invention. Methods of the invention can optionally include identifying a patient who is or may be in need of treatment of an oncological or autoimmune disorder. The patient can be a human or other mammal, such as a primate (monkey, chimpanzee, ape, etc.), dog, cat, cow, pig, or horse, or other animals having an oncological disorder. Means for administering and formulating peptides, polynucleotides, or compositions of the invention for administration to a patient are known in the art, examples of which are described herein. In one embodiment, a SOCS1-KIR (SEQ ID NO:1) peptide, or a peptide dimer (SEQ ID NO:4 or SEQ ID NO:29), or a SOCS3-KIR (SEQ ID NO:51) peptide, or a peptide dimer (SEQ ID NO:52 or SEQ ID NO:54), or a polynucleotide encoding the peptide, is used to treat a person or animal having the disorder. Oncological disorders within the scope of the invention include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment with the present invention include carcinomas, Kaposi's sarcoma, melanoma, mesothelioma, soft tissue sarcoma, pancreatic cancer, lung cancer, leukemia (hairy cell, acute lymphoblastic, acute myeloid, chronic lymphocytic, chronic myeloid, and other), and lymphoma (Hodgkin's and non-Hodgkin's), and follicular lymphoma, and multiple myeloma.

Examples of cancers that can be treated according to the present invention are listed in Table 3.

TABLE 3

| Examples of Cancer Types | |
|---|---|
| Acute Lymphoblastic Leukemia, Adult | Hairy Cell Leukemia |
| Acute Lymphoblastic Leukemia, Childhood | Head and Neck Cancer |
| | Hepatocellular (Liver) Cancer, Adult (Primary) |
| Acute Myeloid Leukemia, Adult | |
| Acute Myeloid Leukemia, Childhood | Hepatocellular (Liver) Cancer, Childhood (Primary) |
| Adrenocortical Carcinoma | |
| Adrenocortical Carcinoma, Childhood | Hodgkin's Lymphoma, Adult |
| AIDS-Related Cancers | Hodgkin's Lymphoma, Childhood |
| AIDS-Related Lymphoma | Hodgkin's Lymphoma During Pregnancy |
| Anal Cancer | Hypopharyngeal Cancer |
| Astrocytoma, Childhood Cerebellar | Hypothalamic and Visual Pathway Glioma, Childhood |
| Astrocytoma, Childhood Cerebral | |
| Basal Cell Carcinoma | Intraocular Melanoma |
| Bile Duct Cancer, Extrahepatic | Islet Cell Carcinoma (Endocrine Pancreas) |
| Bladder Cancer | Kaposi's Sarcoma |
| Bladder Cancer, Childhood | Kidney (Renal Cell) Cancer |
| Bone Cancer, Osteosarcoma/Malignant Fibrous Histiocytoma | Kidney Cancer, Childhood |
| | Laryngeal Cancer |
| Brain Stem Glioma, Childhood | Laryngeal Cancer, Childhood |
| Brain Tumor, Adult | Leukemia, Acute Lymphoblastic, Adult |
| Brain Tumor, Brain Stem Glioma, Childhood | Leukemia, Acute Lymphoblastic, Childhood |
| | Leukemia, Acute Myeloid, Adult |
| Brain Tumor, Cerebellar Astrocytoma, Childhood | Leukemia, Acute Myeloid, Childhood |
| | Leukemia, Chronic Lymphocytic |
| Brain Tumor, Cerebral Astrocytoma/Malignant Glioma, Childhood | Leukemia, Chronic Myelogenous |
| | Leukemia, Hairy Cell |
| | Lip and Oral Cavity Cancer |
| Brain Tumor, Ependymoma, Childhood | Liver Cancer, Adult (Primary) |
| Brain Tumor, Medulloblastoma, Childhood | Liver Cancer, Childhood (Primary) |
| | Lung Cancer, Non-Small Cell |
| Brain Tumor, Supratentorial Primitive Neuroectodermal Tumors, Childhood | Lung Cancer, Small Cell |
| | Lymphoma, AIDS-Related |
| Brain Tumor, Visual Pathway and Hypothalamic Glioma, Childhood | Lymphoma, Burkitt's |
| | Lymphoma, Cutaneous T-Cell, see Mycosis Fungoides and Sézary Syndrome |
| Brain Tumor, Childhood | |
| Breast Cancer | Lymphoma, Hodgkin's, Adult |
| Breast Cancer, Childhood | Lymphoma, Hodgkin's, Childhood |
| Breast Cancer, Male | Lymphoma, Hodgkin's During Pregnancy |
| Bronchial Adenomas/Carcinoids, Childhood | Lymphoma, Non-Hodgkin's, Adult |
| | Lymphoma, Non-Hodgkin's, Childhood |
| Burkitt's Lymphoma | Lymphoma, Non-Hodgkin's During Pregnancy |
| Carcinoid Tumor, Childhood | |
| Carcinoid Tumor, Gastrointestinal | Lymphoma, Primary Central Nervous System |
| Carcinoma of Unknown Primary | Macroglobulinemia, Waldenström's |
| Central Nervous System Lymphoma, Primary | Malignant Fibrous Histiocytoma of Bone/Osteosarcoma |
| Cerebellar Astrocytoma, Childhood | Medulloblastoma, Childhood |
| Cerebral Astrocytoma/Malignant Glioma, Childhood | Melanoma |
| | Melanoma, Intraocular (Eye) |
| Cervical Cancer | Merkel Cell Carcinoma |
| Childhood Cancers | Mesothelioma, Adult Malignant |
| Chronic Lymphocytic Leukemia | Mesothelioma, Childhood |
| Chronic Myelogenous Leukemia | Metastatic Squamous Neck Cancer with Occult Primary |
| Chronic Myeloproliferative Disorders | |
| Colon Cancer | Multiple Endocrine Neoplasia Syndrome, Childhood |
| Colorectal Cancer, Childhood | |
| Cutaneous T-Cell Lymphoma, see Mycosis Fungoides and Sézary Syndrome | Multiple Myeloma/Plasma Cell Neoplasm |
| | Mycosis Fungoides |
| | Myelodysplastic Syndromes |
| Endometrial Cancer | Myelodysplastic/Myeloproliferative Diseases |
| Ependymoma, Childhood | Myelogenous Leukemia, Chronic |
| Esophageal Cancer | Myeloid Leukemia, Adult Acute |
| Esophageal Cancer, Childhood | Myeloid Leukemia, Childhood Acute |
| Ewing's Family of Tumors | Myeloma, Multiple |
| Extracranial Germ Cell Tumor, Childhood | Myeloproliferative Disorders, Chronic |
| | Nasal Cavity and Paranasal Sinus Cancer |

TABLE 3-continued

Examples of Cancer Types

| | |
|---|---|
| Extragonadal Germ Cell Tumor | Nasopharyngeal Cancer |
| Extrahepatic Bile Duct Cancer | Nasopharyngeal Cancer, Childhood |
| Eye Cancer, Intraocular Melanoma | Neuroblastoma |
| Eye Cancer, Retinoblastoma | Non-Hodgkin's Lymphoma, Adult |
| Gallbladder Cancer | Non-Hodgkin's Lymphoma, Childhood |
| Gastric (Stomach) Cancer | Non-Hodgkin's Lymphoma During Pregnancy |
| Gastric (Stomach) Cancer, Childhood | Non-Small Cell Lung Cancer |
| Gastrointestinal Carcinoid Tumor | Oral Cancer, Childhood |
| Germ Cell Tumor, Extracranial, Childhood | Oral Cavity Cancer, Lip and Oropharyngeal Cancer |
| Germ Cell Tumor, Extragonadal | Osteosarcoma/Malignant Fibrous |
| Germ Cell Tumor, Ovarian | Histiocytoma of Bone |
| Gestational Trophoblastic Tumor | Ovarian Cancer, Childhood |
| Glioma, Adult | Ovarian Epithelial Cancer |
| Glioma, Childhood Brain Stem | Ovarian Germ Cell Tumor |
| Glioma, Childhood Cerebral Astrocytoma | Ovarian Low Malignant Potential Tumor Pancreatic Cancer |
| Glioma, Childhood Visual Pathway and Hypothalamic | Pancreatic Cancer, Childhood Pancreatic Cancer, Islet Cell |
| Skin Cancer (Melanoma) | Paranasal Sinus and Nasal Cavity Cancer |
| Skin Carcinoma, Merkel Cell | Parathyroid Cancer |
| Small Cell Lung Cancer | Penile Cancer |
| Small Intestine Cancer | Pheochromocytoma |
| Soft Tissue Sarcoma, Adult | Pineoblastoma and Supratentorial Primitive |
| Soft Tissue Sarcoma, Childhood | Neuroectodermal Tumors, Childhood |
| Squamous Cell Carcinoma, see Skin Cancer (non-Melanoma) | Pituitary Tumor Plasma Cell Neoplasm/Multiple Myeloma |
| Squamous Neck Cancer with Occult Primary, Metastatic | Pleuropulmonary Blastoma Pregnancy and Breast Cancer |
| Stomach (Gastric) Cancer | Pregnancy and Hodgkin's Lymphoma |
| Stomach (Gastric) Cancer, Childhood | Pregnancy and Non-Hodgkin's Lymphoma |
| Supratentorial Primitive Neuroectodermal Tumors, Childhood | Primary Central Nervous System Lymphoma Prostate Cancer |
| T-Cell Lymphoma, Cutaneous, see Mycosis Fungoides and Sézary Syndrome | Rectal Cancer Renal Cell (Kidney) Cancer Renal Cell (Kidney) Cancer, Childhood |
| Testicular Cancer | Renal Pelvis and Ureter, Transitional Cell |
| Thymoma, Childhood | Cancer |
| Thymoma and Thymic Carcinoma | Retinoblastoma |
| Thyroid Cancer | Rhabdomyosarcoma, Childhood |
| Thyroid Cancer, Childhood | Salivary Gland Cancer |
| Transitional Cell Cancer of the Renal Pelvis and Ureter | Salivary Gland Cancer, Childhood Sarcoma, Ewing's Family of Tumors |
| Trophoblastic Tumor, Gestational | Sarcoma, Kaposi's |
| Unknown Primary Site, Carcinoma of, Adult | Sarcoma, Soft Tissue, Adult Sarcoma, Soft Tissue, Childhood |
| Unknown Primary Site, Cancer of, Childhood | Sarcoma, Uterine Sezary Syndrome |
| Unusual Cancers of Childhood | Skin Cancer (non-Melanoma) |
| Ureter and Renal Pelvis, Transitional Cell Cancer | Skin Cancer, Childhood |
| Urethral Cancer | |
| Uterine Cancer, Endometrial | |
| Uterine Sarcoma | |
| Vaginal Cancer | |
| Visual Pathway and Hypothalamic Glioma, Childhood | |
| Vulvar Cancer | |
| Waldenström's Macroglobulinemia | |
| Wilms' Tumor | |

For the treatment of oncological disorders, the peptides, polynucleotides, and compositions of this invention can be administered to a patient in need of treatment in combination with other antitumor or anticancer substances and/or with radiation and/or photodynamic therapy and/or with surgical treatment to remove a tumor. These other substances or treatments may be given at the same as or at different times from the peptides, polynucleotides, and compositions of this invention. For example, the peptides, polynucleotides, and compositions of the present invention can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively. Peptides, polynucleotides, and compositions of the invention can be used in combination with proteasome inhibitors, including, but not limited to, Bortezomib, Carfilzomib, and Salinosporamide A. The subject invention also concerns methods for inhibiting the growth of a cancer cell by contacting the cell in vitro or in vivo with an effective amount of a peptide, polynucleotide, or composition of the present invention.

Many tumors and cancers have viral genome present in the tumor or cancer cells. For example, Epstein-Barr Virus (EBV) is associated with a number of mammalian malignancies. The peptides, polynucleotides, and compositions of the subject invention can also be used alone or in combination with anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells.

The methods of the present invention can be used with humans and other animals. The other animals contemplated within the scope of the invention include domesticated, agricultural, or zoo- or circus-maintained animals. Domesticated animals include, for example, dogs, cats, rabbits, ferrets, guinea pigs, hamsters, pigs, monkeys or other primates, and gerbils. Agricultural animals include, for example, horses, mules, donkeys, burros, cattle, cows, pigs, sheep, and alligators. Zoo- or circus-maintained animals include, for example, lions, tigers, bears, camels, giraffes, hippopotamuses, and rhinoceroses.

In one embodiment, one or more of the peptides of the subject invention can be provided in the form of a multiple peptide construct. Such a construct can be designed so that multiple peptides are linked to each other by intervening moieties wherein the intervening moieties are subsequently cleaved or removed following administration of the multiple peptide construct to a patient. Methods for constructing multiple peptide constructs are known in the art. For example, peptides of the present invention can be provided in the form of a multiple antigenic peptide (MAP) construct. The preparation of MAP constructs has been described in Tam (1988). MAP constructs utilize a core matrix of lysine residues onto which multiple copies of an immunogen are synthesized. Multiple MAP constructs, each containing different peptides, can be prepared and administered in accordance with methods of the present invention. In another embodiment, a multiple peptide construct can be prepared by preparing the subject peptides having at least one metal chelating amino acid incorporated therein, preferably at the amino and/or carboxy terminal of the peptide as described, for example, in U.S. Pat. No. 5,763,585. The peptides are then contacted with a solid support having attached thereto a metal ion specific for the metal chelating amino acid of the peptide. A multiple peptide construct of the invention can provide multiple copies of the exact same peptide, including variants or fragments of a subject peptide, or copies of different peptides of the subject invention.

Therapeutic application of the subject peptides, polynucleotides, and compositions containing them, can be accomplished by any suitable therapeutic method and technique presently or prospectively known to those skilled in the art. The peptides and polynucleotides can be administered by any suitable route known in the art including, for example, topical, oral, nasal, rectal, parenteral, subcutaneous, or intravenous routes of administration. Administration of the peptides and polynucleotides of the invention can be continuous or at distinct intervals as can be readily determined by a person skilled in the art.

Compounds and compositions useful in the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive peptide or polynucleotide is combined with a suitable carrier in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically acceptable carriers and diluents which are known to those skilled in the art. Examples of carriers or diluents for use with the subject peptides and polynucleotides include, but are not limited to, water, saline, oils including mineral oil, ethanol, dimethyl sulfoxide, gelatin, cyclodextrans, magnesium stearate, dextrose, cellulose, sugars, calcium carbonate, glycerol, alumina, starch, and equivalent carriers and diluents, or mixtures of any of these. Formulations of the peptide or polynucleotide of the invention can also comprise suspension agents, protectants, lubricants, buffers, preservatives, and stabilizers. To provide for the administration of such dosages for the desired therapeutic treatment, pharmaceutical compositions of the invention will advantageously comprise between about 0.1% and 45%, and especially, 1 and 15% by weight of the total of one or more of the peptide or polynucleotide based on the weight of the total composition including carrier or diluent.

The peptides, polynucleotides, and compositions of the subject invention can also be administered utilizing liposome technology, slow release capsules, implantable pumps, and biodegradable containers. These delivery methods can, advantageously, provide a uniform dosage over an extended period of time.

The subject peptides and polynucleotides can also be modified by the addition of chemical groups, such as PEG (polyethylene glycol). PEGylated peptides typically generate less of an immunogenic response and exhibit extended half-lives in vivo in comparison to peptides that are not PEGylated when administered in vivo. Methods for PEGylating proteins and peptides known in the art (see, for example, U.S. Pat. No. 4,179,337). The subject peptides and polynucleotides can also be modified to improve cell membrane permeability. In one embodiment, cell membrane permeability can be improved by attaching a lipophilic moiety, such as a steroid, to the peptide or polynucleotide. In another embodiment, peptides and polynucleotides of the invention comprise a cell-penetrating peptide (CPP). CPPs are typically short peptides that are highly cationic and typically include several arginine and/or lysine amino acids. CPPs can be classified as hydrophilic, amphiphilic, or periodic sequence. In one embodiment, a CPP is provided at the terminus of a peptide or polynucleotide. Examples of CPPs include, but are not limited to penetratin or antennapedia PTD (RQIKWFQNRRMKWKK) (SEQ ID NO:31), TAT (YGRKKRRQRRR) (SEQ ID NO:32), SynB1 (RGGRLSYSRRRFSTSTGR) (SEQ ID NO:33), SynB3 (RRLSYSRRRF) (SEQ ID NO:34), PTD-4 (PIRRRKKLRRLK) (SEQ ID NO:35), PTD-5 (RRQRRTSKLMKR) (SEQ ID NO:36), FHV Coat-(35-49) (RRRRNRTRRNRRRVR) (SEQ ID NO:37), BMV Gag-(7-25) (KMTRAQRRAAARRNRWTAR) (SEQ ID NO:38), HTLV-II Rex-(4-16) (TRRQRTRRARRNR) (SEQ ID NO:39), D-Tat (GRKKRRQRRRPPQ) (SEQ ID NO:40), R9-Tat (GRRRRRRRRRPPQ) (SEQ ID NO:41), Transportan (GWTLNSAGYLLGKINLKALAALAKKIL) (SEQ ID NO:42) chimera, MAP (KLALKLALKLALALKLA) (SEQ ID NO:43), SBP (MGLGLHLLV-LAAALQGAWSQPKKKRKV) (SEQ ID NO:44), FBP (GALFLGWLGAAGSTMGAWSQPKKKRKV) (SEQ ID NO:45), MPG (ac-GALFLGFL-GAAGSTMGAWSQPKKKRKV-cya) (SEQ ID NO:46), MPG$^{(\Delta NLS)}$ (ac-GALFLGFLGAAGSTMGAWSQPK-SKRKV-cya) (SEQ ID NO:47), Pep-1 (ac-KETWWETWWTEWSQPKKKRKV-cya) (SEQ ID NO:48), and Pep-2 (ac-KETWFETWFTEWSQPKKKRKV-cya) (SEQ ID NO:49). Other CPPs can have only arginine (R) or only lysine (K) amino acids, e.g., having a formula $(R)_n$ or $(K)_n$, where n=an integer from 3 to 20. Other groups known in the art for providing for cell membrane permeability can be linked to peptides and polynucleotides of the present invention.

The subject invention also concerns a packaged dosage formulation comprising in one or more containers at least one peptide, polynucleotide, and/or composition of the subject invention formulated in a pharmaceutically acceptable dosage. The package can contain discrete quantities of the dosage formulation, such as tablet, capsules, lozenge, and powders. The quantity of peptide and/or polynucleotide in a dosage formulation and that can be administered to a patient can vary from about 1 mg to about 5000 mg, or about 1 mg to about 2000 mg, or more typically about 1 mg to about 500 mg, or about 5 mg to about 250 mg, or about 10 mg to about 100 mg.

The subject invention also concerns kits comprising one or more peptides, polynucleotides, compositions, compounds, or molecules of the present invention in one or more containers. In one embodiment, a kit contains a peptide, polynucleotide, and/or composition of the present invention. In a specific embodiment, a kit comprises a peptide comprising the amino acid sequence shown in SEQ ID NO:1, SEQ ID NO:2, SEQ ID NO:3, SEQ ID NO:4, SEQ ID NO:27, SEQ ID NO:28, SEQ ID NO:29, SEQ ID NO:30, SEQ ID NO:51, SEQ ID NO:52, SEQ ID NO:53, or SEQ ID NO:54, or a fragment or variant of the peptide that exhibits substantially the same activity as the full-length non-variant peptide e.g., tyrosine kinase inhibitory activity. A kit of the invention can also comprise, in addition to a peptide, polynucleotide, and/or composition of the invention, one or more compounds, biological molecules, or drugs for treating an autoimmune or an oncological disorder. For example, in one embodiment, a kit comprises one or more of non-steroidal anti-inflammatory drugs (NSAIDs) (such as aspirin, acetaminophen, ibuprofen, nabumetone, and celecoxib), corticosteroids, cyclophosphamide, methotrexate, azathioprine, belimumab, teriflunomide, interferon beta-1a, interferon beta-1b, glatiramer acetate, fingolimod, mitoxantrone, dimethyl fumarate, and/or natalizumab. In another embodiment, a kit comprises one or more of mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (imatinib) (Novartis Pharmaceuticals Corporation) and HERCEPTIN (trastuzumab) (Genentech, Inc.), respectively.

In one embodiment, a kit of the invention includes instructions or packaging materials that describe how to administer a peptide, polynucleotide, compositions, compounds, or molecules of the kit. Containers of the kit can be of any suitable material, e.g., glass, plastic, metal, etc., and of any suitable size, shape, or configuration. In one embodiment, a peptide, polynucleotide, compositions, compounds, or molecules of the invention is provided in the kit as a solid, such as a tablet, pill, or powder form. In another embodiment, a peptide, polynucleotide, compositions, compounds, or molecules of the invention is provided in the kit as a liquid or solution. In one embodiment, the kit comprises an ampoule or syringe containing a peptide, polynucleotide, compositions, compounds, or molecules of the invention in liquid or solution form.

The subject invention concerns peptide mimetics of suppressor of cytokine signaling 1 (SOCS1) and methods of use. They are active against SOCS targets, including both SOCS1 and SOCS3 tyrosine kinase targets. SOCS1 and SOCS3 are two important intracellular protein members of the eight-member SOCS family. SOCS1 and SOCS3 are particularly important physiologically in modulation of the immune system in protection against autoimmune diseases such as multiple sclerosis, lupus erythematosus, and psoriasis. The SOCS mimetics of the subject invention possess broad anti-autoimmune properties. The mimetics are small peptides (see, for example, SEQ ID NOs:1-4, 27-30, and 51-54) that have the common property of binding to the activation loop of the JAK2 and/or TYK2 tyrosine kinases. These JAK kinases play a critical role of mediation of signal transduction events of cytokines that have been implicated or associated with a range of autoimmune disorders. Notably, chemical tyrosine kinase inhibitors are currently utilized in various inflammation based cancers and leukocytic proliferative disorders. As such, SOCS mimetics of the present invention are an attractive alternative to chemical tyrosine kinase inhibitors which possess significant negative side effects.

In one embodiment, the SOCS mimetics of the invention are engineered for cell membrane penetration where they can bind to the JAKs in the cytoplasm of the cell. The mimetics were developed to bind to JAK2 and/or TYK2 at the activation loop of the JAKs. The SOCS1-KIR mimetic as a dimer with a six glycine (G) linker (SEQ ID NO:3) significantly increased the avidity for the activation loop of JAK2 with increased anti-cellular activity. Thus, multimers increase binding for increased biological effect. The N-terminus of SOCS1 and SOCS3 contain a short 12 amino acid kinase inhibitory region (KIR). Studies by others showed that KIR was important for SOCS1 and SOCS3 function, but not by binding to the activation loop of JAK2 and TYK2. Thus, our demonstration of such binding played an important role in our reasoning that analogs or sequences of KIR should function as SOCS mimetics if internalized in the cell.

The subject invention can be used in gene therapy to treat a disease or condition in a person or animal. In one embodiment, the disorder is SLE. In another embodiment, the disorder is multiple sclerosis (MS) or experimental allergic encephalitis (EAE). In a further embodiment, the disorder is rheumatoid arthritis (RA). In another embodiment, the disorder is psoriasis. In a further embodiment, the disorder is uveitis. In another embodiment, the disorder is diabetes or vascular problems such as vascular plaque accumulation. Any autoimmune and/or inflammatory disorder, including, but not limited to, amyotrophic lateral sclerosis, dermatitis, autoimmune peripheral neuropathy, autoimmune thrombocytopenic purpura, autoimmune lymphoproliferative syndrome (ALPS), Crohn's disease, Goodpasture's syndrome, Graves' disease Guillain-Barrè syndrome (GBS), idiopathic thrombocytopenic purpura, myasthenia gravis, Parkinson's disease, psoriatic arthritis, rheumatoid arthritis, Sjögren's syndrome, ulcerative colitis, and vasculitis, is included within the scope of the present invention. In one embodiment, a polynucleotide of the invention is incorporated into a cell or cells of a person or animal, and the polynucleotide expressed in the cell to produce a peptide of the invention. In a specific embodiment, a cell is removed from the body of the person or animal, the polynucleotide is incorporated into the cell, and the cell is then reintroduced back into the body of the person or animal and the polynucleotide expressed in the cell. In one embodiment, the polynucleotide is stably incorporated into the genome of the cell. In a specific embodiment, the polynucleotide is provided in an expression construct that provides for expression of the polynucleotide in the cell. In one embodiment, the peptide expressed in the cell is transported outside the cell and into the extracellular space of the person or animal.

Any methods of the subject invention can optionally include a step of identifying a person or animal who is or who may be in need of treatment or prevention of a disease, disorder, or condition.

Biological samples refer to a fluid or tissue composition obtained from a human or animal. Biological samples within the scope of the invention include, but are not limited to, cells, whole blood, peripheral blood, blood plasma, bone marrow, spleen, serum, urine, tears, saliva, sputum, exhaled breath, nasal secretions, pharyngeal exudates, bronchoalveolar lavage, tracheal aspirations, interstitial fluid, lymph fluid, meningeal fluid, amniotic fluid, glandular fluid, feces, perspiration, mucous, vaginal or urethral secretion, cerebrospinal fluid, and transdermal exudate. A biological sample also includes experimentally separated fractions of all of the preceding solutions or mixtures containing homogenized solid material, such as feces, cells, tissues, and biopsy samples.

The subject application also concerns methods for diagnosing and/or monitoring progression of an autoimmune or inflammatory disorder such as systemic lupus erythematosus (SLE) or a similar or related condition in a person or animal. In another embodiment, the disorder is Sjögren's syndrome or dermatitis. In one embodiment, a method of the invention comprises optionally obtaining a biological sample from the person or animal, and determining SOCS1 and/or SOCS3 RNA and/or protein levels of a cell from the person or animal, wherein reduced levels are indicative of SLE in the person or animal. In a specific embodiment, the levels are compared to the levels of a normal or healthy control person or animal. In another embodiment, the levels are compared to levels from the same person or animal obtained at an earlier time point. In a further embodiment, the levels are compared to a predetermined baseline level. Any method for screening or determining RNA or protein levels can be used with the subject methods. In one embodiment, SOCS1 and/or SOCS3 RNA levels are determined using RT-PCR. In another embodiment, RNA levels are determined using a cDNA or oligonucleotide microarray assay, or a Northern blot assay. In another embodiment, SOCS1 and/or SOCS3 protein levels are determined using an antibody based assay, including, but not limited to, Western blotting or an ELISA assay. In one embodiment, the method also further comprises treating the person or animal for SLE if the results are indicative that the person or animal has SLE or a similar or related condition. Treatment can include administration of any known and/or approved treatment for SLE, including but not limited to, prednisone and plaquenil. Treatment can include the use or administration of one or more peptide mimetics of the invention. In a further embodiment, the level of STAT1 activation is also determined, wherein reduced SOCS1 levels in an SLE patient are correlated with enhanced STAT1 activation (phosphorylation of STAT1). In another embodiment, the level of interferon gamma (IFNγ) and/or interleukin-27 (IL27) is also determined, wherein reduced IFNγ in an SLE patient is positively correlated with SOCS1 and SOCS3 levels.

The subject invention also concerns methods for screening for a drug or compound to treat an autoimmune or inflammatory disorder, such as SLE or a similar or related condition in a person or animal. In one embodiment, a method comprises optionally obtaining a biological sample from the person or animal, and determining SOCS1 and/or SOCS3 RNA and/or protein levels of a cell from the person or animal, wherein the person or animal has received a drug or compound for treating the disorder or the person or animal has received a drug or compound that is being evaluated for efficacy in treating the disorder prior to determining SOCS1 and/or SOCS3 levels in the person or animal. A drug or compound that increases levels of SOCS1 and/or SOCS3 in the person or animal would be indicative of a drug or compound that may be beneficial in treating a disorder in a person or animal. In one embodiment, levels of SOCS1 and/or SOCS3 are compared to baseline levels of SOCS1 and/or SOCS3 from the same person or animal taken prior to administration of the drug or compound. In another embodiment, the levels of SOCS1 and/or SOCS3 are compared to an established baseline level of SOCS1 and/or SOCS3 of patients having the disorder. The levels of SOCS1 and/or SOCS3 RNA and/or protein can be determined at various time intervals for the person or animal, e.g., every day, every few days, every week, every two weeks, every month, every two or three months, or any other time interval. Any method for screening or determining RNA or protein levels can be used with the subject methods. In one embodiment, SOCS1 and/or SOCS3 RNA levels are determined using RT-PCR. In another embodiment, RNA levels are determined using a cDNA or oligonucleotide microarray assay, or a Northern blot assay.

The subject invention also concerns methods for monitoring the progression of an autoimmune or inflammatory disorder, such as SLE or a similar or related condition in a person or animal. In one embodiment, a method of the invention comprises optionally obtaining a biological sample from the person or animal, and determining SOCS1 and/or SOCS3 RNA and/or protein levels of a cell from the person or animal, wherein decreasing levels are indicative of worsening of disease and increasing levels are indicative of improvement of disease in the person or animal. The levels of SOCS1 and/or SOCS3 RNA and/or protein can be determined at various time intervals for the person or animal, e.g., every day, every few days, every week, every two weeks, every month, every two or three months, or any other time interval recommended or required by a clinician. The levels of SOCS1 and/or SOCS3 RNA and/or protein can be compared to previously determined levels of the person or animal being evaluated or to a level of a control person or animal or to a predetermined baseline level. Any method for screening or determining RNA or protein levels can be used with the subject methods. In one embodiment, SOCS1 and/or SOCS3 RNA levels are determined using RT-PCR. In another embodiment, RNA levels are determined using a cDNA or oligonucleotide microarray assay, or a Northern blot assay.

Materials and Methods for Examples 1-12

Mice.

SOCS1$^{+/-}$ and SOCS1$^{+/+}$ (WT) mice were generated as previously described (Collins et al. 2011). Briefly, SOCS$^{+/-}$ mice, on a C56BL/6 genetic background, were purchased from the St. Jude animal facility (Memphis, Tenn.) and mated, generating WT, SOCS1$^{+/-}$, and SOCS1$^{-/-}$ mice. SOCS1$^{+/-}$ and WT littermate control mice were chosen for experiments. SOCS1$^{+/-}$IFNγ$^{-/-}$ mice were also purchased from the St. Jude animal facility. Mice were maintained under specific pathogen free conditions at the University of Florida Cancer and Genetics Animal Care Facility.

Genotyping.

Mouse genotyping was performed similar to (Collins et al. 2011). In brief, mouse tail clips (1 mm) were degraded using the DNAeasy Blood and Tissue Kit (Quiagen, Valecia, Calif.) to extract DNA, followed by quantitative PCR (qPCR) to assess of the presence SOCS1 using iQ™ SYBR Green Supermix (BioRad, Hercules, Calif.) and primers specific for SOCS1 (forward: 5'-GACACT-CACTTCCGCACCTT-3' (SEQ ID NO:5); reverse: 5'-GAAGCAGTTCCGTTGGCGACT-3') (SEQ ID NO:6) or β-actin (forward: 5'-CCACAGCACTGTAGGGTTTA-3' (SEQ ID NO:7); reverse: 5'ATTGTCTTTCTT-CTGCCGTTCTC-3' (SEQ ID NO:8)) (200 nM) which were used to amplify and quantify relative amounts of DNA on a PTC-200 Peltier Thermal Cycler with a CHROMO 4 Continuous Fluorescence Detector (BioRad, Hercules, Calif.). Mouse genotype was determined by relative expression of SOCS1. Expression was calculated using the ΔΔCT method.

Human Subjects.

17 SLE patients (16 females and 1 male; mean age: 48) and 8 healthy controls (5 females and 3 males; mean age: 30) were enrolled in this study. All SLE patients were diagnosed by the 1982 SLE criteria (Tan et al. 1982). Subjects with active infections and patients treated with mofetil mycophenolate, azathioprine, methotrexate, or systemic corticosteroids were excluded. This study was approved by the University of Florida Institutional Review Board (IRB).

Isolation of Human PBMCs.

PBMCs were purified from heparinized blood by Ficoll-Paque gradient centrifugation. Briefly, whole blood was diluted with PBS (1:1) and gently layered on the Ficoll (Lymphocyte Separation Medium; Cellgro, Manassas, Va.). Cells were centrifuged continuously at 400×g for 20 minutes. PBMCs were collected from the interface layer and washed 3 times with PBS. After isolation, PBMCs were harvested for CD64 surface staining, as previously described (Li et al. 2010), or lysed with RNA lysis buffer (Promega) and stored at -80° C. until RNA extraction and qPCR protocols were performed.

Peptide Synthesis.

The SOCS1-KIR peptide ($^{53}$DTHFRTFRSHSDYRRI) (SEQ ID NO:1) was synthesized using conventional fluorenylmethylcarbonyl chemistry, as previously described (Szente et al. 1994) using an Applied Biosystems 431A automated peptide synthesizer (Applied Bio-systems, Carlsbad, Calif.). For cell penetration, using a semi-automated protocol (Thiam et al. 1999), we added a lipophilic group (palmitoyl-lysine) to the amino terminus as a final step. The peptide was characterized using mass spectrometry and purified by HPLC. Once synthesized, SOCS1-KIR peptide was re-suspended in DMSO (Sigma-Aldrich, St. Louis, Mo.) and used for in vitro cell culture experiments.

Surface and Intracellular Staining.

To assess ex vivo T cell populations, single-cell suspensions were obtained from the thymus or pooled lymph nodes (axillary, brachial, cervical, inguinal, and mesenteric) and spleen. Aliquots of these organ-specific cell suspensions were stained as with the following monoclonal antibodies (mAb): anti-CD4-Pacific Blue (RM4-5; BD Biosciences, San Diego, Calif.) and anti-CD8a-Alexa Flour 700 (53-6.7; BD Biosciences). To determine the activation status of peripheral CD4$^+$ T cells, ex vivo, LN and spleen suspensions were also stained with anti-CD25-allophycocyanin (PC61; BD Biosciences) and anti-CD69-APC (H1.2F3; BD Biosciences). To assess CD4$^+$ T cell activation, in vitro, the same mAbs toward CD25 and CD69 were used as previously described for ex vivo experiments.

Foxp3 and IL-17A intracellular staining (ICS) were employed to assess in vitro Treg and Th17 induction, respectively. For Foxp3 ICS, cells were fixed and permeabilized using the reagents provided by the Foxp3/Transcription Factor Staining Buffer Set (eBioscience). Cells were then stained with anti-Foxp3-FITC (FJK-16s; eBioscience) Ab. For IL-17A and IFNγ ICS, prior to staining, cells were incubated with PMA (50 ng/ml), ionomycin (10 μM; Sigma-Aldrich. St. Louis, Mo.), and brefeldin A (10 μg/ml; MP Biomedicals, Solon, Ohio) for 4 hours at 37° C., as previously described (Bedoya et al. 2013). Cells were then fixed and permeabilized using the reagents provided by the Intracellular Cytokine Staining Starter Kit—Mouse (BD Biosciences). Following fixation and permeabilization, cells were stained with an anti-IL17A-Alexa Flour 700 or an anti-IFNγ-PE mAb. After staining (surface and ICS), a total of 50,000 live events were collected on an LSRII (BD Pharmingen) and analyzed using FlowJo software (Tree Star, San Carlos, Calif.).

Magnetic Cell Separation.

For each mouse, CD4$^+$CD25$^-$ T cells were enriched using a regulatory T cell isolation kit and magnetic-activated cell sorting (MACS) technology (Miltenyi Biotec, Bergisch Gladbach, Germany). After isolation, flow cytometry was used to assess the purity of CD4$^+$CD25$^-$ T cell populations used in experiments, and found to be typically ≥90%).

In Vitro T Cell Differentiation.

CD4$^+$CD25$^-$ T lymphocytes (1×10$^5$/well) were cultured in triplicate at 37° C. (5% CO$_2$) in RPMI 1640 (Cellgro 10-040-CV) containing 10% FBS (INVITROGEN™ GIBCO®) 1% antibiotic/antimycotic (Herndon, Va.), and 50 μM β-ME (MP Biomedicals, Solon, Ohio). For Treg differentiation, cells were stimulated with 2 μg/ml plate-bound anti-CD3 mAb (BD Pharmingen; clone: 145-2C11), 2 μg/ml soluble anti-CD28 mAb (BD Pharmingen; clone: 37.51), and 2 ng/ml human TGF-1 (R & D Systems). Cells were incubated for 72 hours and assessed for Treg differentiation by ICS for Foxp3. For Th17 differentiation, cells were stimulated with 10 μg/ml plate-bound anti-CD3 mAb (BD Pharmingen; clone: 145.2C11), 1.5 μg/ml soluble anti-CD28 mAb (BD Pharmingen; clone 37.51), 5 ng/ml human TGF-β (R & D Systems), and 20 ng/ml IL-6 (Ebioscience). CD4$^+$CD25$^-$ cells stimulated with plate-bound anti-CD3 mAb and soluble anti-CD28 mAb, or plate-bound anti-CD3 mAb alone, served as stimulation controls for both Treg and Th17 differentiation assays. For assays that included SOCS1-KIR mimetic peptide, 20 μM SOCS1-KIR peptide was added in culture at time zero in conjunction with Th17 inducing reagents. Cells were collected after 5 days and assessed for activation and Th17 differentiation.

Proliferation Assays.

CD4$^+$ T cell proliferation was assessed by CFSE staining, $^3$H thymidine incorporation, and absolute cell counts.

MACS purified CD4+CD25− T cells, isolated from LN and spleen suspension, were stimulated in triplicate (96 well round-bottom plate; 1×10$^5$ cells/well) with 10 μg/ml anti-CD3 (BD Pharmingen; clone: 145.2C11) alone or in addition to 1.5 μg/ml anti-CD28 (BD Pharmingen; clone 37.51) at 37° C. (5% $CO_2$) in RPMI 1640 (Cellgro; 10-040-CV) containing 10% FBS (INVITROGEN™ GIBCO®), 1% antibiotic/antimycotic (Herndon, Va.), and 50 μM β-ME (MP Biomedicals, Solon, Ohio). After 72 h of incubation, cell cultures were either pulsed with 0.5 mCi $^3$H thymidine (GE Healthcare; Arlington Heights, Ill.) or counted and harvested for assessment by flow cytometry. In cultures analyzed by flow cytometry, T lymphocytes were labeled with 10 μg/ml CFSE prior to culture as previously described (Cozzo et al. 2003). $^3$H thymidine pulsed T lymphocytes were harvested 16-18 hours after initial pulse followed by the $^3$H thymidine incorporation assessment using a Beckman LS3801 Liquid Scintillation System. Absolute cell numbers of CD4+CD25− lymphocytes were obtained via Trypan Blue exclusion.

RNA Extraction and qPCR.

Using the Promega RNA extraction protocol, total RNA was extracted from human PBMCs ex vivo or from mouse CD4+CD25− cells after being cultured under control (anti-CD3 and anti-CD28) or Th17 inducing conditions in the presence or absence of SOCS1-KIR peptide. cDNA synthesis and qPCR were performed as described in (Collins et al. 2011), with modifications. Briefly, cDNA synthesis was performed using the iQ cDNA synthesis kit (Bio-rad; Hercules, Calif.). To amplify the target and house-keeping genes present in cDNA, qPCR was subsequently performed using the iQ SYBR Green Supermix (Bio-Rad) and gene-specific primers (Table 4). The amplification reactions took place in a PTC-200 Peltier Thermal Cycler with a CHROMO 4 Continuous Fluorescence Detector (BioRad). The reaction protocol is as follows: one 2-3 min cycle at 95° C., followed by 50 cycles of denaturation (95° C., 15s), annealing (30s) (see Table 4 for primer specific temperature), and extension (72° C., 30s). To confirm amplicon specificity, melting curve analysis was performed. The fold change in expression was calculated using the ΔΔCT method.

In Vitro Cytokine Secretion Analysis.

SOCS1+/− and WT CD4+CD25− T cells were plated and stimulated in triplicate with plate-bound anti-CD3 alone (BD Pharmingen; clone: 145.2C11), plate-bound anti-CD3 and anti-CD28 (BD Pharmingen; clone 37.51), or Th17 inducing conditions for 5 days as previously described (Bedoya et al. 2013). After the incubation period, 100 μl of culture supernatant was collected from each well. Harvested supernatants were used to perform IL-17A and IFNγ ELISAs, as previously described (Lau et al. 2011). IL-17A capture (555068) and detection (555067) mAb, and IFN-γ cytokine standard (554587) were purchased from BD Biosciences. IL-17 cytokine standard (14-8171-80), IFN-γ capture (16-7313-85) and IFNγ detection (13-7311-85) mAbs were purchased from eBioscience.

IgG Antibody Assessment.

Total IgG and anti-dsDNA IgG levels were measured by ELISA as in Morel et al. (Morel et al. 2000). For the anti-ssDNA IgG ELISA, ssDNA was generated by heating rat dsDNA at 100° C. for 10 minutes, followed by a 5-minute incubation on ice. The resulting ssDNA was then used to coat the wells of flat-bottomed 96 well plate. Relative units of anti-DNA IgG were standardized using serum taken from C56BL/6 triple congenic (B6.TC) mice, which coexpress three lupus susceptibility loci (Sle1, Sle2, and Sle3) and develop severe lupus-like disease (Morel et al. 2000). 1:100 dilution of B6.TC serum was set to an equivalent of 100 units.

Western Blotting.

MACS purified CD4+CD25− T cells were stimulated with anti-CD3 Ab (10 μg/ml), anti-CD3 (10 μg/ml) and anti-CD28 (1.5 μg/ml) Abs, or Th17 inducing conditions in the presence or absence of SOCS1-KIR peptide as previously described. 2×10$^7$ cells from each condition were lysed with 100 μl of RIPA lysis buffer containing complete protease inhibitor (Santa Cruz; product number: SC-24948). Equal quantities of protein were loaded and separated in 4%-12% SDS-PAGE gel (Biorad). Separated proteins were transferred to nitrocellulose membrane (Amersham; HYBOND™-N+). The membrane was then blocked, probed with primary anti-pAkt (ser473) (catalogue #: 9271) or anti-pSTAT1 (Tyr701) (catalogue #: 9171) antibody and then with appropriate secondary antibodies conjugated to HRP, and visualized with the ECL detection system according to the manufacturer's instructions (Pierce; Product #32106). Akt (catalogue #: 9272) and STAT1 (catalogue #: 9172) immunoblots were performed to confirm equal loading.

Statistical Analysis.

GraphPad Prism v.5 was used to calculate the statistically significant differences between two different groups using the nonparametric, Mann-Whitney U test. For multiple comparisons tests, the nonparametric Kruskal-Wallis test was performed, followed by the Dunn's Multiple Comparisons post-test. For correlation data, the nonparametric Spearman correlation test was performed. A 95% confidence limit, defined by p values ≤0.05, was considered significant and is indicated within the figures.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1

Figure 7:
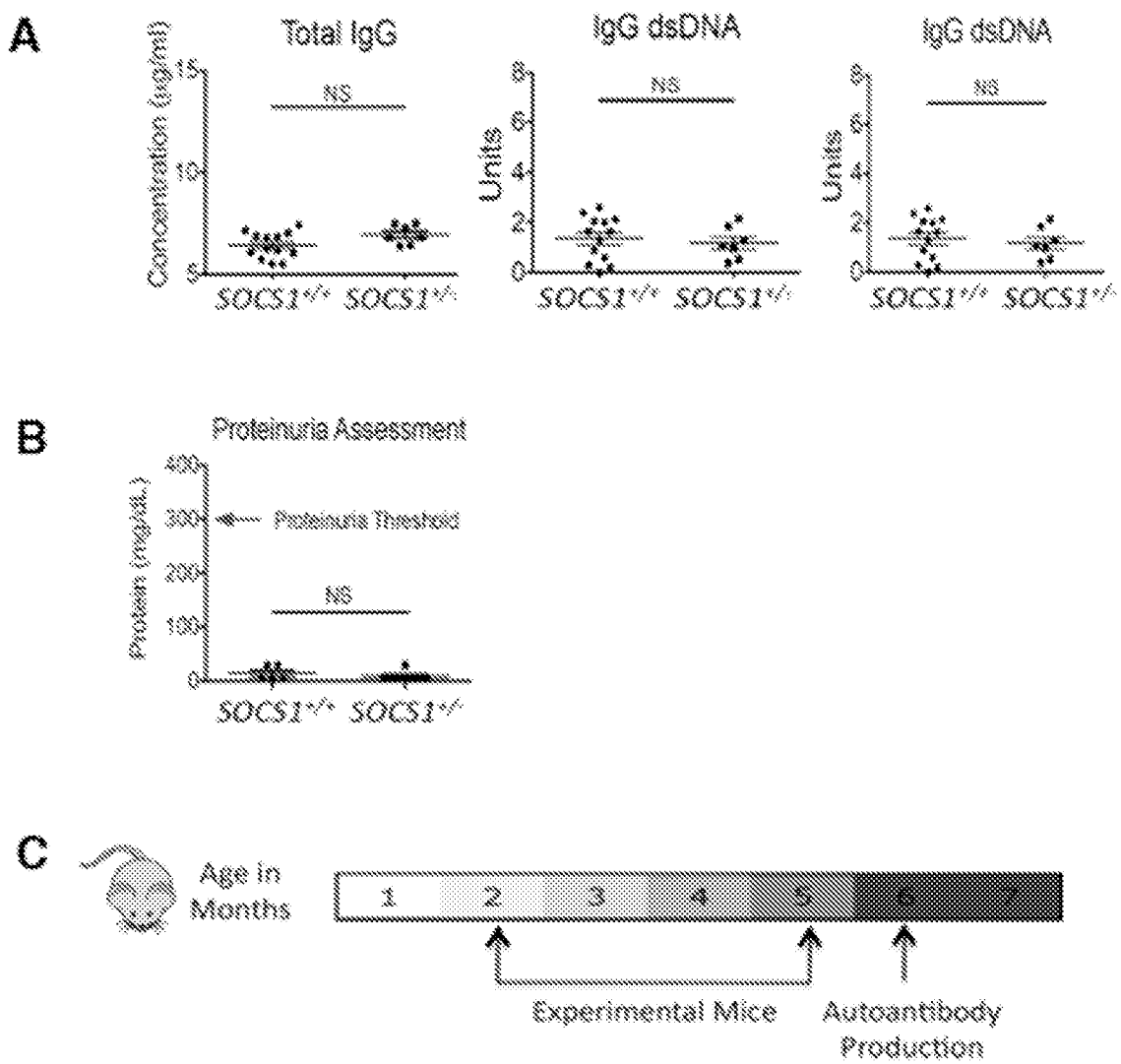
FIGS. 7A-7C. SOCS1$^{+/-}$ mice are free of SLE-like pathology at <6 months of age.

SOCS1+/− Mice Exhibit CD4 T Cell Accumulation and Enhanced CD4+ T Cell Activation in the Periphery In this study we selected SOCS1+/− mice between 2 and 5 months of age, which are free of overt lupus pathology (FIG. 7 and Fujimoto et al. 2004), to assess how SOCS1 deficiency precipitates CD4+ T lymphocyte mediated autoimmunity. We first assessed whether distinctions were present within the thymic and peripheral pools of CD4+ T lymphocytes in SOCS1+/− mice. Although the frequency and absolute numbers of CD4+CD8− thymocytes within SOCS1+/− and WT littermate controls were indistinct (FIG. 1A), CD4+ T lymphocytes in the periphery of SOCS1+/− mice were two fold higher in frequency, and four-fold higher in absolute cell number, when compared to WT littermate controls (FIG. 1B). As T lymphocyte activation may also contribute to lupus progression (Stekman et al. 1991; Desai-Mehta et al. 1996; Mohan et al. 1999; Vratsanos et al. 2001; Bouzahzah et al. 2003), we next assessed differences in the CD4+ T cell activation marker, CD25, directly ex-vivo.

Figure 8:
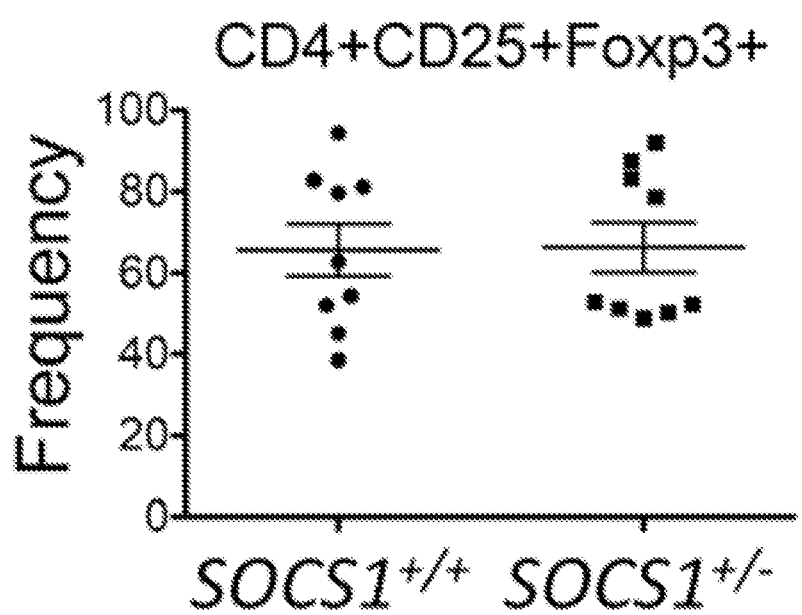
FIG. 8. SOCS1$^{+/-}$ mice possess a normal peripheral CD4$^+$CD25$^+$Foxp3$^+$ cell frequency. LNs and spleen from SOCS1$^{+/+}$ or SOCS1$^{+/-}$ mice were pooled and the CD4$^+$CD25$^+$Foxp3$^+$ frequency was assessed by flow cytometry. Results shown as mean±s.e.m. Statistical comparisons SOCS1$^{+/+}$ and SOCS1$^{+/-}$ mice were performed using the Mann-Whitney U test.

Indeed, SOCS1$^{+/-}$ mice possessed an increased frequency and nearly 3-fold more peripheral CD4+ T lymphocytes (6.9×10$^6$ vs. 2.4×10$^6$) that were also CD25$^+$ when compared to WT (FIG. 1C). This increase in CD25 expression was not due to increases in Tregs, as levels of Foxp3$^+$ T lymphocytes were indistinct between SOCS1$^{+/-}$ mice and littermate controls (FIG. 8). In addition to CD25 expression, activation of CD4$^+$ T lymphocytes can also be analyzed by the presence of the early activation marker CD69 (Testi et al. 1994; Larkin et al. 2007). CD4$^+$CD69$^+$ T lymphocytes were also higher in both frequency and absolute number within SOCS1$^{+/-}$ mice (FIG. 1C). Together, these data show that SOCS1$^{+/-}$ mice, which develop CD4 T cell-mediated lupus, possess significantly more activated CD4+ T lymphocytes, which may contribute to disease progression.

Example 2

Figure 2:
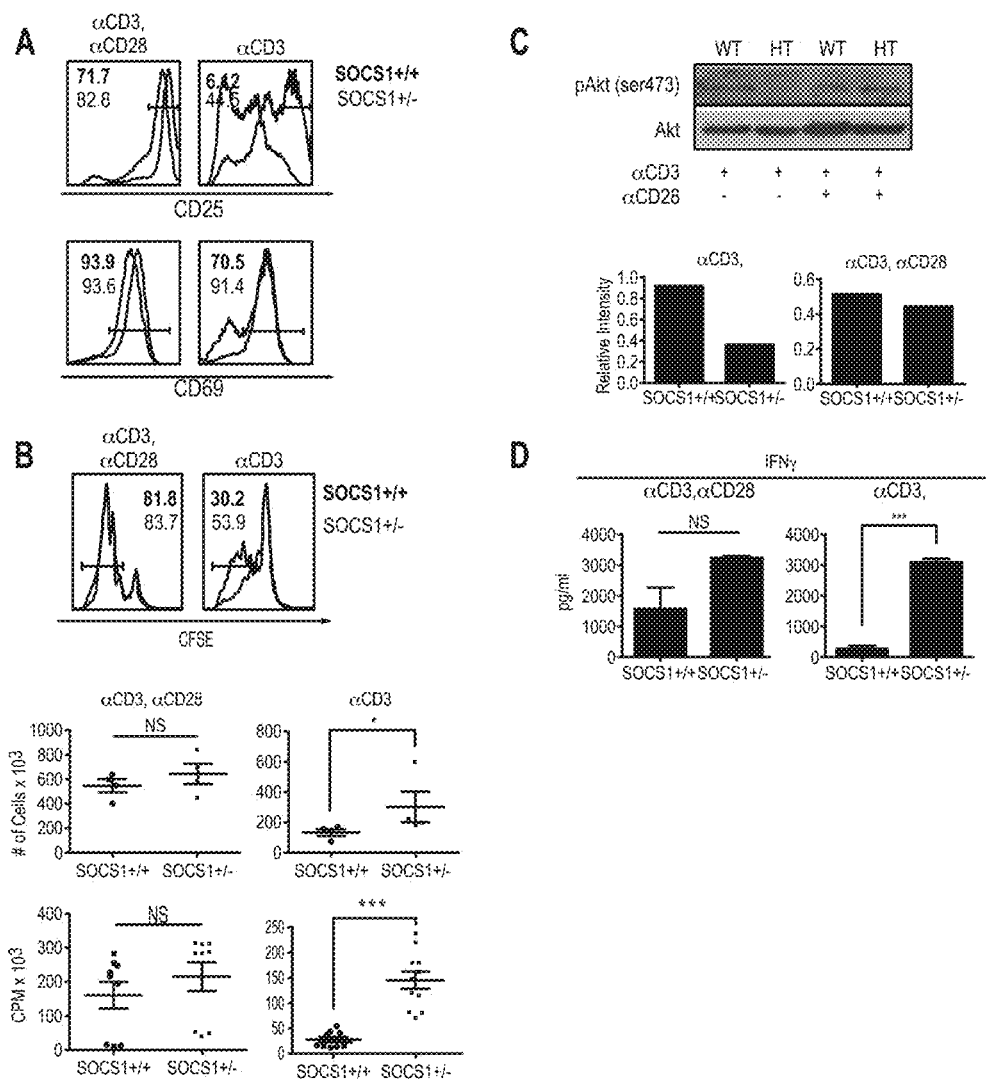
FIGS. 2A-2D. CD28 co-stimulation is dispensable for activation and expansion of SOCS1$^{+/-}$ CD4$^+$ T lymphocytes. CD4$^+$CD25$^-$ T cells from SOCS1$^{+/+}$ or SOCS1$^{+/-}$ mice were stimulated with αCD3 antibodies alone or with αCD3 and αCD28 antibodies for 72 h.

CD28 Co-Stimulation of SOCS1$^{+/-}$ CD4$^+$ T Lymphocytes is Dispensable for Activation and Clonal Expansion Having observed enhanced CD4$^+$ T cell activation within the periphery of SOCS1$^{+/-}$ mice, we next conducted in vitro assays to characterize this observation mechanistically. Given that conventional T lymphocytes (Tcon) require signaling through both TCR and CD28 for activation (reviewed in Tivol et al. 1996), we next stimulated MACs purified, CD4$^+$CD25$^-$ T lymphocytes with antibodies specific to CD3 and CD28 ($\alpha$CD3/$\alpha$CD28), in vitro. After 72 hours of incubation, $\alpha$CD3/$\alpha$CD28 activated CD4$^+$ T lymphocyte populations were greater than 70% CD25$^+$, independent of SOCS1 expression (FIG. 2A). In similar fashion, $\alpha$CD3/$\alpha$CD28 treatment mediated comparable CD69 up-regulation in both SOCS1$^{+/-}$ and littermate control T lymphocytes (FIG. 2A). Notably, however, whereas $\alpha$CD3 treatment mediated limited CD25 high expression in SOCS1 sufficient CD4$^+$ T cells, 45% of SOCS1$^{+/-}$ counterparts had high levels of CD25 expression with $\alpha$CD3 treatment alone (FIG. 2A). Moreover the percentage of CD69$^{hi}$ was also greater in $\alpha$CD3 treated SOCS1$^{+/-}$CD4$^+$ T lymphocytes compared to SOCS1$^{+/+}$CD4$^-$ controls (FIG. 2A).

Since clonal expansion (e.g., proliferation) occurs subsequent to CD4$^+$ T cell activation (Mondino and Jenkins 1994), we then assessed T cell proliferation under $\alpha$CD3/$\alpha$CD28 treatment or $\alpha$CD3 alone. Consistent with CD25 and CD69 frequencies (FIG. 2A), SOCS1$^{+/-}$ CD4$^+$ T lymphocyte proliferation (as assessed by CFSE, absolute cell counts, and $^3$H thymidine incorporation) was statistically indistinguishable to that of littermate controls when stimulated by $\alpha$CD3/$\alpha$CD28, (FIG. 2B). Strikingly, however, $\alpha$CD3 treatment alone mediated significantly more proliferation of SOCS1$^{+/-}$ CD4$^+$ T lymphocytes as depicted by a higher percentage of CFSE$^{lo}$ cells (54.6±0.9 vs. 34.0±3.2), 3 fold higher absolute cell numbers, and 6 fold greater $^3$H thymidine incorporation (FIG. 2B). In summary, these results indicate that SOCS$^{+/-}$ CD4$^+$ T cells have a reduced threshold for activation and clonal expansion in vitro.

Example 3

SOCS1$^{+/-}$ CD4$^+$ T Cells Exhibit Reduced P-Akt Requirement for Activation

As SOCS1$^{+/-}$CD4$^+$ T lymphocytes exhibited significant activation and proliferation in the absence of CD28 stimulation, we next examined Akt activation, which is involved in signaling downstream of CD28 (Parry et al. 1997). Strikingly, although we observed significantly more proliferation and activation of SOCS1$^{+/-}$ CD4$^+$ T lymphocytes under $\alpha$CD3 treatment alone, Akt phosphorylation subsequent to $\alpha$CD3 treatment was significantly reduced in SOCS1$^{+/-}$ mice compared to littermate controls (FIG. 2C). The differences in p-Akt were observed in spite of comparable amounts of total Akt under $\alpha$CD3 treatment (FIG. 2C). Consistent with the activation and proliferation results noted previously (FIG. 2A, FIG. 2B), p-Akt levels were indistinct between SOCS1$^{+/-}$ and WT cells incubated with $\alpha$CD3/$\alpha$CD28 (FIG. 2C). Together, these results suggest a limited requirement for CD28 co-stimulatory signals in the CD4$^+$ T lymphocyte phenotype present in lupus-prone, SOCS1$^{+/-}$ mice.

Example 4

TCR Stimulated SOCS1$^{+/-}$ T Cells Display Heightened IFN$\gamma$ Production

As CD4$^+$ T cell activation is associated with cytokine production, and IFN$\gamma$ production has been associated with lupus onset (Balomenos et al. 1998; Haas et al. 1998; Nakashima et al. 1999; Akahoshi et al. 1999; Karonitsch et al. 2009), we next analyzed IFN$\gamma$ production under CD3 and CD3/CD28 stimulatory conditions. Although IFN$\gamma$ production by SOCS1$^{+/-}$ was consistently higher than WT mice when subjected to $\alpha$CD3/$\alpha$CD28 conditions, distinctions in IFN$\gamma$ production reached profound significance under $\alpha$CD3 treatment, with IFN$\gamma$ levels 4 fold higher in SOCS1$^{+/-}$ lymphocytes compared to those obtained from WT littermates (FIG. 2D). Notably, the production of IFN$\gamma$ by SOCS1$^{+/-}$ T lymphocytes under $\alpha$CD3 treatment alone was comparable to IFN$\gamma$ production by T lymphocytes receiving additional CD28 stimulation (FIG. 2D). Therefore, prior to disease onset, SOCS1 deficiency leads to the development of CD4$^+$ T cells that are hyper-responsive to TCR stimulation—resulting in hyper-activation and abnormal Th1 phenotypic expression.

Example 5

Figure 3:
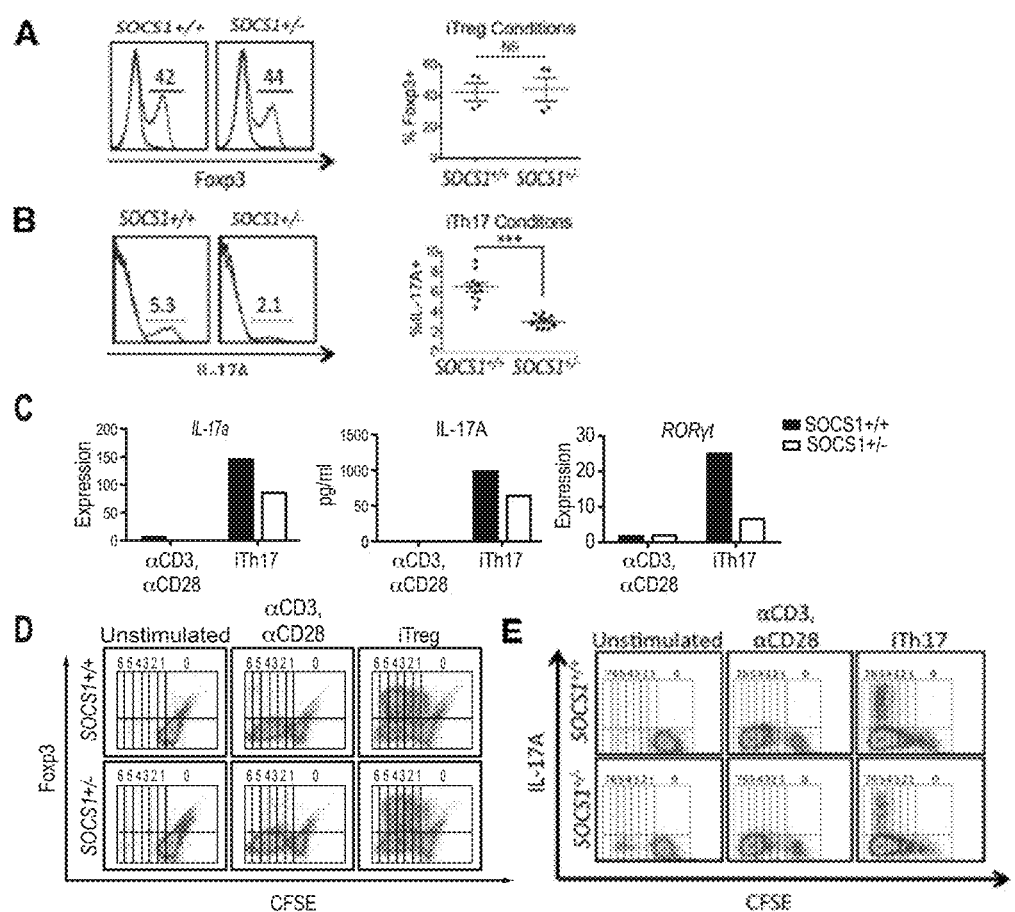
FIGS. 3A-3E. Th17, but not Treg, induction is dysregulated in SOCS$^{+/-}$ CD4$^+$ T lymphocytes.

SOCS$^{+/-}$ Naïve CD4$^+$ T Cells Undergo Normal Treg Induction, but Abnormal Th17 Induction As proper T cell differentiation is critical to the maintenance of immune homeostasis and inhibition of autoimmunity (reviewed in Hirahara et al. 2013), we next investigated the plasticity of SOCS1$^{+/-}$CD4$^+$ T lymphocytes through incubation under regulatory and Th17 inducing conditions. While flow cytometric analysis of Treg induction (as denoted by the frequency of Foxp3$^+$ cells) revealed no difference in Treg induction between SOCS1$^{+/-}$ and WT CD4$^+$ $^T$ cells (FIG. 3A), it is noteworthy that there was a significant reduction in the percentage of SOCS1$^{+/-}$IL-17A$^+$ cells, subsequent to incubation under Th17 inducing conditions (FIG. 3B). Reduced Th17 differentiation of SOCS1$^{+/-}$ lymphocytes was confirmed by qPCR and ELISA, which showed reduced levels of IL-17A message, secreted IL-17A protein, and decreased levels of the Th17 specific transcription factor ROR$\gamma$t (FIG. 3C).

As it has been previously shown that cytokine production and terminal differentiation of lymphocytes are functions of cell division (Gett and Hodgkin 1998), we next assessed whether differences in proliferation contributed to differential IL-17A production. Purified, CFSE labeled CD4$^+$CD25$^-$ cells from either SOCS1$^{+/-}$ or WT littermate controls were cultured under αCD3/αCD28 stimulation, iTreg inducing conditions, iTh17 inducing conditions, or left unstimulated. The treated cultures were subsequently assessed for Foxp3 or IL17 production as a function of proliferation. Treatment with αCD3/αCD28 alone failed to mediate either extensive Foxp3 expression, or IL17 production, in either SOCS1$^{+/-}$ or WT lymphocytes (FIG. 3D, 3E). As expected, the induction of Foxp3$^+$ Tregs and Th17 CD4$^+$ T lymphocytes upon incubation with TGF-β alone and TGF-β and IL6, respectively, was consistent with published reports (Mangan et al. 2006; Bedoya et al. 2013) (FIG. 3D, FIG. 3E). Moreover, consistent with results observed in FIG. 3A, the frequencies of Foxp3$^+$CD4$^+$ T lymphocytes were similar, independent of SOCS1 expression and CFSE dilution (FIG. 3D). Although the overall frequency of SOCS1$^{+/-}$ IL-17A$^+$ CD4$^+$ lymphocytes was reduced compared to WT (6.5±0.5 vs. 3.1±0.2; SOCS1$^{+/-}$ vs. WT), dilutions in CFSE, indicative of division cycles, were indistinct (FIG. 3E). Notably, unlike Treg induction, which began independently of proliferation, IL-17A production was not readily apparent until the third division (FIG. 3D vs. FIG. 3E). Taken together, these data indicate that while SOCS1$^{+/-}$ CD4$^+$ T cells have the capacity to undergo normal Treg induction, SOCS1 deficient cells have a reduced capacity to undergo proper Th17 differentiation.

Example 6

Figure 4:
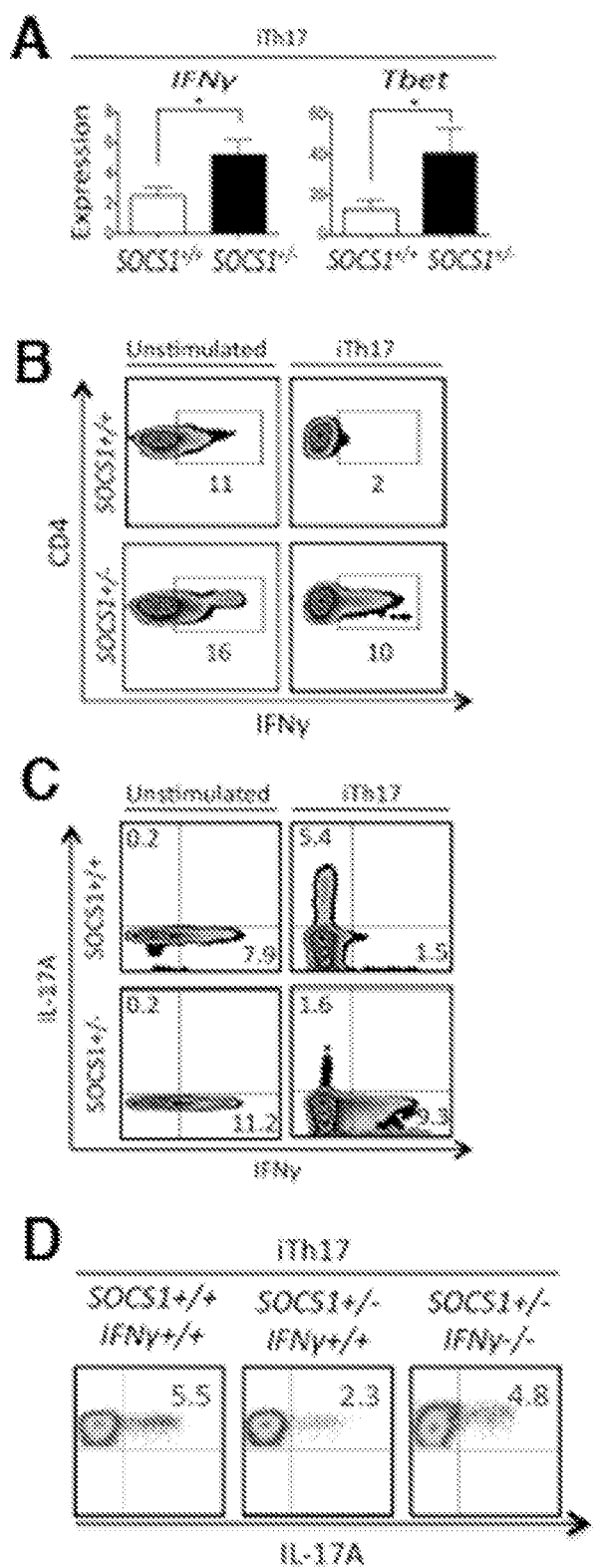
FIGS. 4A-4D. SOCS1$^{+/-}$ CD4$^+$ T cells display Th1 bias under Th17 inducing conditions.

SOCS1$^{+/-}$ CD4$^+$ T Cells Display Heightened IFNγ Expression, Even Under Th17 Inducing Conditions Considering the Th1 bias observed in TCR stimulated SOCS1$^{+/-}$ CD4$^+$ T cells, we hypothesized that the reduced capacity of SOCS1$^{+/-}$ T cells to undergo Th17 differentiation could be due to dysregulated IFNγ signaling. To test this hypothesis, we placed SOCS1$^{+/-}$ or WT cells under Th17 inducing (iTh17) conditions and first assessed mRNA expression of IFNγ and T-bet, the IFNγ promoting transcription factor (Szabo et al. 2002). As can be seen, IFNγ expression was more than 2-fold greater in SOCS1$^{+/-}$ cells in comparison to WT controls (FIG. 4A). In parallel with the heightened IFNγ message expression, T-bet expression was also enhanced more than 2 fold (FIG. 4A). Heightened expression was also seen at the protein level as intracellular staining revealed that un-stimulated SOCS1$^{+/-}$ cells possessed an IFNγ$^+$ cell frequency that was approximately 1.5 fold greater than WT counterparts (FIG. 4B). Additionally, under iTh17 conditions, we noted a 5-fold increase in the population of SOCS1$^{+/-}$ IFNγ$^+$ cells (FIG. 4B). Moreover, the reduction in IFNγ producing WT CD4$^+$ T lymphocytes subsequent to Th17 induction (more than 80%) was not as readily observed in SOCS1$^{+/-}$ under the same conditions (only 38%, FIG. 4B). In addition, the changes in IFNγ and IL17 production were not due to changes in IL17$^+$IFNg$^+$ dual cytokine expressing T lymphocytes (FIG. 4C). Taken together, these results suggest that preferential expression of IFNγ by SOCS1$^{+/-}$ CD4$^+$ T cells inhibits Th17 induction.

To confirm the role of IFNγ in the reduced Th17 differentiation of SOCS1$^{+/-}$ CD4$^+$ T cells, we assessed Th17 differentiation in SOCS1$^{+/-}$ CD4$^+$ T cells taken from SOCS1$^{+/-}$ IFNγ$^{-/-}$ mice. While Th17 differentiation of SOCS1$^{+/-}$ cells resulted in a 2.3% CD4 μL-17A$^+$ population, intracellular staining revealed a 4.8% population in SOCS1$^{+/-}$IFNγ$^{-/-}$ cells, that was statistically indistinct from WT controls (FIG. 4D). Taken together, these data show that preferential expression of IFNγ by SOCS1$^{+/-}$ CD4+ T lymphocytes precludes Th17 differentiation.

Example 7

Figure 5:
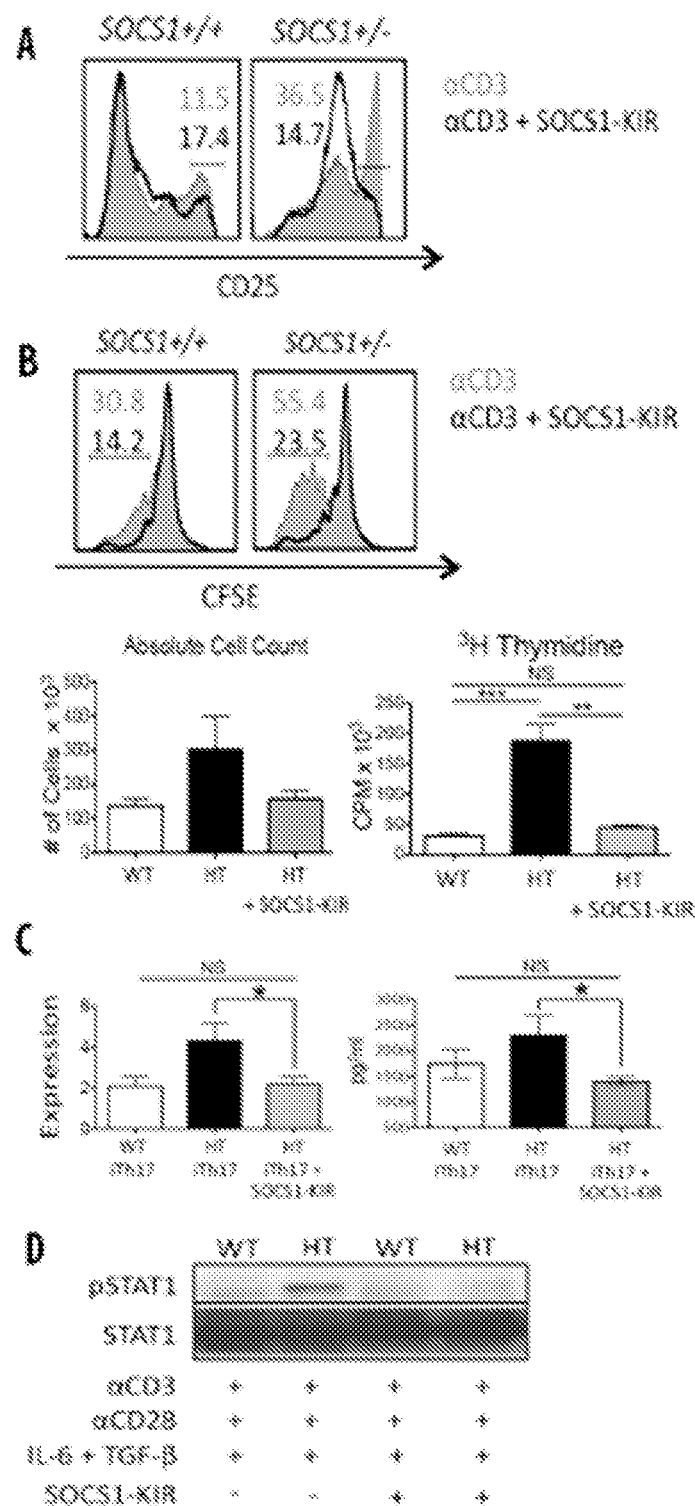
FIGS. 5A-5D. SOCS1-KIR treatment inhibits perturbed SOCS1$^{+/-}$ CD4$^+$ T cell activation, proliferation, and IFN$\gamma$ production.

SOCS1-KIR Treatment Inhibits Aberrant Activation and Proliferation of SOCS1$^{+/-}$ CD4$^+$ T Cells As SOCS1 deficiency in SOCS1$^{+/-}$ CD4$^+$ T lymphocytes results in aberrant activation and proliferation (FIG. 1-FIG. 5), it is possible that partial restoration of SOCS1 signaling can moderate dysregulation. We have previously shown that a peptide able to partially mimic SOCS1 function, SOCS1-KIR, could both regulate immune homeostasis and prevent EAE when administered in vivo (Jager et al. 2011; Collins et al. 2011). We next assessed the ability of SOCS-KIR to reduce the excessive activation observed in SOCS1$^{+/-}$ CD4$^+$ T lymphocytes. As can be seen, SOCS1-KIR was sufficient to inhibit excessive αCD3 mediated CD25 up-regulation by SOCS1$^{+/-}$ CD4$^+$ T lymphocytes, while mediating limited effects on CD25 expression in WT counterparts (FIG. 5A). SOCS1-KIR also reduced proliferation of both WT and SOCS1$^{+/-}$ CFSE labeled T lymphocytes (FIG. 5B). Notably, SOCS1-KIR reduced the activation and proliferation of αCD3 treated SOCS1$^{+/-}$ CD4+ T lymphocytes to levels comparable to WT receiving αCD3 stimulation (FIG. 5B). Absolute cell counts and $^3$H thymidine incorporation confirmed the SOCS1-KIR mediated inhibition of T lymphocyte proliferation (FIG. 5B). Moreover, SOCS1-KIR treatment resulted in a 2-fold reduction in IFNγ mRNA expression and protein production (FIG. 5C). Together, these data show that dysregulated activation and proliferation of SOCS1$^{+/-}$ CD4 T cells, which have significant implications in autoimmune development, are moderated by the SOCS-KIR peptide.

Example 8

SOCS1-KIR Inhibits Excessive STAT1 Signaling Present in SOCS1$^{+/-}$ CD4$^+$ T Cells Under Th17 Inducing Conditions As STAT1α is rapidly phosphorylated upon IFNγ binding to the IFNγ receptor (Greenlund et al. 1995; Schroder et al. 2004) we next evaluated the capacity of SOCS1-KIR to regulate STAT1α phosphorylation under Th17 inducing conditions. Although little STAT1 was phosphorylated in WT CD4$^+$ T lymphocytes cultured under Th17 conditions, phosphorylation of STAT1 was readily apparent in SOCS1$^{+/-}$ CD4$^+$ T lymphocytes (FIG. 5D). Significantly, SOCS1-KIR drastically reduced the enhanced STAT1 activation in SOCS1$^{+/-}$ cells (FIG. 5D). Therefore, the capacity of SOCS1-KIR to normalize IFNγ production is partly through regulation of STAT1 signaling.

Example 9

Reduced SOCS1 Levels Observed in SLE Patients

Figure 6:
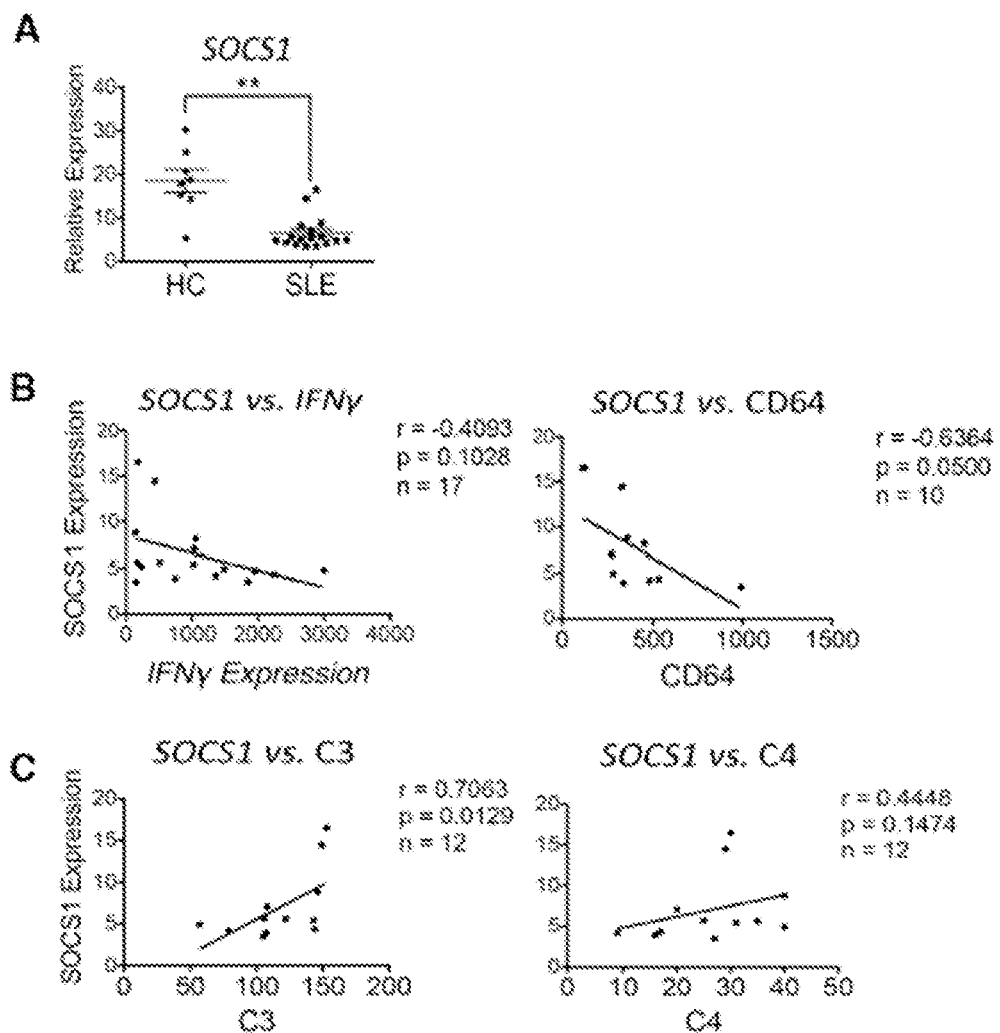
FIGS. 6A-6C. SOCS1 expression is relevant to human SLE.
Figure 9:
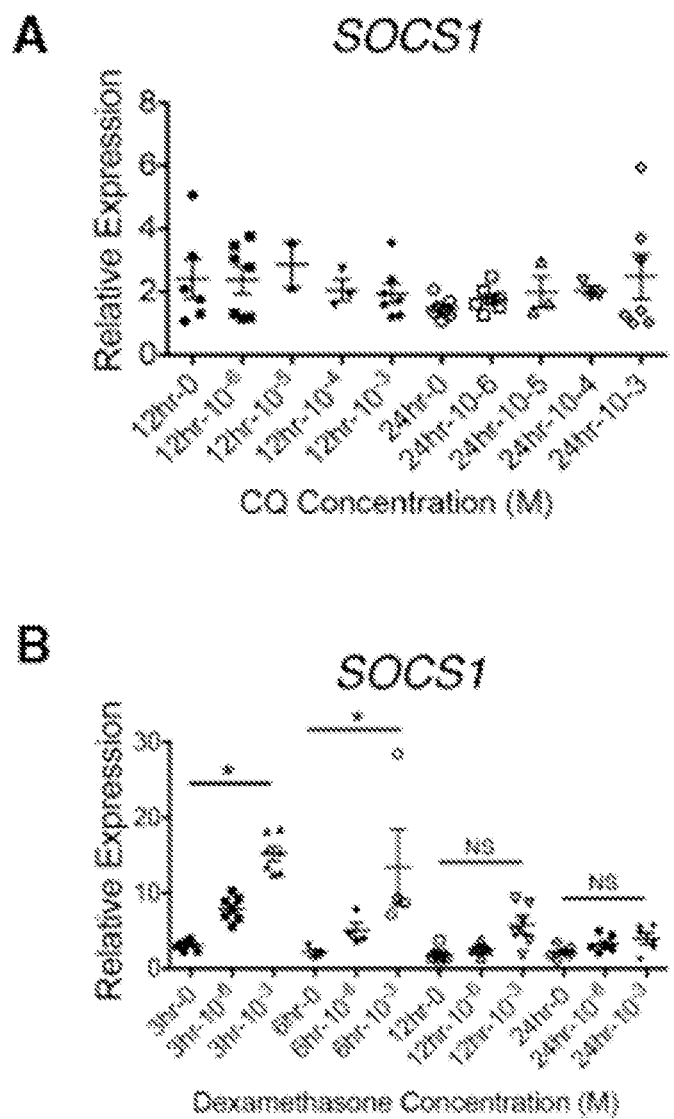
FIGS. 9A and 9B. SOCS1 expression is not affected by chloroquine treatment, but is increased by dexamethasone treatment.
Figure 10:
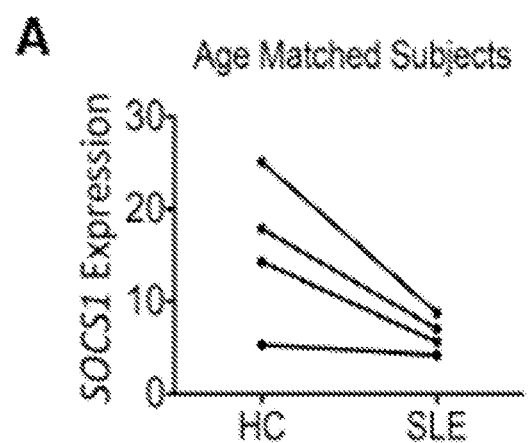
FIGS. 10A and 10B. SOCS1 expression is not correlated with age or SLEDAI. PMBCs were isolated from whole blood taken from SLE patients or healthy controls (HCs) and SOCS1 expression was measured via qPCR, relative to GAPDH.

Although SOCS1 deficiency has been associated to lupus-like pathology in mice (Sharabi et al. 2009; Fujimoto et al. 2004), clinical relevance to this observation in human SLE is less clear. Therefore, to determine whether differences in SOCS1 expression are relevant to human SLE, we assessed SOCS1 expression in peripheral blood mononuclear cells (PBMCs) taken from SLE patients and healthy controls. Although anti-malarials and glucocorticoids are common standard of care medications used to treat SLE (reviewed in Gurevitz et al. 2013), their effects on the modulation of SOCS1 expression in human leukocytes are unknown. Therefore, prior to selecting our patient population, we treated healthy control PBMCs with an antimalarial, chloroquine, and a glucocorticoid, dexamethasone, in vitro and assessed SOCS1 expression. Our pilot study revealed that SOCS1 expression was affected by dexamethasone but not chloroquine (FIG. 9). As such, patients prescribed glucocorticoids were excluded from our study. Strikingly, as can be seen in FIG. 6, SOCS1 mRNA expression was significantly decreased in SLE patients in comparison to healthy controls (FIG. 6A). The differences in SOCS1 expression were likely not due to age, as deficiencies in SOCS1 expression were readily observed in SLE patients compared to age-matched controls (FIG. 10A).

Given that both type I and type II IFNs have been shown to play a key role in the immunopathogenesis of human SLE, and that SOCS1 is a critical regulator of the signaling of these cytokines (Takahashi et al. 1996; Balomenos et al. 1998; Piganis et al. 2011; Alexander et al. 1999; Santiago-Raber et al. 2003), we next investigated whether SOCS1 expression was related to IFNγ and/or monocyte CD64 expression (which is a marker for the type I IFN signature in SLE patients (Li et al. 2010)). While no significant correlation was observed between SOCS1 and IFNγ, a strong negative correlation was noted when SOCS1 was correlated with monocyte CD64 (FIG. 6B). Notably, the patient with the lowest SOCS1 expression displayed the highest CD64 (FIG. 6B), indicating that SOCS1 expression is indeed related to the pathogenic type I IFN signature observed in SLE patients.

We next investigated whether SOCS1 expression was associated with disease activity, as defined by SLE disease activity index (SLEDAI) scores, and serum complement component 3 (C3) and serum complement component 4 (C4) levels. C3 and C4 levels were examined because decreases in free complement molecules in serum are indicative of increased levels of immune complexes and disease activity (reviewed in Pickering and Walport 2000). Though there was no correlation between SOCS1 and SLEDAI scores (FIG. 10B) or between SOCS1 and C4 levels (FIG. 6C), a strong positive correlation was observed between SOCS1 and C3 (FIG. 6C). Notably, the patients with the two highest SOCS1 expression levels displayed the lowest CD64 mean fluorescent intensities and possessed the highest C3 levels (FIG. 6B vs. FIG. 6C). Given that studies involving SLE patients and murine models of the disease have shown that type I IFNs play significant role in immune complex formation (Santiago-Raber et al. 2003; Ronnblom et al. 1991; Jorgensen et al. 2007; Nacionales et al. 2007), the observation that SOCS1 expression is highest in patients with both a low type 1 IFN signature and a high C3 level suggests that SOCS1 may be a key molecule involved in preventing excessive immune complex formation in SLE patients through regulation of type 1 IFN signaling. Taken together, these results strongly implicate a role of SOCS1 in the prevention of the autoimmune pathology observed in human SLE patients.

Example 10

Cytokine dysregulation and T lymphocyte effector function imbalances significantly contribute to SLE onset and progression. Foundational studies, including the classical MRL lupus model and many human SLE studies have outlined the importance of CD4$^+$ T cells in both autoantibody production and glomerulonephritis (Stekman et al. 1991; Desai-Mehta et al. 1996; Mohan et al. 1999; Vratsanos et al. 2001; Bouzahzah et al. 2003). Significantly, several murine studies have implicated deficiencies in SOCS1, which regulates cytokine production and T lymphocyte effector functions, with lupus progression (Sharabi et al. 2009; Fujimoto et al. 2004; Hanada et al. 2003). However the role of SOCS1 in the regulation of lupus-associated T lymphocyte abnormalities is less clear. In this study, we have shown that SOCS1 regulates T lymphocyte activation and effector functions in SOCS1$^{+/-}$ mice, which develop lupus-like pathology. Moreover, we show that SOCS1 deficiency is strongly correlated to human lupus disease.

It is well accepted that although T cells possessing TCR bearing specificity to self are eliminated through central tolerance, nevertheless potentially self-reactive T lymphocytes evade negative selection and persist in the periphery (Picca et al. 2006). In this study we show that SOCS1-specific aberrations in CD4$^+$ T lymphocytes are evident within the periphery of SOCS1$^{+/-}$ mice as opposed to the thymus, thus implicating a peripheral tolerance defect. Prior to anti-DNA autoantibody production, activated CD4$^+$ T cells readily accumulated in the periphery of SOCS1$^{+/-}$ lupus-prone mice. Significantly, peripheral accumulation of T lymphocytes is also readily present in the classical MRL lupus model (Jabs et al. 1992). Moreover, CD4$^+$ T cells in murine and human lupus are known to display a hyper-activated phenotype, which contributes to pathogenic autoantibody production (Stekman et al. 1991; Desai-Mehta et al. 1996; Mohan et al. 1999; Vratsanos et al. 2001; Bouzahzah et al. 2003). Our results here expand upon those previous studies, by showing that decreased levels of SOCS1 expression are sufficient to mediate both lymphoaccumulation and CD4$^+$ T lymphocyte hyper-activation.

The peripheral accumulation of CD4$^+$ T lymphocytes in SOCS1$^{+/-}$ mice and rodent models of SLE underscores the fact that peripheral tolerance mechanisms must be in place to inhibit the onset of autoimmune diseases such as SLE. In addition to TCR stimulation, the additional requirement of co-stimulation in order to obtain full activation of naïve CD4 T lymphocytes serves to limit aberrant peripheral activation and autoimmune events (reviewed in Tivol et al. 1996). Engagement of the CD28 receptor by APC associated B7 molecules is one of the best characterized co-stimulatory interactions (Mondino and Jenkins 1994). In this study we show that under conditions of limited SOCS1 expression, dependence on the CD28 pathway for full CD4$^+$ T lymphocyte activation is significantly diminished. This was reflected not only in significant activation, in the absence of CD28 stimulation, but also in the diminished role of activated Akt in the activation process. It is well established that T cell activation is abnormal in lupus (Stekman et al. 1991; Desai-Mehta et al. 1996; Mohan et al. 1999; Vratsanos et al. 2001; Bouzahzah et al. 2003; Zielinski et al. 2005). In addition, previous studies have shown that SOCS1$^{-/-}$ CD28$^{-/-}$ mice possessed high levels of anti-dsDNA antibodies (Hanada et al. 2003). Although this result was interpreted to mean that T lymphocyte help was not required, an alternative interpretation, supported by this study, is that CD28 co-stimulation is not required for B cell help mediated by SOCS1 deficient T lymphocytes. Notably, several studies implicate the phosphatidylinositol 3 Kinase (PI3K)/Akt pathway in regulating the balance between conventional T lymphocyte (Tcon) effector functions and Foxp3 Treg development (Cheng et al. 2011; Pierau et al. 2009). As these studies show a reduced threshold for T lymphocyte activation under conditions of SOCS1 deficiency, these findings extend upon previous studies by implicating a role of SOCS1 deficiency in the hyper-activated CD4+ T lymphocyte population characterized in both SLE patients and classical murine lupus models.

An important hallmark of a properly functioning immune system is the generation of a cytokine milieu sufficient to mediate the elimination of distinct microorganisms or cancerous cells. Significantly, an important characteristic of an autoimmune promoting immune system is the production of a dysregulated cytokine milieu (reviewed in Yoshimura et al. 2012). For example, CD4+ T cells in lupus have been shown to display enhanced IFNγ production due to a Th1 bias (Takahashi et al. 1996). Our studies show that STAT1 is highly activated in SOCS1+/− CD4+ T lymphocytes, even under Th17 inducing conditions. As it has been previously shown that IL-6 inhibition of Th1 differentiation is mediated by SOCS1 (Diehl et al. 2000), it appears likely that SOCS1 expression also serves to regulate IL-17 production in environments with IFNγ present.

Dysregulated regulatory T cell (Treg) function has been strongly implicated in lupus onset (Valencia et al. 2007; Suen et al. 2009; Yan et al. 2008). In this study we show that SOCS1 expression did not influence the induction of Foxp3+ Tregs. This was in spite of the Th1 bias present in SOCS1+/− CD4+ T lymphocytes. This finding is novel, given the conflicting studies regarding the role of Th1 related cytokines and Treg development (Caretto et al. 2010; Feng et al. 2011). Notably we have previously shown that the lethal IFNγ mediated auto-inflammatory disease that occurs in SOCS1−/− mice was correlated with a decreased peripheral Treg population (Collins et al. 2011). Moreover, it was shown by the Yoshimura group that SOCS1−/−Foxp3+ Tregs, lack suppressor function and can be induced to produce the inflammatory cytokines IFNγ and IL-17 (Takahashi et al. 2011). It is tempting to speculate SOCS1 expression regulates the stability of the Treg lineage, even with heterozygous expression. Additional studies are necessary to further characterize the role of SOCS1 in peripheral Treg homeostasis and function.

The identification of genetic defects involved in SLE onset/progression is critical, as therapeutic strategies incorporating this knowledge can then be utilized for treatment development. Genetic defects can be mediated through gene polymorphisms or nonfunctional alleles. Although haplotype expression of particular genes may not be generally associated with dysregulated immunity, it is clear that, whereas complete deficiency of the SOCS1 gene in rodent models results in lethality, heterozygous expression mediates lupus-like pathology. Significantly, we show that SOCS1 production by PBMCs is significantly lower in SLE patients compared to healthy controls. To date, there have been two studies examining SOCS1 levels in lupus patients with conflicting results (Tsao et al. 2008; Chan et al. 2010). One study found no differences in SOCS1 with respect to lupus (Tsao et al. 2008), while a second study found higher levels of SOCS1 within patients with significant disease (Chan et al. 2010). Although it remains unclear why the results of these two studies differ from the results acquired in our study, it is likely that differences in samples sizes and patient exclusionary criteria contribute. As our pilot study (and a recently published murine study (Bhattacharyya et al. 2011)) showed that glucocorticoids increase SOCS1 expression, in contrast to the previous studies, we excluded patients that were prescribed glucocorticoids.

We also show that SOCS1 expression is inversely proportional to SLE disease as measured by C3 levels and type 1 interferon signature. It is likely that a statistical correlation could not be established between C4 and SOCS1 because genetic deficiencies in CD4, independent of inflammation, are common in lupus patients (reviewed in Pickering and Walport 2000).

Elucidation of the mechanisms by which lupus pathogenesis occurs is critical for the development of treatment strategies, which target the specific immune dysregulation. We show that a peptide mimic of the kinase inhibitory region of SOCS1, SOCS1-KIR, was sufficient to inhibit aberrant T cell activation and IFN signaling. SOCS1-KIR binds to and inhibits the function of JAK2, making it a natural JAK2 tyrosine kinase inhibitor. Studies are currently underway to determine whether chemical JAK2 kinase inhibitors used to treat patients with myeloproliferative neoplasms, may have efficacy in the treatment of SLE (Pardanani et al. 2011; Wang et al. 2010). SOCS1 limits the signaling of several cytokines involved in lupus onset including the cytokines interferon gamma (IFNγ), interferon α(IFNα), B lymphocyte activating factor (BLyS), and interleukin 6 (reviewed in Alexander 2002). As humanized monoclonal antibodies against BLyS, IFNα, and IFNγ are in clinical trials for treating lupus (Ledford 2011), it is tempting to speculate that strategies focused on enhancing SOCS1 could work in synergy with antibody or standard of care treatments for SLE—especially since SOCS1 expression is reduced in SLE patients.

TABLE 4

Mouse (mus) and Human (hu) mRNA Primer Sequences and Annealing Temperatures

| mRNA | Forward Primer | Reverse Primer | Annealing Temperature (° C.) |
|---|---|---|---|
| mus-Actin | 5'-CCTTCCTTCTTG GGTATGGA-3' (SEQ ID NO: 9) | 5'-GGAGGAGCAATG ATCTTGAT-3' (SEQ ID NO: 10) | 55 |
| mus-IFNγ | 5'-AACTATTTTAAC TCAAGTGGCAT-3' (SEQ ID NO: 11) | 5'-AGGTGTGATTCA ATGACG-3' (SEQ ID NO: 12) | 55 |
| mus-Tbet | 5'-GGGAGAACTTTG AGTCCA-3' (SEQ ID NO: 13) | 5'-GAAGGTCGGGGT AGAAA-3' (SEQ ID NO: 14) | 50 |
| mus-IL-17A | 5'-ACTCTCCACCGC AATGA-3' (SEQ ID NO: 15) | 5'-CTCTTCAGGACC AGGAT-3' (SEQ ID NO: 16) | 55 |
| mus-RORγt | 5'-ACAGCCACTGCA TTCCCAGTTT-3' (SEQ ID NO: 17) | 5'-TCTCGGAAGGAC TTGCAGACAT-3' (SEQ ID NO: 18) | 63 |
| mus-SOCS1 | 5'-GACACTCACTTC CGCACCTT-3' (SEQ ID NO: 19) | 5'-GAAGCAGTTCCG TTGGCACT-3' (SEQ ID NO: 20) | 57 |
| hu-GAPDH | 5'-TGCACCACCAAC TGCTTAG-3' (SEQ ID NO: 21) | 5'-GAGGCAGGGATG ATGTTC-3' (SEQ ID NO: 22) | 59 |
| hu-SOCS1 | 5'-GGGAGCGGATGG GTGTAGG-3' (SEQ ID NO: 23) | 5'-AGAGGTAGGAGG TGCGAGTTC-3' (SEQ ID NO: 24) | 59 |
| hu-IFNγ | 5'-TGACCAGAGCAT CCAAAAGA-3' (SEQ ID NO: 25) | 5'-CTCTTCGACCTC GAAACAGC-3' (SEQ ID NO: 26) | 59 |

Example 11

Figure 11:
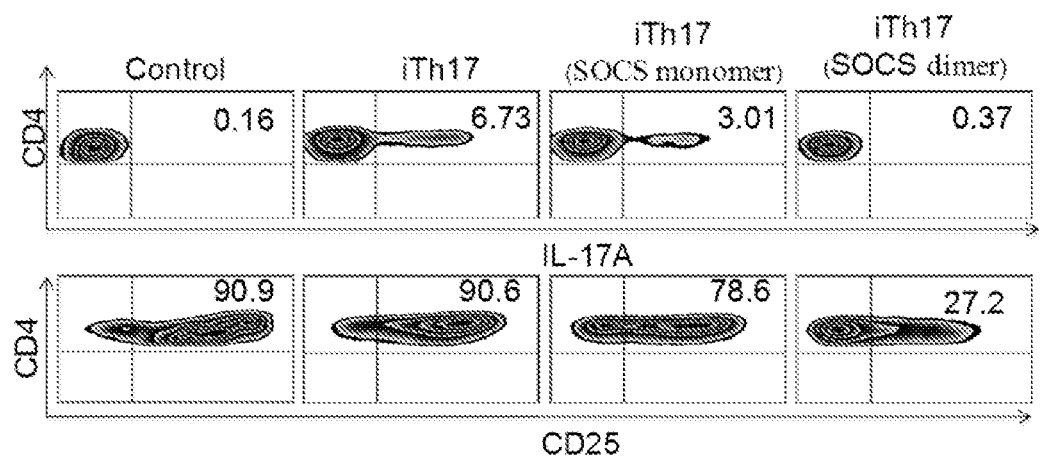
FIG. 11. SOCS1 dimer is more effective than monomer at inhibitory iTh17 induction. CD4+CD25- T cells from B6 mice were in the presence of Th17 inducing conditions in the presence of SOCS1 monomer or dimer for 5 days. Cells were re-stimulated with PMA, ionomycin, and brefeldin, followed by staining with anti-CD4, anti-IL17, and anti-CD25 antibodies.
Figure 12:
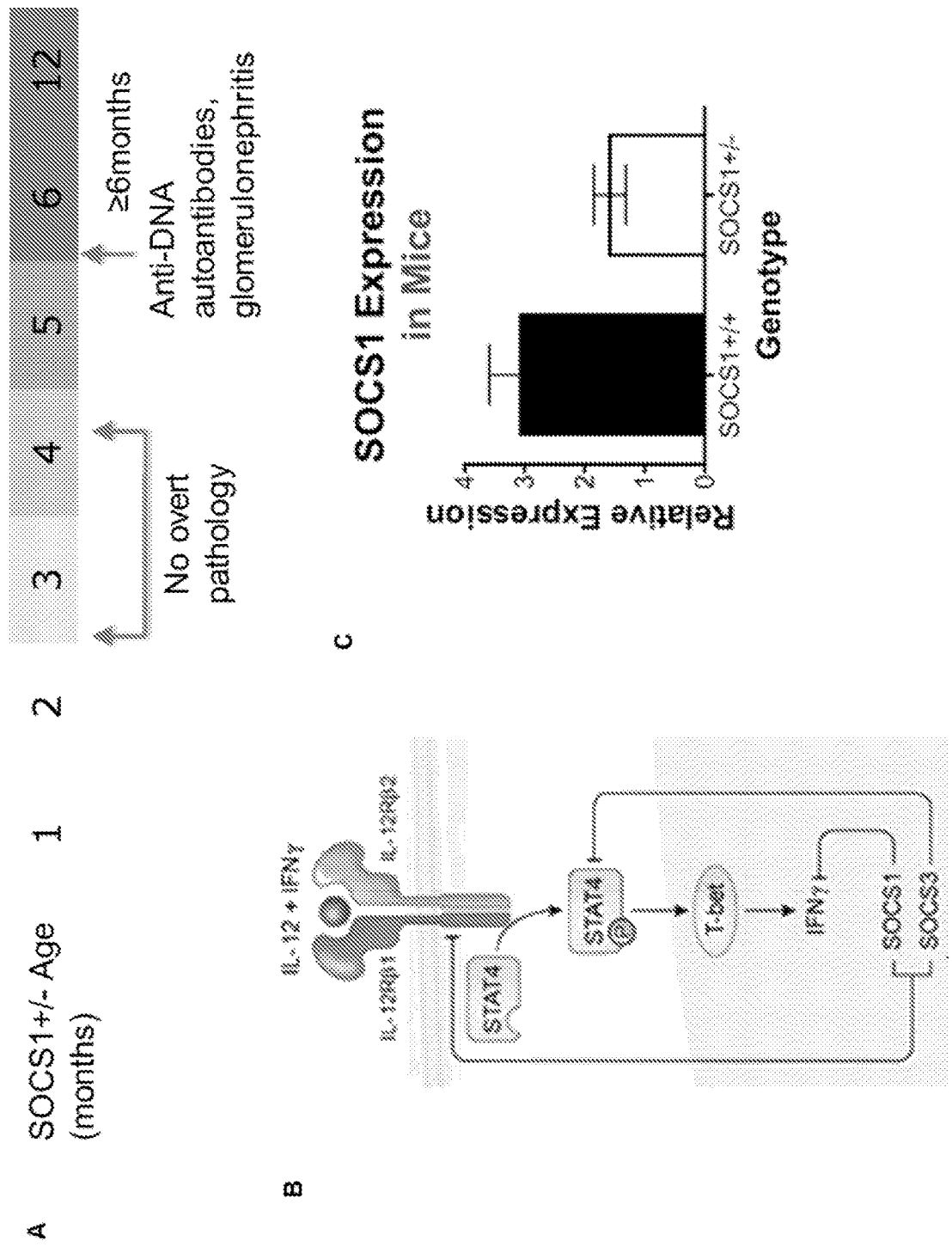
FIGS. 12A-12C. SOCS1+/- mice develop lupus pathology.
Figure 13:
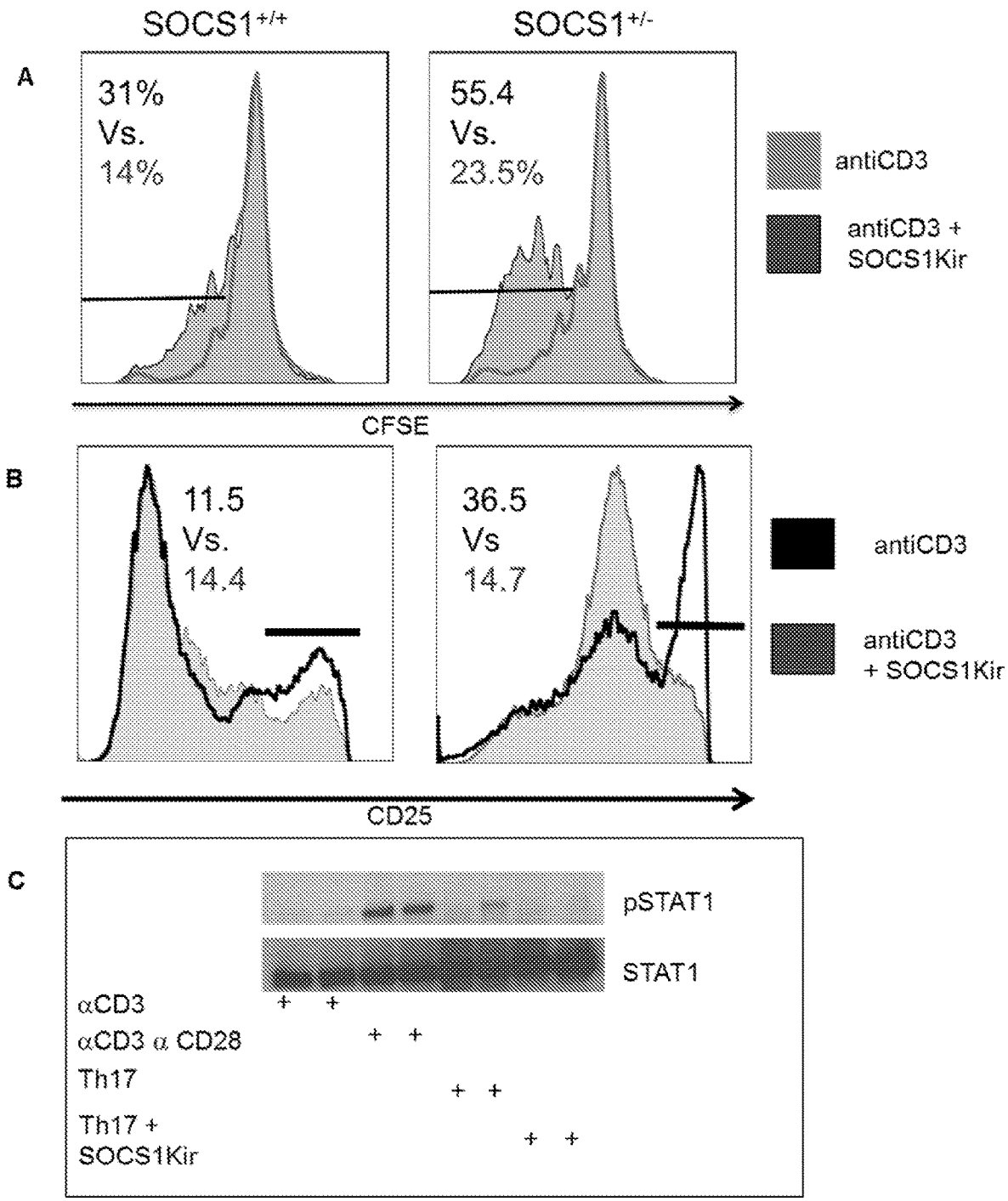
FIGS. 13A-13C. SOCS1-KIR inhibits CD28 independent proliferation and activation of CD4+SOCS1+/- T lymphocytes. SOCS1-KIR treatment inhibits perturbed SOCS1$^{+/-}$ CD4$^+$ T cell activation and proliferation.
Figure 14:
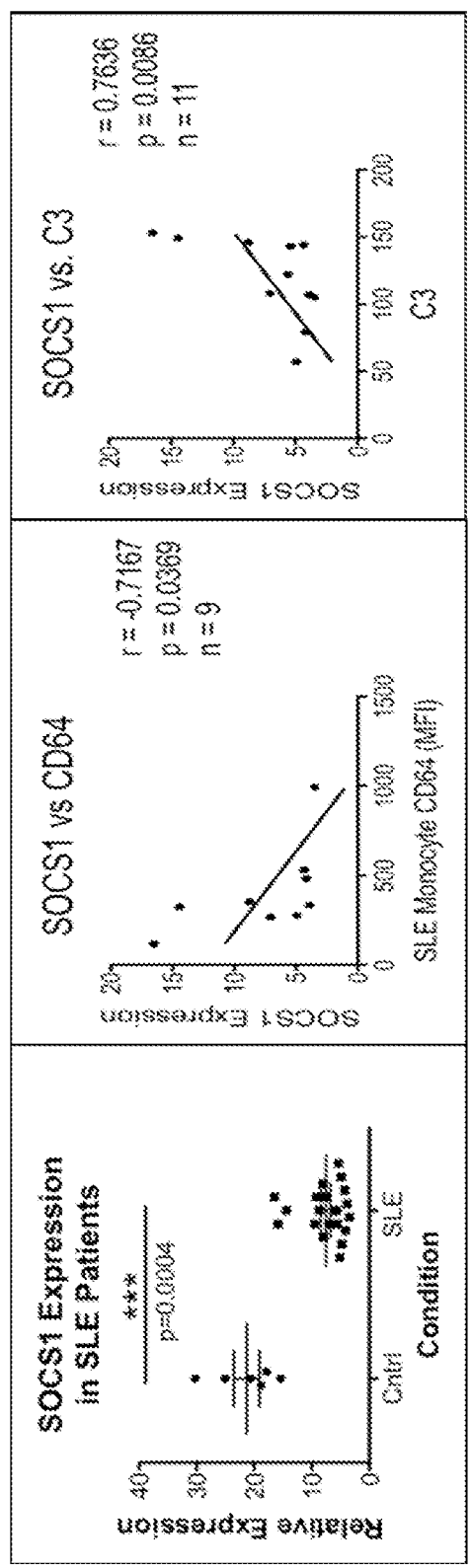
FIG. 14. SOCS1 expression in SLE patient PBMC is deficient, and inversely correlated with disease activity. (Left) PMBCs were isolated from whole blood taken from SLE patients or healthy controls and SOCS1 was measured via qPCR, relative to GAPDH. (middle) For each patient, SOCS1 expression was correlated with monocyte CD64 MFI. (right) SOCS1 expression in patients was also correlated with C3 levels. Results shown as mean±s.e.m. Statistical comparisons between healthy controls and SLE patients were performed using the Mann-Whitney U test (**P<0.005). Spearman's correlation was chosen for statistical analyses. MFI=Mean Fluorescent intensity.
Figure 15:
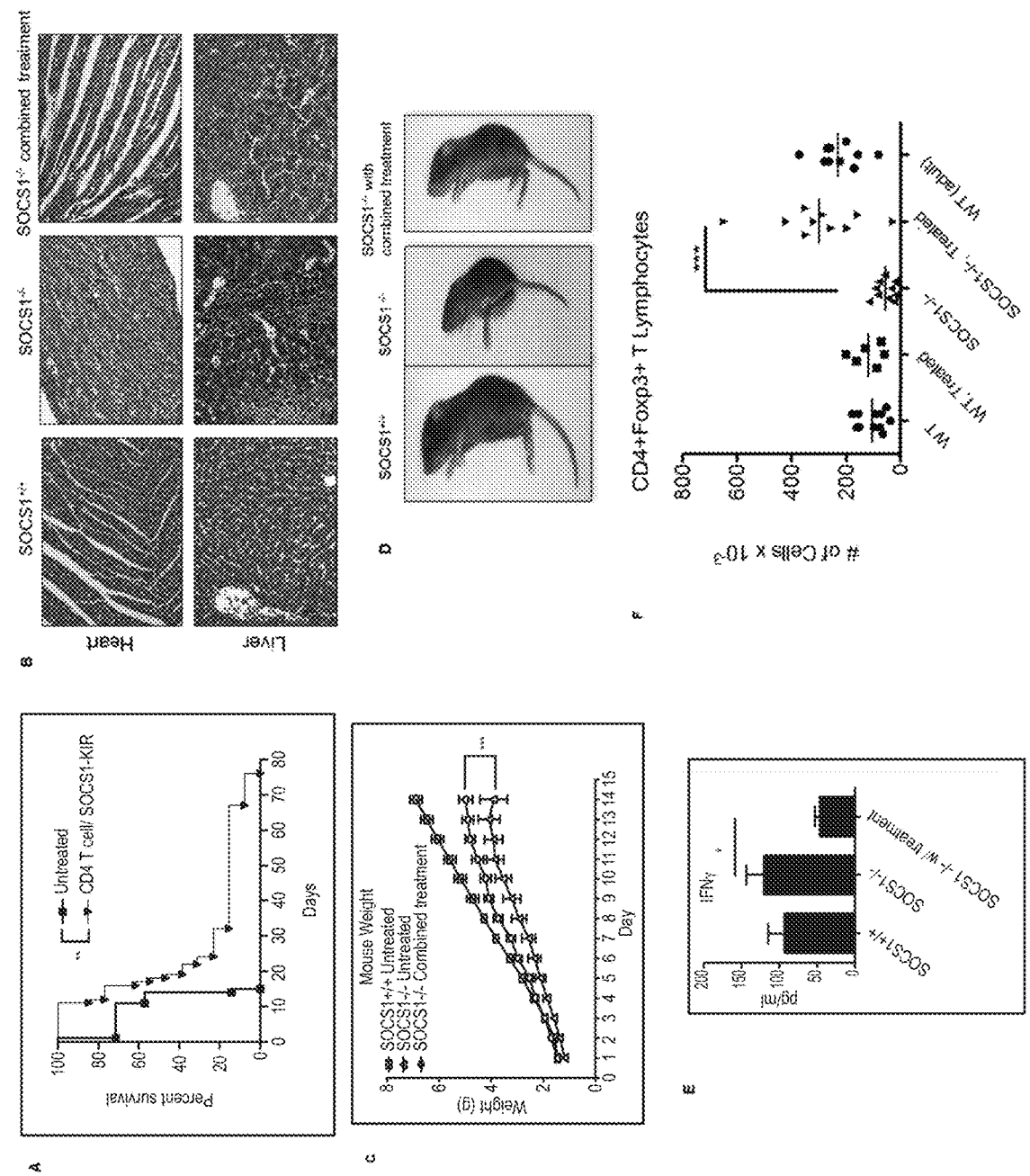
FIGS. 15A-15F. SOCS1-KIR inhibition of lethal inflammatory pathology in SOCS1-/- mice is correlated to enhanced regulatory T cell homeostasis.

SOCS1 Dimer is More Effective than SOCS1 Monomer at Inhibiting Th17 Induction and CD4+ T Cell Activation In Vitro Induction of Th17 cells, iTh17, and the effect of treatment on induction is illustrated in FIG. 11. $CD4^+CD25^-$ T cells from C56BL/6 mice were incubated for 5 days at 37° C. under 1) control conditions (anti-CD3 (10 µg/ml), anti-CD28 (1.5 µg/ml)); 2) Th17 inducing conditions (anti-CD3, anti-CD28, IL-6 (20 ng/ml), TGF-β (5 ng/ml)); 3) Th17 inducing conditions with SOCS1 monomer (20 µM), or Th17 inducing conditions with SOCS1 dimer (20 µM). Following a 5-day incubation, cells were re-stimulated with phorbol myristic acetate (PMA) (50 ng/ml), ionomycin (1 µM), and brefeldin A (10 µg/ml). To assess Th17 differentiation, cells were stained with anti-CD4 and anti-IL-17A antibodies. To assess activation, cells were stained with anti-CD4 and anti-CD25 antibodies.

The data indicate the inhibitory effect of our SOCS mimetics on iTh17 induction. The 16 amino acid mimetic, SOCS1-KIR, encompasses the KIR of SOCS1 (Yoshimura et al. 2012). The SOCS1-KIR dimer used here was synthesized as we indicate for the antagonist above with the poly-glycine linker in symmetrical orientation. The SOCS mimetic dimer had greater inhibitory effects on iTh17 than did the monomer. We expect similar enhanced effects of SOCS dimeric antagonist compared to monomer.

Example 12

Lupus does not occur at birth, implicating that the clinical manifestations observed in lupus are due to the accumulation of pathological autoimmune events, decreases in regulatory mechanisms, or a combination of these processes. Notably, defects in two well established tolerance mechanisms, regulatory T cells (Tregs) and Suppressor of cytokine signaling-1 (SOCS1), have recently been implicated in lupus progression. Significantly, we have shown that SOCS1 is critically involved in the stability of peripheral Tregs. We also showed that a peptide which mimics SOCS1 function can enhance Tregs numbers and prolong the survival of mice with lethal auto-inflammatory disease (see FIGS. 12-15).

Conclusions:

SOCS1+/- mice develop lupus and possibly mimic a SOCS1 deficiency present in human lupus patients.

SOCS1 expression in lupus patients is inversely correlated to disease activity marker CD64, and directly correlated to C3 complement molecules (which typically decrease with increasing disease activity.

T cells, present in SOCS1+/- mice possess a lower threshold of activation, consistent with other lupus rodent models and PBMCs from lupus patients. Notably, SOCS1-KIR can inhibit aberrant proliferation, CD25 up-regulation, and STAT 1 activation.

Mice deficient in SOCS1 (SOCS1-/-) die of a perinatal auto-inflammatory disease within 3 weeks after birth. The administration of SOCS-KIR peptide combined with CD4 T cells could extend the life of SOCS-/- mice, improve the quality of life (size and overall health improvement), and prevent/delay leukocytic infiltration into heart and liver. Inhibition of perinatal lethality in SOCS1-/- mice is correlated to enhanced peripheral homeostasis of Foxp3+CD4+ Tregs, with 2 week old SOCS1-/- mice possessing comparable absolute numbers of Tregs as adult mice.

Materials and Methods for Examples 13-17

Patients and Clinical Samples.

The UF Institutional scientific research and review board (IRB) on human subjects approved the study protocol. Written informed consent were obtained from all patients and controls in the study. In all, 34 SLE patients and 11 healthy controls were enrolled in the present study (Table 5). All SLE patients fulfilled the 1982 American College of Rheumatology (ACR) revised criteria for SLE (Tan et al. 1982). The patient's age ranged from 22 to 73 years while the health controls age ranged from 27 to 55 years. Healthy controls (N=11) were recruited from the outpatient clinics at the participating institutions. All patients underwent baseline investigations as per clinical requirements. Disease activity was assessed by the SLE disease activity index (SLEDAI) (Bombardier et al. 1992).

TABLE 5

SLE patients included in the study (N = 34)

| Patient No. | Age/Gender | SLEDAI | Prednisone (mg) | Plaquenil (mg) |
| --- | --- | --- | --- | --- |
| 1 | 27/F | 2 | 0 | 0 |
| 2 | 36/F | 2 | 0 | (100 or 300) |
| 3 | 63/F | 4 | 20 | 400 |
| 4 | 53/F | 10 | 20 | 0 |
| 5 | 69/M | 2 | 25 | 200 |
| 6 | 73/F | 2 | 0 | 0 |
| 7 | 31/F | 6 | 0 | 400 |
| 8 | 38/F | ND | 0 | 400 |
| 9 | 28/F | 0 | 0 | 400 |
| 10 | 45/F | 4 | 10 | 400 |
| 11 | 55/F | 10 | 5 | 400 |
| 12 | 62/F | ND | 0 | 400 |
| 13 | 55/F | ND | 0 | 200 |
| 14 | 59/F | 0 | 0 | 400 |
| 15 | 22/F | ND | 20 | 400 |
| 16 | 41/F | 2 | 10 | 400 |
| 17 | 23/F | ND | 5 | 400 |
| 18 | 58/F | 0 | 0 | 0 |
| 19 | 32/F | 0 | 0 | 100 mg Quinacrine |
| 20 | 67/F | 0 | 2.5 | 400 |
| 21 | 39/F | 7 | 0 | 400 |
| 22 | 61/M | ND | 8 | 0 |
| 23 | 61/F | ND | 5 | 400 |
| 24 | 46/F | 0 | 0 | 100 mg Quinacrine |
| 25 | 66/F | 0 | 0 | 200 |
| 26 | 51/F | 4 | 10 | 400 |
| 27 | 66/F | ND | 0 | 400 |
| 28 | 44/F | ND | 4 | 400 |
| 29 | 28/F | 4 | 40 | 400 |
| 30 | 56/F | 2 | 0 | 200 |
| 31 | 44/F | 0 | 0 | 200 |
| 32 | 64/F | 0 | 5 | 400 |
| 33 | 29/F | ND | ND | ND |
| 34 | 18/F | ND | ND | ND |

Preparation of Peripheral Blood Mononuclear Cells (PBMCs) and Total RNA Extraction.

PBMCs were purified from heparinized blood by Ficoll-Hypaque gradient centrifugation. Briefly, whole blood was diluted with PBS (1:1) and gently layered on Ficoll (Lymphocyte Separation Medium; Cellgro, Manassas, Va.). Cells were centrifuged continuously at 400×g for 20 minutes. PBMCs were collected from the interface layer and washed 3 times with PBS. After isolation, PBMCs were lysed with RNA lysis buffer (Promega) and stored at −80° C. until RNA extraction and qPCR protocols were performed.

Reverse Transcription-Polymerase Chain Reaction (RT-PCR).

RT-PCR was performed to determine the transcript levels of SOCS1, SOCS3 and STAT1 genes in PBMCs, relative to GAPDH. In brief, cDNA synthesis was performed using the iQ cDNA synthesis kit (Bio-Rad; Hercules, Calif.). The qPCR was subsequently performed using the iQ SYBR Green Super mix (Bio-Rad) and gene-specific primers for SOCS1, SOCS3, IFN-G and IL-27. The real time RT-PCR reaction was performed on CFX Connect™-Real time system. The PCR for the target gene and GAPDH was duplicated twice for each sample and the results were corrected for GAPDH expression as an internal control. Further the data was analyzed using CFX Manager™ software version 3.0 (Bio-Rad technologies, Inc.).

Western Blot Analysis.

Frozen PMBC cell pellets were thawed and lysed in RIPA lysis buffer (Santa Cruz Technologies, Inc.) followed by protein estimation through BSA 2.0 mg/ml standard curve preparation with Pierce protein assay reagents (Thermo Scientific Product #23209). Equal quantities of proteins were loaded and separated in 4%-12% SDS PAGE gel (Bio-rad) and separated proteins were transferred to nitrocellulose membrane (Bio-Rad Laboratories, Hercules, Calif.). The membranes were then blocked and incubated with polyclonal anti-rabbit antibodies specific to the KIR regions of SOCS1 and SOCS3 (a kind gift from Dr. Howard Johnson Labs, UF), anti-pSTAT1; anti-pERK1/2; anti-pAKT and for total STAT1; ERK1/2 and AKT respectively (Cell signaling). Further probed with appropriate secondary antibodies conjugated to HRP, and visualized with the ECL detection system according to the manufacturer's instruction (Pierce; Thermo Scientifics) The GAPDH was used as a loading control. The results were calculated as densitometry arbitrary units using the J image online software.

Statistical Analysis.

The statistical analysis were achieved by the software Graph Pad prism v.5. Data were presented as mean±standard deviation (SE). Student t-test was used for non-paired samples with a 95% confidence limit. Simple linear regressions and Pearson's correlation were used to measure the correlation among different parameters with a 95% confidence limit. P-value was set at $p<0.05$ to be statically significant.

Example 13

Reduced mRNA and Protein Levels of SOCS1 and SOCS3 in SLE Patients

Figure 16:
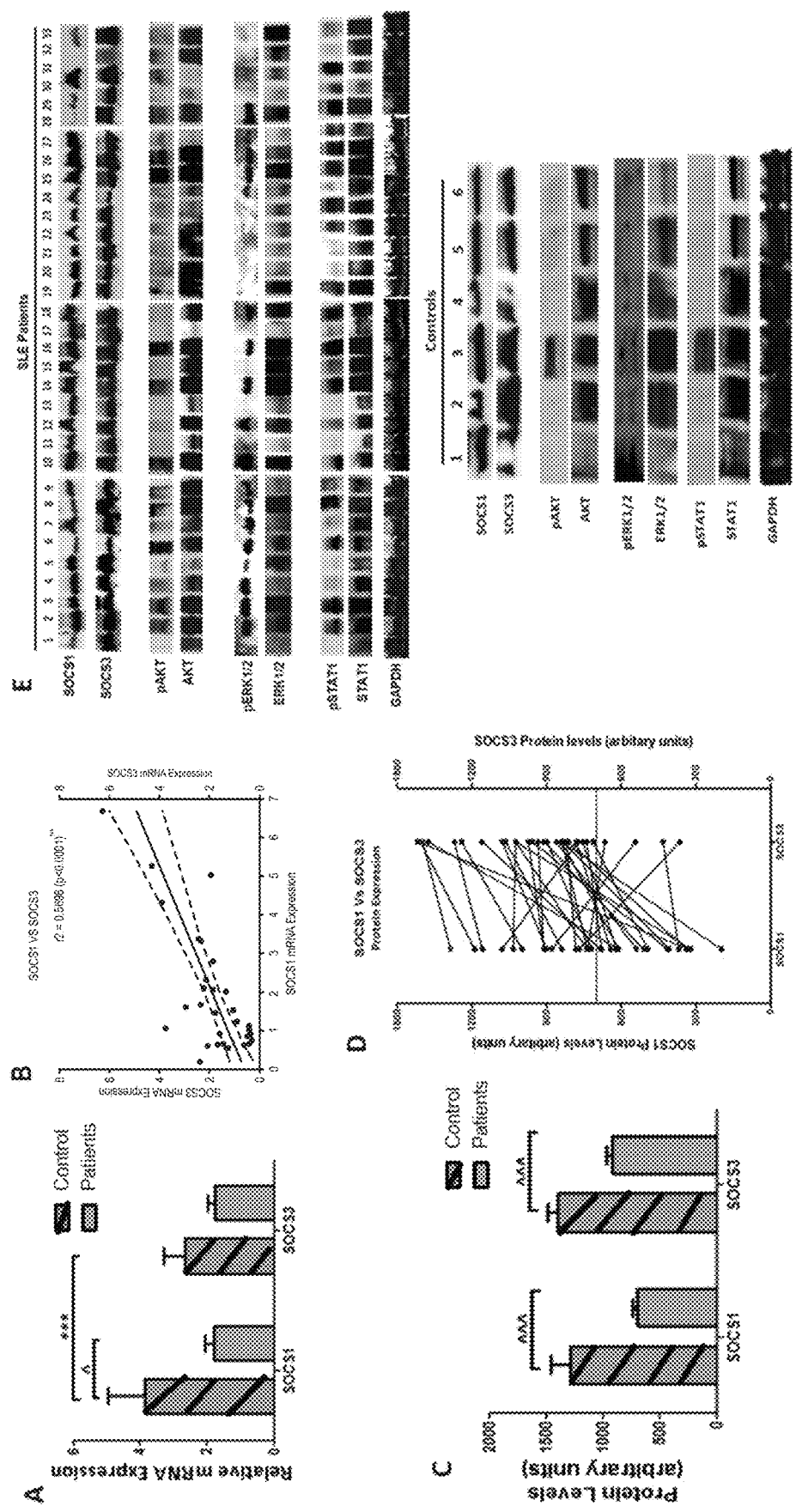
FIGS. 16A-16E. SOCS1 and SOCS3 levels are decreased in SLE patients when compared to healthy controls.

In order to assess whether deficiencies in regulatory proteins could possibly contribute to the well-established cytokine signaling defects present in SLE patients, we first measured SOCS1 and SOCS3 mRNA expression in SLE patients in relation to healthy controls. As can be seen in FIG. 16A, the mean SOCS1 message levels in PBMC isolated from SLE patients was two-fold lower than that of controls ($p\leq0.01$). Although not statistically significant, SOCS3 message levels were also consistently lower in patients compared to controls. In addition, linear regression analysis between SOCS1 and SOCS3 message levels from SLE patients showed a positive correlation ($r2=0.5696$) ($p<0.0001$) between expression levels (FIG. 16B).

As it has been previously shown, in rodent systems, that SOCS mRNA undergoes significant posttranscriptional regulation (Warren S 2004), we next assessed SOCS1 and SOCS3 protein levels from the same patients that we evaluated message expression. Consistent with mRNA levels, the mean SOCS1 protein levels were approximately 3 fold lower in SLE patients compared to controls ($P\leq0.0001$). Notably, reductions in the mean SOCS3 protein levels present in the PBMC of SLE patients did reach statistical significance when compared to controls (FIG. 16C) ($P\leq0.001$). Analysis of SOCS1 and SOCS3 mean protein levels, present in healthy controls, again showed comparable levels of the two proteins as denoted by the red dots within FIG. 16D. However, analysis of SOCS1 and SOCS3 protein levels within the peripheral blood of individual SLE patients showed comparable variation. Although 15/24 of the SLE patients has comparable levels of SOCS1 and SOCS3, 6/24 has higher levels of SOCS3 and 3/24 had strikingly higher levels of SOCS1 levels of the two proteins within individuals (FIG. 16D). Together, these results show that SOCS1 and SOCS3 levels are significantly lower in SLE patients compared to controls.

Example 14

Figure 17:
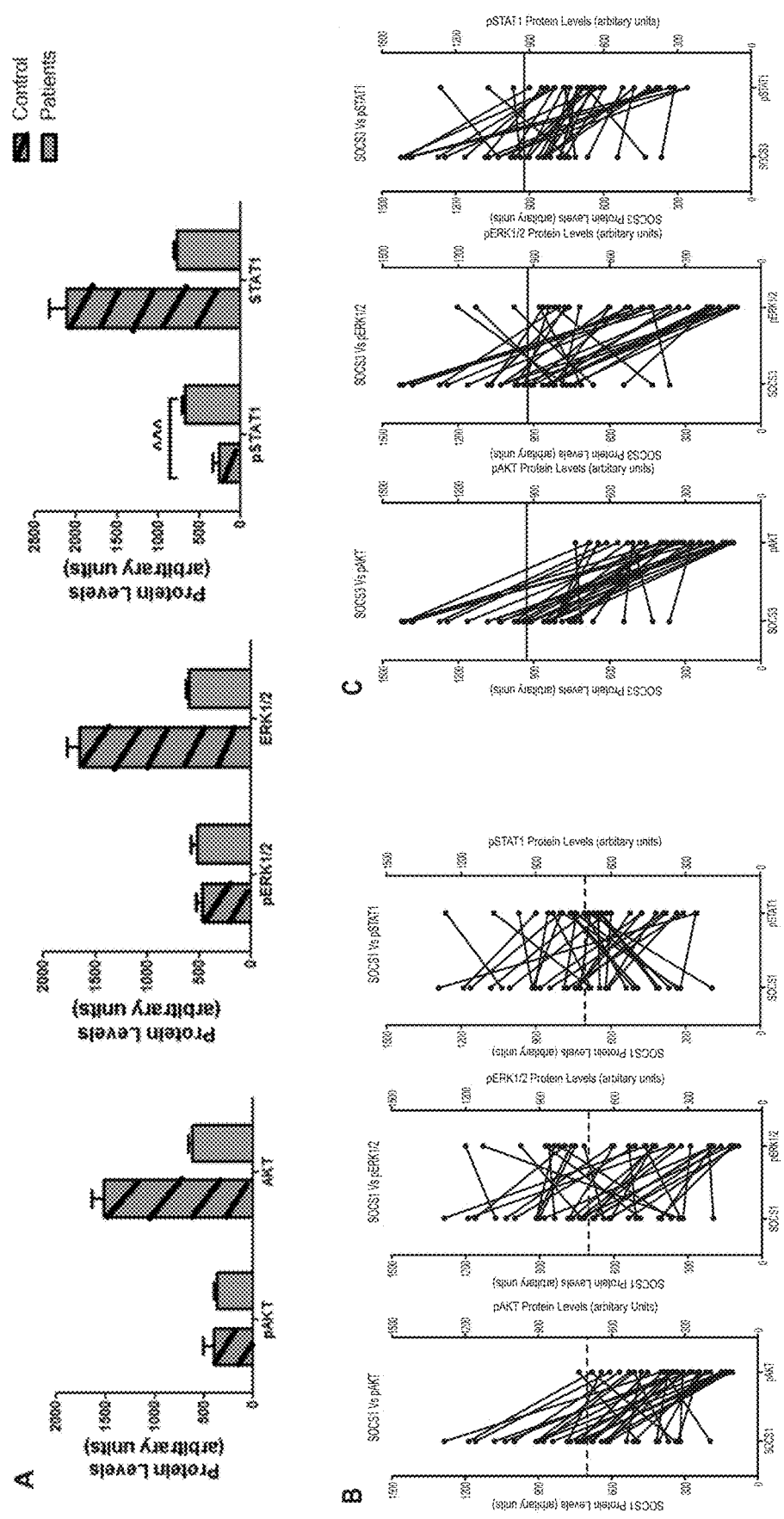
FIGS. 17A-17C. Dysregulated STAT1 activation in SLE patients is correlated SOCS1 deficiency SOCS1 and SOCS3 protein levels in comparison to phosphorylated proteins.

Reduced SOCS1 Protein Levels, in SLE Patients, are Correlated with Enhanced STAT1 Activation We next assessed the activation of the inflammatory markers Akt, Erk1/2, and STAT1 by phosphorylation in SLE patients versus controls. While the average levels of pAkt and pErk1/2 protein levels were statistically indistinct (FIG. 17A as determined by average densitometric analysis of western data present in FIG. 16E), pSTAT1 levels were statistically higher in SLE patients compared to controls. Higher pSTAT1 levels were present in the PBMC of SLE patients compared to controls despite overall higher Akt, Erk1/2, and STAT1 proteins levels in healthy controls (FIG. 17A). In order to assess a relationship between the KIR containing SOCS1 and SOCS3 proteins with the inflammatory markers Akt, Erk1/2, and STAT1; comparisons were performed between the individual SLE patients and the average levels expressed by healthy controls. FIG. 17B shows that healthy controls, 23/26, and 20/26 of the SLE patients, respectively, possessed pAkt and pErk1/2 levels that were negatively associated with SOCS1 and SOCS3 protein levels. Notably, although healthy controls and 22/26 of the SLE patients possessed low pSTAT1 levels and high SOCS3 levels, in 15/26 of the patients pSTAT1 levels were visibly elevated in comparison to SOCS1 levels. Indeed, 57% (8/14) of SLE patients bearing SOCS1 protein levels below the SLE patient mean possessed pSTAT1 proteins levels that were elevated in relation to SOCS1. Together these data suggest that reduced levels of SOCS1, in SLE patients is correlated to enhanced activation of STAT1.

Example 15

Figure 18:
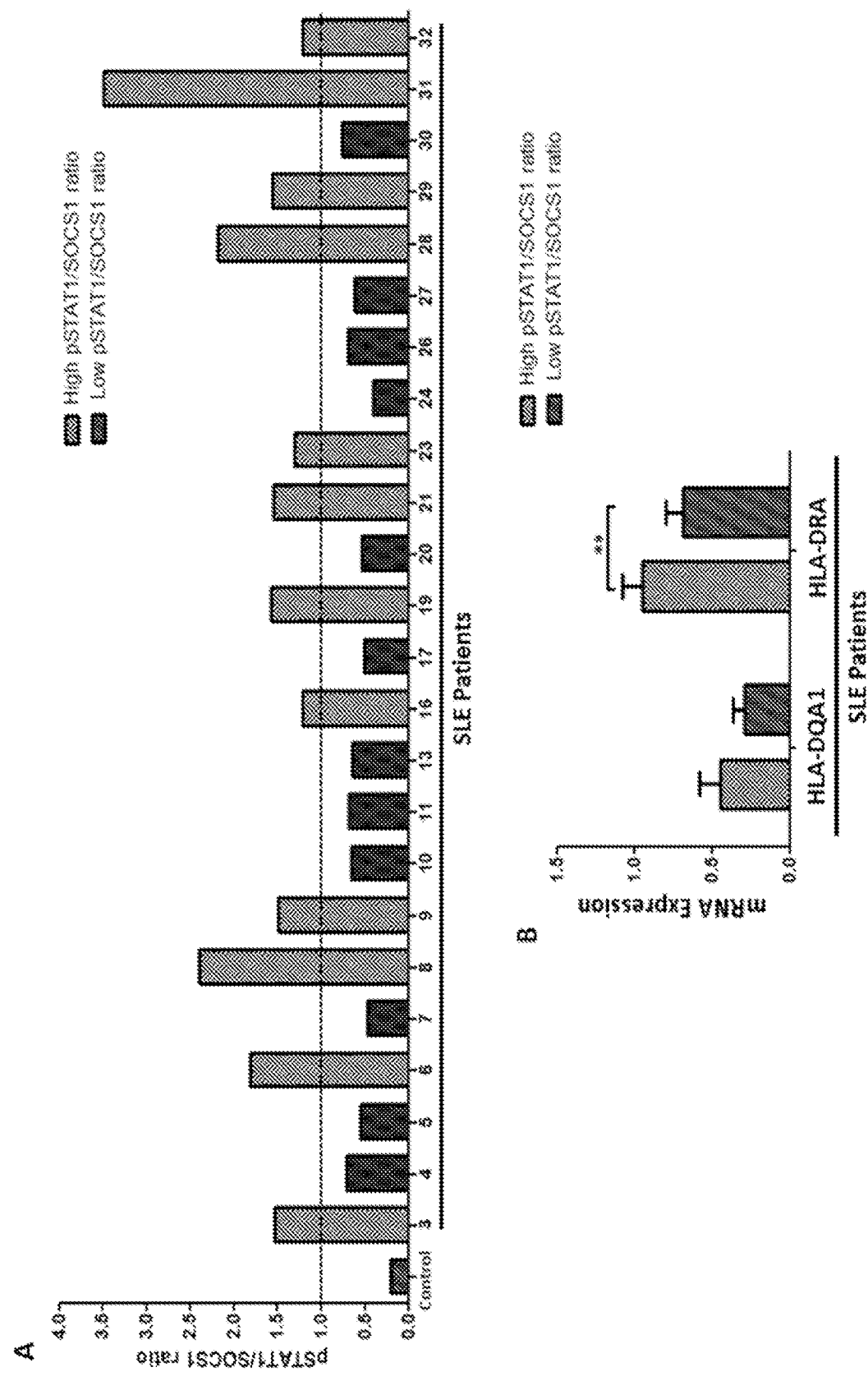
FIGS. 18A-18B. Inverted pSTAT1/SOCS1 ratio correlates to significantly enhanced MHC class 1 levels amongst SLE patients.

Inverted pSTAT1/SOCS1 Ratio Correlates to Significantly Enhanced MHC Class 1 Levels Amongst SLE Patients Given that nearly 60% of the SLE patients possessed a striking inverted pSTAT1/SOCS1 ratio, we next sought to examine whether this inverted ratio could have any bearing on immunological dysregulation events associated with lupus pathology. As such, we first identified individual patients from FIG. 17B that possessed pSTAT1/SOCS1 ratios that we greater or lower than 1 (FIG. 18A). We next segregated the SLE patients based on the presence of a pSTAT/SOCS1 ratio of greater or less than 1, followed by the assessment of MHC class I mRNA levels. As can be clearly seen in FIG. 18B, patients bearing a high pSTAT1/SOCS1 ratio also possessed higher levels of MHC class 1 message expression which reached statistical significance with HLA-HQ:DAR. Given the importance of MHC associated antigen presentation to the progression of SLE, this result suggests that a high pSTAT1/SOCS1 ratio may be predictive of SLE pathology, and further implicates reduced SOCS1 signaling to SLE disease progression.

Example 16

IFNγ Production is Positively Correlated to SOCS1 Protein Levels

As it has been previously shown in rodent models that SOCS 1/3 induction can be mediated by several pro-inflammatory cytokines, we next assessed a relationship between SOCS1/3 induction in SLE patients and IL27, IFNγ, and type 1 interferon signaling. Notably, we observed a significantly lower level of IFNγ message levels in patients versus control samples, while IL27 levels were comparable (FIG. 18A). We next compared SOCS1/3 message and protein levels, in SLE patients, with IFNγ message levels, IL27 message levels, and CD64 expression (which has been shown to be a marker of a type 1 interferon signature). Although SOCS1 and SOCS3 protein levels yielded no statistically significant relationship between IFNγ, IL27, or CD64; SOCS1 and SOCS3 message levels in SLE patients were positively correlated to both IFNγ and IL27 (FIGS. 18B, 18C, and 18D). Together, these data support the notion that IFNγ signaling may be important in the production of SOCS1 protein.

Example 17

Prednisone Treatment is Correlated with Enhanced SOCS1 and SOCS3 Protein Levels

Figure 19:
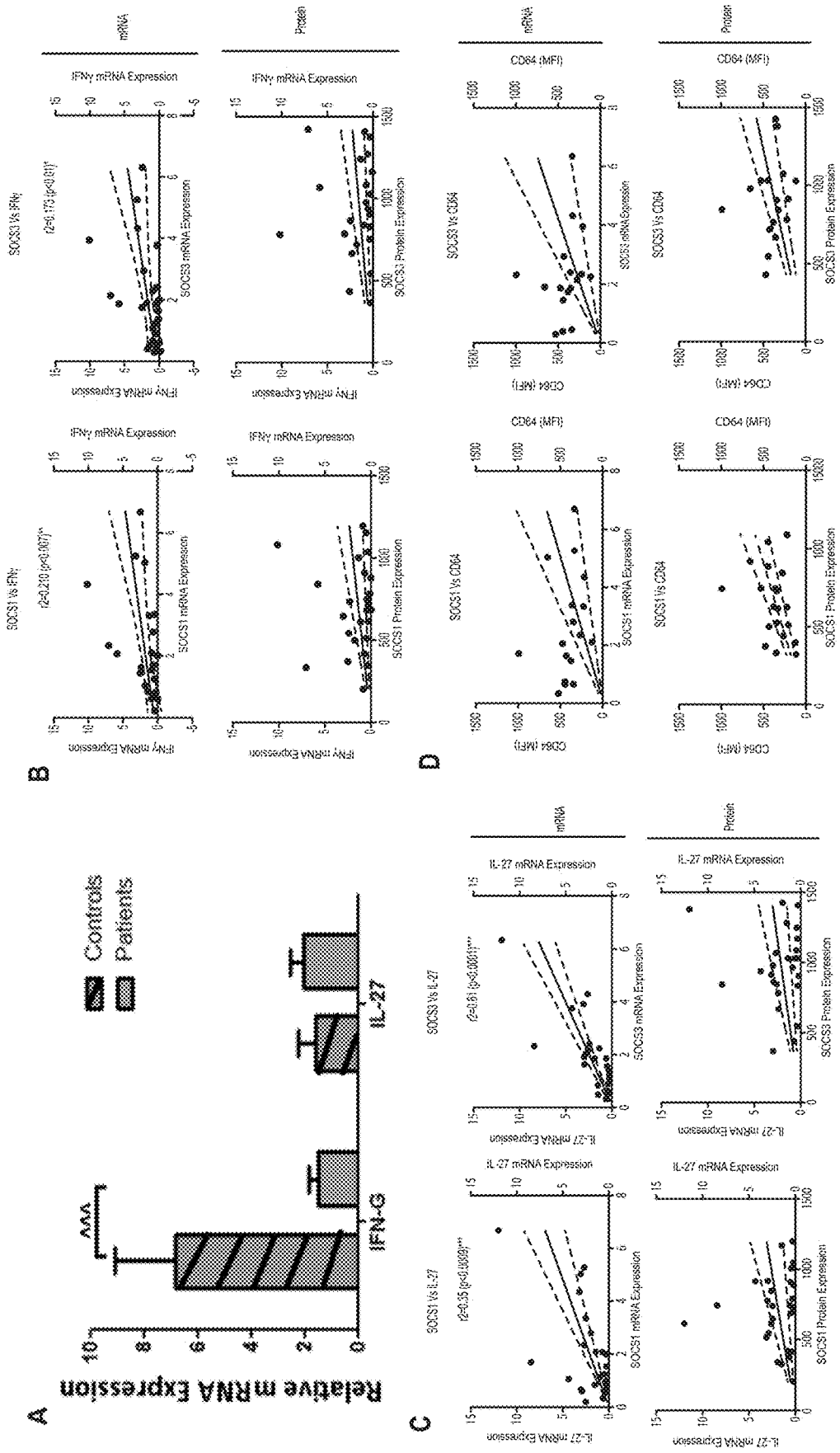
FIGS. 19A-19D. IFN gamma and IL27 mRNA levels are positively correlated to SOCS1 mRNA levels.
Figure 20:
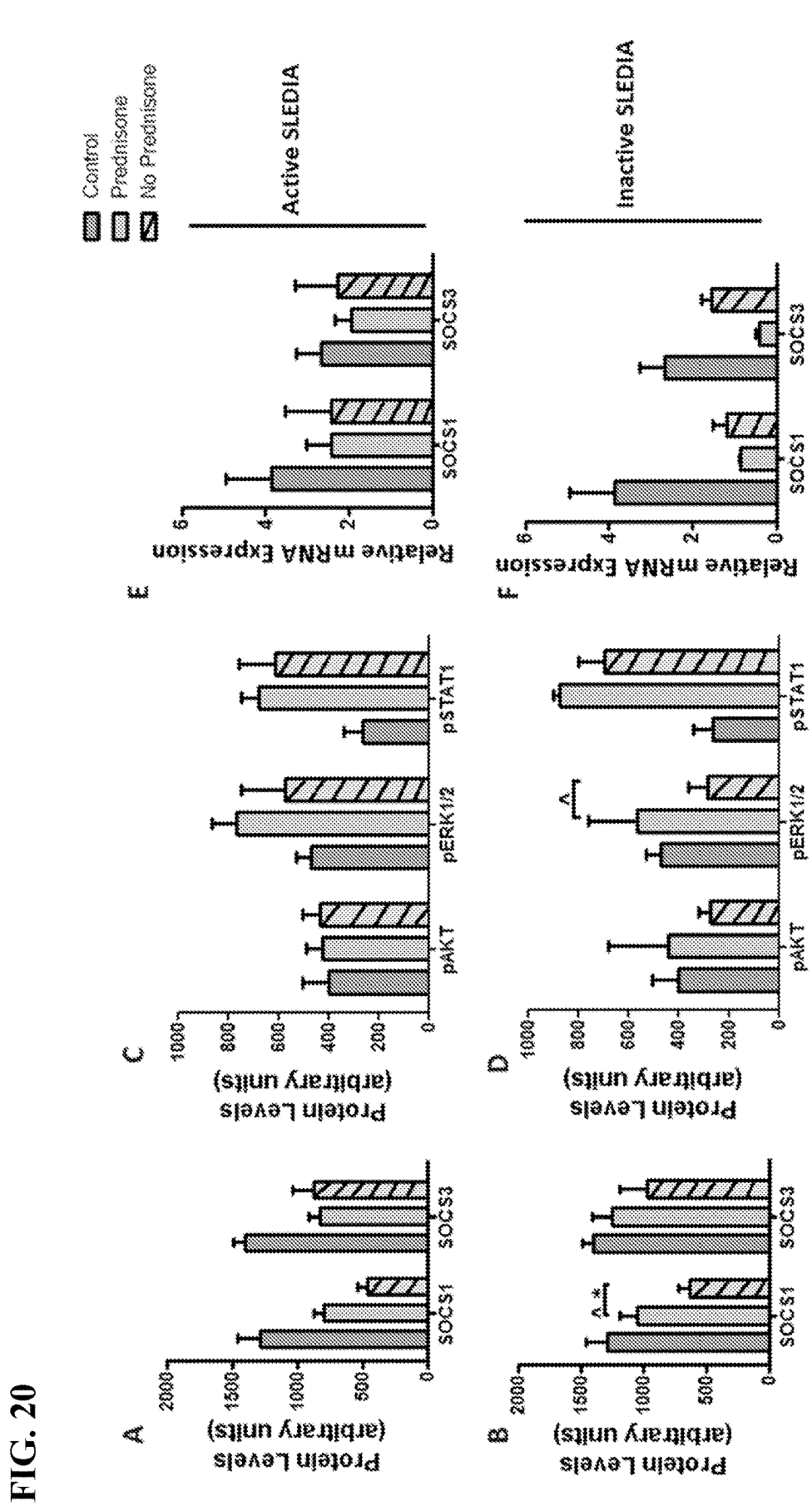
FIGS. 20A-20F. Subgroup analysis of SOCS1 and SOCS3 expression in SLE patients with and without prednisone treatment: Active SLEDIA and inactive SLEDIA SLE patients with and without prednisone treatment were analyzed for SOCS1 and SOCS3 mRNA and protein expression relative to GAPDH, in comparison to controls (N=6). Protein expression represented by graph (FIG. 20A) Active SLEDIA (FIG. 20B) Inactive SLEDIA; Phosphorylated protein expression of pAKT; pERK1/2 and pSTAT1 represented by graph (FIG. 20C) Active SLEDIA (FIG. 20D) Inactive SLEDIA and mRNA expression represented by graph (FIG. 20E) Active SLEDIA (FIG. 20F) Inactive SLEDIA in comparison to healthy controls respectively (N=6). Results shown are mean±SE; *represents significant Pearson correlation; ˆ represents a t-test with significant mean difference. Correlation was considered significant at 0.05 level (2 tailed).

In order to analyze the possible effects of prednisone treatment and SLE disease activity on KIR containing protein expression, subgroup analyses among SLE patients was performed. As can be seen in FIG. 19, patients receiving prednisone consistently had higher SOCS1 protein levels than those not receiving prednisone, reaching significance among patients with an inactive SLEDIA score (n=9, p=p<0.001). In contrast, prednisone treatment had no effect of SOCS3 protein levels. In terms of cellular activation, patients receiving prednisone treatment had higher levels of pErk1/2 activation, again reaching statistical significance within inactive SLEDIA patients. Notably, prednisone treatment had no effect on either SOCS 1/3 message expression or STAT1 phosphorylation (FIG. 19B). Together, these data show that enhanced SOCS1 levels were present in patients receiving prednisone treatment, but with no observed differences in STAT1 phosphorylation.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

U.S. Pat. No. 4,179,337
U.S. Pat. No. 4,625,014
U.S. Pat. No. 5,034,322
U.S. Pat. No. 5,106,739
U.S. Pat. No. 5,252,348
U.S. Pat. No. 5,625,136
U.S. Pat. No. 5,763,585
U.S. Patent Application No. 20020035243
U.S. Patent Application No. 20020120100
U.S. Patent Application No. 20030032594
Akahoshi, M., Nakashima, H., Tanaka, Y., Kohsaka, T., Nagano, S., Ohgami, E., Arinobu, Y., Yamaoka, K., Niiro, H., Shinozaki, M. et al. 1999. Th1/Th2 balance of peripheral T helper cells in systemic lupus erythematosus. Arthritis Rheum. 42:1644-1648.
Alexander, W. S. 2002. Suppressors of cytokine signalling (SOCS) in the immune system. Nat. Rev. Immunol. 2:410-416.
Alexander, W. S., Starr, R., Fenner, J. E., Scott, C. L., Handman, E., Sprigg, N. S., Corbin, J. E., Cornish, A. L., Darwiche, R., Owczarek, C. M. et al. 1999. SOCS1 is a critical inhibitor of interferon gamma signaling and prevents the potentially fatal neonatal actions of this cytokine Cell 98:597-608.
Altschul, S. F. et al. (1990) "Basic Local Alignment Search Tool" J. Mol. Biol. 215:403-410.
Altschul, S. F. et al. (1997) "Gapped BLAST and PSI-BLAST: A New Generation of Protein Database Search Programs" Nucl. Acids Res. 25:3389-3402.
Balomenos, D., Rumold, R., and Theofilopoulos, A. N. 1998. Interferon-gamma is required for lupus-like disease and lymphoaccumulation in MRL-lpr mice. J. Clin. Invest. 101:364-371.
Bedoya, S. K., Wilson, T. D., Collins, E. L., Lau, K., and Larkin III, J. 2013. Isolation and Th17 Differentiation of Naïve CD4 T Lymphocytes. J. Vis. Exp. 79: e50765, doi:10.3791/50765.
Beltz, G. A., Jacobs, K. A., Eickbush, T. H., Cherbas, P. T., Kafatos, F. C. (1983) "Isolation of multigene families and determination of homologies by filter hybridization methods" Methods of Enzymology, R. Wu, L. Grossman and K. Moldave [eds.] Academic Press, New York 100:266-285.
Bhattacharyya, S., Zhao, Y., Kay, T. W., and Muglia, L. J. 2011. Glucocorticoids target suppressor of cytokine signaling 1 (SOCS1) and type 1 interferons to regulate Toll-like receptor-induced STAT1 activation. Proc. Natl. Acad. Sci. U.S.A. 108:9554-9559.
Bombardier C, Gladman D D, Urowitz M B, Caron D, Chang C H. Derivation of the SLEDAI. A disease activity index for lupus patients. the committee on prognosis studies in SLE. Arthritis Rheum. 1992 June; 35(6):630-40.
Bouzahzah, F., Jung, S., and Craft, J. 2003. CD4+ T cells from lupus-prone mice avoid antigen-specific tolerance induction in vivo. J. Immunol. 170:741-748.
Caretto, D., Katzman, S. D., Villarino, A. V., Gallo, E., and Abbas, A. K. 2010. Cutting edge: the Th1 response inhibits the generation of peripheral regulatory T cells. J. Immunol. 184:30-34.
Chan, H. C., Ke, L. Y., Chang, L. L., Liu, C. C., Hung, Y. H., Lin, C. H., Li, R. N., Tsai, W. C., Liu, H. W., and Yen, J.

H. 2010. Suppressor of cytokine signaling 1 gene expression and polymorphisms in systemic lupus erythematosus. Lupus 19:696-702.

Cheng, G., Yu, A., and Malek, T. R. 2011. T-cell tolerance and the multi-functional role of IL-2R signaling in T-regulatory cells. Immunol. Rev. 241:63-76.

Collins, E. L., Jager, L. D., Dabelic, R., Benitez, P., Holdstein, K., Lau, K., Haider, M. I., Johnson, H. M., and Larkin, J., 3rd. 2011. Inhibition of SOCS1−/− lethal autoinflammatory disease correlated to enhanced peripheral Foxp3+ regulatory T cell homeostasis. J. Immunol. 187:2666-2676.

Cozzo, C., Larkin, J., 3rd, and Caton, A. J. 2003. Cutting edge: self-peptides drive the peripheral expansion of CD4+CD25+ regulatory T cells. J. Immunol. 171:5678-5682.

de Boer, H. A., Comstock, L. J., Vasser, M. (1983) "The tac promoter: a functional hybrid derived from the trp and lac promoters" *Proc. Natl. Acad. Sci. USA* 80(1):21-25.

Desai-Mehta, A., Lu, L., Ramsey-Goldman, R., and Datta, S. K. 1996. Hyperexpression of CD40 ligand by B and T cells in human lupus and its role in pathogenic autoantibody production. J. Clin. Invest. 97:2063-2073.

Diehl, S., Anguita, J., Hoffmeyer, A., Zapton, T., Ihle, J. N., Fikrig, E., and Rincon, M. 2000. Inhibition of Th1 differentiation by IL-6 is mediated by SOCS1. Immunity 13:805-815.

Egwuagu C E, Larkin J III., *JAK-STAT* (2013) 2:e24134; http://dx.doi.org/10.4161/jkst.24134.

Felgner, P. L., T. R. Gadek, M. Holm, R. Roman, H. W. Chan, M. Wenz, J. P. Northrop, G. M. Ringold, M. Danielsen (1987) "Lipofection: a highly efficient, lipid-mediated DNA-transfection procedure" *Proc Natl Acad Sci U.S.A.* 84(21):7413-7417.

Feng, T., Cao, A. T., Weaver, C. T., Elson, C. O., and Cong, Y. 2011. Interleukin-12 converts Foxp3+ regulatory T cells to interferon-gamma-producing Foxp3+ T cells that inhibit colitis. Gastroenterology 140:2031-2043.

Fujimoto, M., Tsutsui, H., Xinshou, O., Tokumoto, M., Watanabe, D., Shima, Y., Yoshimoto, T., Hirakata, H., Kawase, I., Nakanishi, K. et al. 2004. Inadequate induction of suppressor of cytokine signaling-1 causes systemic autoimmune diseases. Int. Immunol. 16:303-314.

Gett, A. V., and Hodgkin, P. D. 1998. Cell division regulates the T cell cytokine repertoire, revealing a mechanism underlying immune class regulation. Proc. Natl. Acad. Sci. U.S.A. 95:9488-9493.

Greenlund, A. C., Morales, M. O., Viviano, B. L., Yan, H., Krolewski, J., and Schreiber, R. D. 1995. Stat recruitment by tyrosine-phosphorylated cytokine receptors: an ordered reversible affinity-driven process. Immunity 2:677-687.

Gurevitz, S. L., Snyder, J. A., Wessel, E. K., Frey, J., and Williamson, B. A. 2013. Systemic lupus erythematosus: a review of the disease and treatment options. Consult. Pharm. 28:110-121.

Haas, C., Ryffel, B., and Le Hir, M. 1998. IFN-gamma receptor deletion prevents autoantibody production and glomerulonephritis in lupus-prone (NZBxNZW)F1 mice. J. Immunol. 160:3713-3718.

Hanada, T., Yoshida, H., Kato, S., Tanaka, K., Masutani, K., Tsukada, J., Nomura, Y., Mimata, H., Kubo, M., and Yoshimura, A. 2003. Suppressor of cytokine signaling-1 is essential for suppressing dendritic cell activation and systemic autoimmunity. Immunity 19:437-450.

Hirahara, K., Poholek, A., Vahedi, G., Laurence, A., Kanno, Y., Milner, J. D., and O'Shea, J. J. 2013. Mechanisms underlying helper T-cell plasticity: implications for immune-mediated disease. J. Allergy Clin. Immunol. 131:1276-1287.

Iannone, F., and Lapadula, G. 2012. The inhibitor of costimulation of T cells: abatacept. J. Rheumatol. Suppl. 89:100-102.

Jabs, D. A., Burek, C. L., Hu, Q., Kuppers, R. C., Lee, B., and Prendergast, R. A. 1992. Anti-CD4 monoclonal antibody therapy suppresses autoimmune disease in MRL/Mp-lpr/lpr mice. Cell. Immunol. 141:496-507.

Jager, L. D., Dabelic, R., Waiboci, L. W., Lau, K., Haider, M. S., Ahmed, C. M., Larkin, J., 3rd, David, S., and Johnson, H. M. 2011. The kinase inhibitory region of SOCS-1 is sufficient to inhibit T-helper 17 and other immune functions in experimental allergic encephalomyelitis. J. Neuroimmunol. 232:108-118.

Jorgensen, T. N., Roper, E., Thurman, J. M., Marrack, P., and Kotzin, B. L. 2007. Type I interferon signaling is involved in the spontaneous development of lupus-like disease in B6.Nba2 and (B6.Nba2xNZW)F(1) mice. Genes Immun. 8:653-662.

Karlin S., Altschul, S. F. (1993) "Applications and Statistics for Multiple High-Scoring Segments in Molecular Sequences" *Proc. Natl. Acad. Sci. USA* 90:5873-5877.

Karonitsch, T., Feierl, E., Steiner, C. W., Dalwigk, K., Korb, A., Binder, N., Rapp, A., Steiner, G., Scheinecker, C., Smolen, J. et al. 2009. Activation of the interferon-gamma signaling pathway in systemic lupus erythematosus peripheral blood mononuclear cells. Arthritis Rheum. 60:1463-1471.

Knosp, C. A., and Johnston, J. A. 2012. Regulation of CD4+ T-cell polarization by suppressor of cytokine signalling proteins. Immunology 135:101-111.

Kohler, G. and C. Milstein (1975) "Continuous cultures of fused cells secreting antibody of predefined specificity" *Nature* 256(5517):495-497.

Kotenko, S. V., and Pestka, S. 2000. Jak-Stat signal transduction pathway through the eyes of cytokine class II receptor complexes. Oncogene 19:2557-2565.

Larkin, J., 3rd, Picca, C. C., and Caton, A. J. 2007. Activation of CD4+ CD25+ regulatory T cell suppressor function by analogs of the selecting peptide. Eur. J. Immunol. 37:139-146.

Lau, K., Benitez, P., Ardissone, A., Wilson, T. D., Collins, E. L., Lorca, G., Li, N., Sankar, D., Wasserfall, C., Neu, J. et al. 2011 Inhibition of type 1 diabetes correlated to a *Lactobacillus johnsonii* N6.2-mediated Th17 bias. J. Immunol. 186:3538-3546.

Ledford, H. 2011. Melanoma drug wins US approval. Nature 471:561.

Li, Y., Lee, P. Y., Kellner, E. S., Paulus, M., Switanek, J., Xu, Y., Zhuang, H., Sobel, E. S., Segal, M. S., Satoh, M. et al. 2010. Monocyte surface expression of Fcgamma receptor RI (CD64), a biomarker reflecting type-I interferon levels in systemic lupus erythematosus. Arthritis Res. Ther. 12:R90.

Mangan, P. R., Harrington, L. E., O'Quinn, D. B., Helms, W. S., Bullard, D. C., Elson, C. O., Hatton, R. D., Wahl, S. M., Schoeb, T. R., and Weaver, C. T. 2006. Transforming growth factor-beta induces development of the T(H)17 lineage. Nature 441:231-234.

Maniatis, T., Fritsch, E. F., Sambrook, J. (1982) *Molecular Cloning: A Laboratory Manual*, Cold Spring Harbor Laboratory, Cold Spring Harbor, N.Y.

Mohan, C., Yu, Y., Morel, L., Yang, P., and Wakeland, E. K. 1999. Genetic dissection of Sle pathogenesis: Sle3 on murine chromosome 7 impacts T cell activation, differentiation, and cell death. J. Immunol. 162:6492-6502.

Mondino, A., and Jenkins, M. K. 1994. Surface proteins involved in T cell costimulation. J. Leukoc. Biol. 55:805-815.

Morel, L., Croker, B. P., Blenman, K. R., Mohan, C., Huang, G., Gilkeson, G., and Wakeland, E. K. 2000. Genetic reconstitution of systemic lupus erythematosus immunopathology with polycongenic murine strains. Proc. Natl. Acad. Sci. U.S.A. 97:6670-6675.

Nacionales, D. C., Kelly-Scumpia, K. M., Lee, P. Y., Weinstein, J. S., Lyons, R., Sobel, E., Satoh, M., and Reeves, W. H. 2007. Deficiency of the type I interferon receptor protects mice from experimental lupus. Arthritis Rheum. 56:3770-3783.

Nakashima, H., Inoue, H., Akahoshi, M., Tanaka, Y., Yamaoka, K., Ogami, E., Nagano, S., Arinobu, Y., Niiro, H., Otsuka, T. et al. 1999. The combination of polymorphisms within interferon-gamma receptor 1 and receptor 2 associated with the risk of systemic lupus erythematosus. FEBS Lett. 453:187-190.

Pardanani, A., Gotlib, J. R., Jamieson, C., Cortes, J. E., Talpaz, M., Stone, R. M., Silverman, M. H., Gilliland, D. G., Shorr, J., and Tefferi, A. 2011. Safety and efficacy of TG101348, a selective JAK2 inhibitor, in myelofibrosis. J. Clin. Oncol. 29:789-796.

Parry, R. V., Reif, K., Smith, G., Sansom, D. M., Hemmings, B. A., and Ward, S. G. 1997. Ligation of the T cell co-stimulatory receptor CD28 activates the serine-threonine protein kinase protein kinase B. Eur. J. Immunol. 27:2495-2501.

Picca, C. C., Larkin, J., 3rd, Boesteanu, A., Lerman, M. A., Rankin, A. L., and Caton, A. J. 2006. Role of TCR specificity in CD4+ CD25+ regulatory T-cell selection. Immunol. Rev. 212:74-85.

Pickering, M. C., and Walport, M. J. 2000. Links between complement abnormalities and systemic lupus erythematosus. Rheumatology (Oxford) 39:133-141.

Pierau, M., Engelmann, S., Reinhold, D., Lapp, T., Schraven, B., and Bommhardt, U. H. 2009. Protein kinase B/Akt signals impair Th17 differentiation and support natural regulatory T cell function and induced regulatory T cell formation. J. Immunol. 183:6124-6134.

Piganis, R. A., De Weerd, N. A., Gould, J. A., Schindler, C. W., Mansell, A., Nicholson, S. E., and Hertzog, P. J. 2011. Suppressor of cytokine signaling (SOCS) 1 inhibits type I interferon (IFN) signaling via the interferon alpha receptor (IFNAR1)-associated tyrosine kinase Tyk2. J. Biol. Chem. 286:33811-33818.

Platanias, L. C., and Fish, E. N. 1999. Signaling pathways activated by interferons. Exp. Hematol. 27:1583-1592.

Ronnblom, L. E., Alm, G. V., and Oberg, K. E. 1991. Autoimmunity after alpha-interferon therapy for malignant carcinoid tumors. Ann. Intern. Med. 115:178-183.

Santiago-Raber, M. L., Baccala, R., Haraldsson, K. M., Choubey, D., Stewart, T. A., Kono, D. H., and Theofilopoulos, A. N. 2003. Type-I interferon receptor deficiency reduces lupus-like disease in NZB mice. J. Exp. Med. 197:777-788.

Santoro, T. J., Portanova, J. P., and Kotzin, B. L. 1988. The contribution of L3T4+ T cells to lymphoproliferation and autoantibody production in MRL-lpr/lpr mice. J. Exp. Med. 167:1713-1718.

Schroder, K., Hertzog, P. J., Ravasi, T., and Hume, D. A. 2004. Interferon-gamma: an overview of signals, mechanisms and functions. J. Leukoc. Biol. 75:163-189.

Sharabi, A., Sthoeger, Z. M., Mahlab, K., Lapter, S., Zinger, H., and Mozes, E. 2009. A tolerogenic peptide that induces suppressor of cytokine signaling (SOCS)-1 restores the aberrant control of IFN-gamma signaling in lupus-affected (NZBxNZW)F1 mice. Clin. Immunol. 133:61-68.

Stekman, I. L., Blasini, A. M., Leon-Ponte, M., Baroja, M. L., Abadi, I., and Rodriguez, M. A. 1991. Enhanced CD3-mediated T lymphocyte proliferation in patients with systemic lupus erythematosus. Arthritis Rheum. 34:459-467.

Suen, J. L., Li, H. T., Jong, Y. J., Chiang, B. L., and Yen, J. H. 2009. Altered homeostasis of CD4(+) FoxP3(+) regulatory T-cell subpopulations in systemic lupus erythematosus. Immunology 127:196-205.

Szabo, S. J., Sullivan, B. M., Stemmann, C., Satoskar, A. R., Sleckman, B. P., and Glimcher, L. H. 2002. Distinct effects of T-bet in TH1 lineage commitment and IFN-gamma production in CD4 and CD8 T cells. Science 295:338-342.

Szente, B. E., Soos, J. M., and Johnson, H. W. 1994. The C-terminus of IFN gamma is sufficient for intracellular function. Biochem. Biophys. Res. Commun. 203:1645-1654.

Takahashi, R., Nishimoto, S., Muto, G., Sekiya, T., Tamiya, T., Kimura, A., Morita, R., Asakawa, M., Chinen, T., and Yoshimura, A. 2011. SOCS1 is essential for regulatory T cell functions by preventing loss of Foxp3 expression as well as IFN-{gamma} and IL-17A production. J. Exp. Med. 208:2055-2067.

Takahashi, S., Fossati, L., Iwamoto, M., Merino, R., Motta, R., Kobayakawa, T., and Izui, S. 1996. Imbalance towards Th1 predominance is associated with acceleration of lupus-like autoimmune syndrome in MRL mice. J. Clin. Invest. 97:1597-1604.

Tam, J. P. (1988) "Synthetic Peptide Vaccine Design: Synthesis and Properties of a High-Density Multiple Antigenic Peptide System" *Biochemistry* 85:5409-5413.

Tan, E. M., Cohen, A. S., Fries, J. F., Masi, A. T., McShane, D. J., Rothfield, N. F., Schaller, J. G., Talal, N., and Winchester, R. J. 1982. The 1982 revised criteria for the classification of systemic lupus erythematosus. Arthritis Rheum. 25:1271-1277.

Testi, R., D'Ambrosio, D., De Maria, R., and Santoni, A. 1994. The CD69 receptor: a multipurpose cell-surface trigger for hematopoietic cells. Immunol. Today 15:479-483

Thiam, K., Loing, E., Verwaerde, C., Auriault, C., and Gras-Masse, H. 1999. IFN-gamma-derived lipopeptides: influence of lipid modification on the conformation and the ability to induce MHC class II expression on murine and human cells. J. Med. Chem. 42:3732-3736.

Tivol, E. A., Schweitzer, A. N., and Sharpe, A. H. 1996. Costimulation and autoimmunity. Curr. Opin. Immunol. 8:822-830.

Tsao, J. T., Kuo, C. C., and Lin, S. C. 2008. The analysis of CIS, SOCS1, SOSC2 and SOCS3 transcript levels in peripheral blood mononuclear cells of systemic lupus erythematosus and rheumatoid arthritis patients. Clin. Exp. Med. 8:179-185.

Tsokos, G. C. 2011. Systemic lupus erythematosus. N. Engl. J. Med. 365:2110-2121.

Valencia, X., Yarboro, C., Illei, G., and Lipsky, P. E. 2007. Deficient CD4+CD25 high T regulatory cell function in patients with active systemic lupus erythematosus. J. Immunol. 178:2579-2588.

Vratsanos, G. S., Jung, S., Park, Y. M., and Craft, J. 2001. CD4(+) T cells from lupus-prone mice are hyperresponsive to T cell receptor engagement with low and high affinity peptide antigens: a model to explain spontaneous T cell activation in lupus. J. Exp. Med. 193:329-337.

Wang, S., Yang, N., Zhang, L., Huang, B., Tan, H., Liang, Y., Li, Y., and Yu, X. 2010. Jak/STAT signaling is involved in the inflammatory infiltration of the kidneys in MRL/lpr mice. Lupus 19:1171-1180.

Wofsy, D., Ledbetter, J. A., Hendler, P. L., and Seaman, W. E. 1985. Treatment of murine lupus with monoclonal anti-T cell antibody. J. Immunol. 134:852-857.

Xu, D., McElroy, D., Thornburg, R. W., Wu, R. et al. (1993) "Systemic induction of a potato pin2 promoter by wounding, methyl jasmonate, and abscisic acid in transgenic rice plants" *Plant Molecular Biology* 22:573-588.

Yan, B., Ye, S., Chen, G., Kuang, M., Shen, N., and Chen, S. 2008. Dysfunctional CD4+, CD25+ regulatory T cells in untreated active systemic lupus erythematosus secondary to interferon-alpha-producing antigen-presenting cells. Arthritis Rheum. 58:801-812.

Yoshimura, A., Suzuki, M., Sakaguchi, R., Hanada, T., and Yasukawa, H. 2012. SOCS, Inflammation, and Autoimmunity. Front. Immunol. 3:20.

Zhang, J. G., Metcalf, D., Rakar, S., Asimakis, M., Greenhalgh, C. J., Willson, T. A., Starr, R., Nicholson, S. E., Carter, W., Alexander, W. S. et al. 2001. The SOCS box of suppressor of cytokine signaling-1 is important for inhibition of cytokine action in vivo. Proc. Natl. Acad. Sci. U.S.A. 98:13261-13265.

Zielinski, C. E., Jacob, S. N., Bouzahzah, F., Ehrlich, B. E., and Craft, J. 2005. Naive CD4+ T cells from lupus-prone Fas-intact MRL mice display TCR-mediated hyperproliferation due to intrinsic threshold defects in activation. J. Immunol. 174:5100-5109.

We claim:

1. A peptide mimetic of a suppressor of cytokine signaling (SOCS) protein that binds to and inhibits the activity of a tyrosine kinase, wherein said peptide mimetic comprises two copies of the SOCS1-kinase inhibitory region (KIR) amino acid sequence DTHFRTFRSHSDYRRI (SEQ ID NO: 1), and wherein said peptide mimetic comprises a linker amino acid sequence of five or more glycine amino acids positioned between and attached to a terminus of each of said two SOCS1-KIR amino acid sequences.

2. The peptide mimetic according to claim 1, wherein said tyrosine kinase is a Janus kinase (JAK) protein.

3. The peptide mimetic according to claim 2, wherein said JAK protein is JAK2.

4. The peptide mimetic according to claim 1, wherein said peptide mimetic further comprises a nuclear localization sequence (NLS).

5. The peptide mimetic according to claim 1, wherein said peptide mimetic further comprises a protein or nucleic acid that is attached to said peptide mimetic and that targets delivery to a cell and/or that provides for translocation of said peptide mimetic across a biological membrane of said cell.

6. The peptide mimetic according to claim 1, wherein a lipophilic group is attached to said peptide mimetic.

7. The peptide mimetic according to claim 6, wherein said lipophilic group is a palmitoyl-lysine group.

8. The peptide mimetic according to claim 6, wherein said lipophilic group comprises one or more arginine and/or lysine amino acids at the N-terminus, the C-terminus, or both the N-terminus and C-terminus of said peptide mimetic.

9. The peptide mimetic according to claim 8, wherein said peptide mimetic comprises the amino acid sequence of SEQ ID NO: 29.

10. The peptide mimetic according to claim 6, wherein said lipophilic group comprises a fatty acid moiety.

11. The peptide mimetic according to claim 10, wherein said fatty acid is capric acid, lauric acid, myristic acid, palmitic acid, stearic acid, arachidic acid, behenic acid, lignoceric acid, or cerotic acid.

12. The peptide mimetic according to claim 1, wherein said peptide mimetic binds to the activation loop of JAK2 and/or TYK2.

13. The peptide mimetic according to claim 1, wherein said peptide mimetic consists of the amino acid sequence of SEQ ID NO: 3 and one or more arginine and/or lysine amino acids at the N-terminus, the C-terminus, or both the N-terminus and the C-terminus of said peptide mimetic.

14. The peptide mimetic according to claim 1, wherein said peptide mimetic consists of the amino acid sequence of SEQ ID NO: 3 and wherein a lipophilic group is attached to said peptide mimetic.

15. The peptide mimetic according to claim 14, wherein said lipophilic group is a palmitoyl-lysine group.

16. The peptide mimetic according to claim 14, wherein said lipophilic group is a fatty acid moiety.

17. The peptide mimetic according to claim 16, wherein said fatty acid is capric acid, lauric acid, myristic acid, palmitic acid, stearic acid, arachidic acid, behenic acid, lignoceric acid, or cerotic acid.

18. The peptide mimetic according to claim 1, wherein a polyethylene glycol moiety is attached to said peptide mimetic.

19. The peptide mimetic according to claim 1, wherein a cell-penetrating peptide (CPP) is attached to said peptide mimetic.

20. The peptide mimetic according to claim 19, wherein said CPP comprises the amino acid sequence of one or more of SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, or SEQ ID NO: 49.

21. The peptide mimetic according to claim 1, wherein said peptide mimetic consists of the amino acid sequence of SEQ ID NO: 3 and wherein a polyethylene glycol moiety is attached to said peptide mimetic.

22. The peptide mimetic according to claim 1, wherein said peptide mimetic consists of the amino acid sequence of SEQ ID NO: 3 and wherein a CPP is attached to said peptide mimetic.

23. The peptide mimetic according to claim 22, wherein said CPP is the amino acid sequence of one or more of SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, or SEQ ID NO: 49.

24. The peptide mimetic according to claim 1, wherein said peptide mimetic consists of the amino acid sequence of SEQ ID NO: 3.

25. A composition comprising a peptide mimetic of claim 1, wherein said composition further comprises a suitable carrier, diluent, or buffer; or
wherein said peptide mimetic is encapsulated in a liposome; or
wherein said composition further comprises one or more anticancer or antitumor compound, and/or one or more compound for treating an autoimmune or inflammatory disorder.

26. The composition according to claim 25, wherein the one or more anticancer or antitumor compound is taxol, vinblastine, cyclophosamide, ifosfamide, 5-fluorouracil, hydroxyurea, adriamycin, bleomycin, etoposide, camptothecin, angiostatin, tamoxifen, Imatinib, Trastuzumab, Bortezomib, Carfilzomib, or Salinosporamide A.

27. A polynucleotide comprising a nucleotide sequence that encodes one or more of the peptide mimetic of claim 1.

28. The polynucleotide according to claim 27, wherein said polynucleotide comprises regulatory elements that provide for expression of said nucleotide sequence in a cell.

29. The polynucleotide according to claim 28, wherein said cell is a bacterial cell.

30. The polynucleotide according to claim 28, wherein said cell is a yeast cell, a plant cell, an insect cell, or a mammalian cell.

31. The polynucleotide according to claim 28, wherein said cell is a human cell.

32. The polynucleotide according to claim 27, wherein said polynucleotide further comprises a nucleotide sequence encoding a CPP attached to said peptide mimetic.

33. The polynucleotide according to claim 32, wherein said CPP comprises the amino acid sequence of one or more of SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, or SEQ ID NO: 49.

34. The polynucleotide according to claim 27, wherein said polynucleotide further comprises a nucleotide sequence encoding a nuclear localization sequence (NLS).

35. The polynucleotide according to claim 27, wherein said polynucleotide further comprises a nucleotide sequence encoding one or more arginine and/or lysine amino acids at the N-terminus, the C-terminus, or both the N-terminus and the C-terminus of said peptide mimetic.

* * * * *

UNITED STATES PATENT AND TRADEMARK OFFICE
CERTIFICATE OF CORRECTION

PATENT NO. : 11,603,387 B2
APPLICATION NO. : 15/113725
DATED : March 14, 2023
INVENTOR(S) : Howard M. Johnson et al.

It is certified that error appears in the above-identified patent and that said Letters Patent is hereby corrected as shown below:

In the Specification

Column 32,
Line 22, "(10 µM;" should read --(1µM;--.

Page 1 of 1

Signed and Sealed this
Twenty-ninth Day of August, 2023

Katherine Kelly Vidal
*Director of the United States Patent and Trademark Office*